US012570714B2

(12) United States Patent
Cohen et al.

(10) Patent No.: US 12,570,714 B2
(45) Date of Patent: Mar. 10, 2026

(54) SIGLEC-BASED CHIMERIC POLYPEPTIDES AND USES THEREOF

(71) Applicant: Bar-Ilan University, Ramat-Gan (IL)

(72) Inventors: Cyrille Joseph Cohen, Petach-Tikva (IL); Yishai Reboh, RaAnana (IL); Sara Meril, Ashdod (IL); Vasyl Eisenberg, Petach Tikva (IL)

(73) Assignee: Bar-Ilan University, Ramat-Gan (IL)

( * ) Notice: Subject to any disclaimer, the term of this patent is extended or adjusted under 35 U.S.C. 154(b) by 1170 days.

(21) Appl. No.: 17/604,495

(22) PCT Filed: Apr. 16, 2020

(86) PCT No.: PCT/IL2020/050445
§ 371 (c)(1),
(2) Date: Oct. 18, 2021

(87) PCT Pub. No.: WO2020/212986
PCT Pub. Date: Oct. 22, 2020

(65) Prior Publication Data
US 2022/0211831 A1     Jul. 7, 2022

Related U.S. Application Data

(60) Provisional application No. 62/834,995, filed on Apr. 17, 2019.

(51) Int. Cl.
| | |
|---|---|
| *A61K 40/31* | (2025.01) |
| *A61K 40/11* | (2025.01) |
| *A61K 40/32* | (2025.01) |
| *A61K 40/42* | (2025.01) |
| *A61P 35/00* | (2006.01) |
| *C07K 14/705* | (2006.01) |
| *C07K 14/725* | (2006.01) |
| *C07K 19/00* | (2006.01) |

(52) U.S. Cl.
CPC .......... *C07K 14/7051* (2013.01); *A61K 40/11* (2025.01); *A61K 40/31* (2025.01); *A61K 40/32* (2025.01); *A61K 40/421* (2025.01); *A61K 40/4211* (2025.01); *A61K 40/4269* (2025.01); *A61K 40/4272* (2025.01); *A61P 35/00* (2018.01); *C07K 14/70521* (2013.01); *A61K 2239/31* (2023.05); *A61K 2239/48* (2023.05); *A61K 2239/57* (2023.05); *C07K 2319/03* (2013.01)

(58) Field of Classification Search
None
See application file for complete search history.

(56) References Cited

FOREIGN PATENT DOCUMENTS

| | | |
|---|---|---|
| WO | WO 2016/178996 | 11/2016 |
| WO | WO 2017/123745 | 7/2017 |
| WO | WO 2018/002640 | 1/2018 |
| WO | WO 2020/212986 | 10/2020 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser: Boston, pp. 491-495.*
Skolnick et al.(2000). Trends in Biotech. 18(1):34-39.*
International Search Report and the Written Opinion Dated Jun. 28, 2020 From the International Searching Authority Re. Application No. PCT/IL2020/050445. (10 Pages).
Angata et al. "Therapeutic Targeting of Siglecs Using Antibody- and Glycan-Based Approaches", Trends in Pharmacological Science, 36(10): 645-660, Oct. 2015.
Jandus et al. "Interactions Between Siglec-7/9 Receptors and Ligands Influence NK Cell-Dependent Tumor Immunosurveillance", The Journal of Clinical Investigation, 124(4): 1810-1820, Apr. 2014.
Kannagi et al. "Altered Expression of Glycan Genes in Cancers Induced by Epigenetic Silencing and Tumor Hypoxia: Clues in the Ongoing Search for New Tumor Markers", Cancer Science, 101(3): 586-593, Published Online Jan. 18, 2010.
Walter et al. "ITIM-Dependent Endocytosis of CD33-Related Siglecs: Role of Intracellular Domain, Tyrosine Phosphorylation, and the Tyrosine Phosphatases, Shp1 and Shp2", Journal of Leukocyte Biology, 83(1): 200-211, Published Online Oct. 18, 2007.

* cited by examiner

*Primary Examiner* — Christine J Saoud
*Assistant Examiner* — Jon M Lockard

(57)     ABSTRACT

Provided are Siglec-based chimeric polypeptides. Accordingly there is provided a chimeric receptor comprising: (a) an extracellular domain comprising an amino acid sequence of a Siglec-7 or a Siglec-9 receptor capable of binding a Siglec-7 and/or a Siglec-9 ligand; and (b) an intracellular domain comprising an amino acid sequence capable of transmitting a co-stimulatory signal in an immune cell expressing the chimeric receptor upon binding of said extracellular domain to said ligand. Also provided are polynucleotides encoding same, cells expressing same and methods of use thereof.

16 Claims, 10 Drawing Sheets

Specification includes a Sequence Listing.

Anti S7

Anti S9

SIGLEC7

SIGLEC-BASED CHIMERIC POLYPEPTIDES AND USES THEREOF

RELATED APPLICATIONS

This application is a National Phase of PCT Patent Application No. PCT/IL2020/050445 having International filing date of Apr. 16, 2020, which claims the benefit of priority under 35 USC § 119(e) of U.S. Provisional Patent Application No. 62/834,995 filed on Apr. 17, 2019. The contents of the above applications are all incorporated by reference as if fully set forth herein in their entirety.

SEQUENCE LISTING STATEMENT

The ASCII file, entitled 89967SequenceListing.txt, created on Oct. 18, 2021, comprising 114,028 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to Siglec-based chimeric polypeptides and uses thereof.

Siglecs (Sialic acid-binding immunoglobulin-type lectins) are cell surface proteins that bind sialic acid, and more specifically sialic acid-containing carbohydrates (sialoglycans). There are 14 different mammalian Siglecs, providing an array of different functions based on cell surface receptor-ligand interactions. These receptor-glycan interactions can mediate, among other things, cell adhesion and cell signaling. Although sialic acid is ubiquitously expressed, typically at the terminal position of glycoproteins and lipids, only very specific, distinct sialoglycan structures are recognized by individual Siglecs, depending on identity and linkage to sub-terminal carbohydrate moieties.

Siglecs are Type I transmembrane proteins that contain an extracellular N-terminal V-type immunoglobulin-like domain (Ig-like domain) that acts as the binding receptor for sialic acid. All Siglecs extend from the cell surface by means of intervening C2-type Ig-like domains which have no binding activity. The cytoplasmic domains of most Siglecs contain immunoreceptor tyrosine-based inhibitory motifs (ITIMs), which recruit the tyrosine phosphatases, SHP1 and/or SHP2 thereby inhibit immune cell activation.

Upon malignant transformation, sialylation of cell surface glycoconjugates is frequently altered in tumor cells, resulting in the expression of sialylated tumor-associated carbohydrate antigens that are specific markers for the disease. As sialoglycans are involved in many biological processes, their expression by tumor cells has been shown to influence many crucial steps in tumor biology, including immune-editing, tumor growth and proliferation, invasion, metastasis, and angiogenesis (Kannagi R, et al. *Cancer Sci.* 2010; 101: 586-93). Over the years it has been observed that expression of sialic acids on cancer cells serves as a mechanism for evading the immune response elicited against the cancer. By this strategy, tumor cells might counter, for example, NK cell activation by interacting with the ITIM-containing Siglec receptors expressed on the NK cell (Jandus C, et al. *J. Clin. Invest* 2014; 124: 1810-20).

Consequently, direct targeting of cancer cells expressing siglecs or inhibiting siglecs' activity has been suggested for the treatment of cancer (e.g. Angata et al. (2015), TRENDS IN PHARMACOLOGICAL SCIENCES, 36, 10, 645-660; and International Patent Application Publication Nos: WO2018002640 and WO2017123745).

Additional background art includes International Patent Application Publication No: WO2016178996.

SUMMARY OF THE INVENTION

According to an aspect of some embodiments of the present invention there is provided a chimeric receptor comprising:

(a) an extracellular domain comprising an amino acid sequence of a Siglec-7 or a Siglec-9 receptor capable of binding a Siglec-7 and/or a Siglec-9 ligand and an Ig-like C2-type domain; and (b) an intracellular domain comprising an amino acid sequence capable of transmitting an activating signal and/or a co-stimulatory signal in an immune cell expressing the chimeric receptor upon binding of the extracellular domain to the ligand.

According to an aspect of some embodiments of the present invention there is provided a chimeric receptor comprising:

(a) an extracellular domain comprising an amino acid sequence of a Siglec-7 or a Siglec-9 receptor capable of binding a Siglec-7 and/or a Siglec-9 ligand; and (b) an intracellular domain comprising an amino acid sequence capable of transmitting a co-stimulatory signal in an immune cell expressing the chimeric receptor upon binding of the extracellular domain to the ligand, the intracellular domain being devoid of an amino acid sequence capable of transmitting an activating signal.

According to an aspect of some embodiments of the present invention there is provided a chimeric receptor comprising:

(a) an extracellular domain comprising an amino acid sequence of a Siglec-7 or a Siglec-9 receptor capable of binding a Siglec-7 and/or a Siglec-9 ligand;

(b) an intracellular domain comprising an amino acid sequence capable of transmitting an activating signal and/or a co-stimulatory signal in an immune cell expressing the chimeric receptor upon binding of the extracellular domain to the ligand; and (c) a transmembrane domain of CD28 or CD8a.

According to an aspect of some embodiments of the present invention there is provided a chimeric receptor comprising:

(a) an extracellular domain comprising an amino acid sequence of a Siglec-7 or a Siglec-9 receptor capable of binding a Siglec-7 and/or a Siglec-9 ligand;

(b) an intracellular domain comprising an amino acid sequence capable of transmitting an activating signal and/or a co-stimulatory signal in an immune cell expressing the chimeric receptor upon binding of the extracellular domain to the ligand; and (c) a transmembrane domain of CD28.

According to some embodiments of the invention, the extracellular domain comprises an Ig-like C2-type domain.

According to some embodiments of the invention, the Ig-like C2-type domain is of the Siglec-7 or the Siglec-9 receptor.

According to some embodiments of the invention, the Ig-like C2-type domain is located C-terminally to the amino acid sequence capable of binding the Siglec-7 and/or the Siglec-9 ligand.

According to some embodiments of the invention, the Ig-like C2-type domain is a single Ig-like C2-type domain.

According to some embodiments of the invention, the Ig-like C2-type domain is the third Ig-like domain located N to C in a full length Siglec-7 or Siglec-9 receptor.

According to some embodiments of the invention, an amino acid sequence of the Ig-like C2-type domain comprises an amino acid sequence having at least 80% identity to:

```
                                    (SEQ ID NO: 4)
    EGTASTALGNSSSLSVLEGQSLRLVCAVDSNPPAR

LSWTWRSLTLYPSQPSNPLVLELQVHLGDEGEFTC

RAQNSLGSQHVSLNLSLQQEY;
    or
                                    (SEQ ID NO: 8)
    DGTVSTVLGNGSSLSLPEGQSLRLVCAVDAVDSNP

PARLSLSWRGLTLCPSQPSNPGVLELPWVHLRDAA

EFTCRAQNPLGSQQVYLNVSLQSKA.
```

According to some embodiments of the invention, the amino acid sequence of the Ig-like C2-type domain comprises:

```
                                    (SEQ ID NO: 4)
    EGTASTALGNSSSLSVLEGQSLRLVCAVDSNPPAR

LSWTWRSLTLYPSQPSNPLVLELQVHLGDEGEFTC

RAQNSLGSQHVSLNLSLQQEY;
    or
                                    (SEQ ID NO: 8)
    DGTVSTVLGNGSSLSLPEGQSLRLVCAVDAVDSNP

PARLSLSWRGLTLCPSQPSNPGVLELPWVHLRDAA

EFTCRAQNPLGSQQVYLNVSLQSKA.
```

According to some embodiments of the invention, the extracellular domain is devoid of an Ig-like C2-type domain which is the second Ig-like domain located N to C in a full length Siglec-7 or Siglec-9 receptor.

According to some embodiments of the invention, the extracellular domain is devoid of an Ig-like C2-type domain comprising an amino acid sequence of:

```
                                    (SEQ ID NO: 3)
    HRPNILIPGTLESGCFQNLTCSVPWACEQGTPPMI

SWMGTSVSPLHPSTTRSSVLTLIPQPQHHGTSLTC

QVTLPGAGVTTNRTIQLNVS;
    or
                                    (SEQ ID NO: 7)
    HRPNILIPGTLESGCPQNLTCSVPWACEQGTPPMI

SWIGTSVSPLDPSTTRSSVLTLIPQPQDHGTSLTC

QVTFPGASVTTNKTVHLNVS.
```

According to some embodiments of the invention, the intracellular domain is devoid of an amino acid sequence capable of transmitting an activating signal.

According to some embodiments of the invention, the amino acid sequence capable of transmitting an activating signal comprises an amino acid sequence of CD3zeta and/or FcR gamma.

According to some embodiments of the invention, the amino acid sequence capable of transmitting a co-stimulatory signal comprises an amino acid sequence of 4-1BB, OX40, CD28, CD27, ICOS, CD40L, GITR, LIGHT, HVEM and/or CD30.

According to some embodiments of the invention, the chimeric receptor comprising a transmembrane domain of CD28.

According to some embodiments of the invention, the chimeric receptor comprising a transmembrane domain of CD8a.

According to some embodiments of the invention, the chimeric receptor comprising a transmembrane domain of a Siglec-7 or a Siglec-9 receptor.

According to some embodiments of the invention, the amino acid sequence capable of binding the Siglec-7 and/or the Siglec-9 ligand comprises an amino acid sequence having at least 80% identity to:

```
                                    (SEQ ID NO: 2)
    QKSNRKDYSLTMQSSVTVQEGMCVHVRCSFSYPVD

SQTDSDPVHGYWFRAGNDISWKAPVATNNPAWAVQ

EETRDRFHLLGDPQTKNCTLSIRDARMSDAGRYFF

RMEKGNIKWNYKYDQLSVNVTAL;
    or
                                    (SEQ ID NO: 6)
    GQTSKLLTMQSSVTVQEGLCVHVPCSFSYPSHGWI

YPGPVVHGYWFREGANTDQDAPVATNNPARAVWEE

TRDRFHLLGDPHTKNCTLSIRDARRSDAGRYFFRM

EKGSIKWNYKHHRLSVNVTAL.
```

According to some embodiments of the invention, the amino acid sequence capable of binding the Siglec-7 and/or the Siglec-9 ligand comprises:

```
                                    (SEQ ID NO: 2)
    QKSNRKDYSLTMQSSVTVQEGMCVHVRCSFSYPVD

SQTDSDPVHGYWFRAGNDISWKAPVATNNPAWAVQ

EETRDRFHLLGDPQTKNCTLSIRDARMSDAGRYFF

RMEKGNIKWNYKYDQLSVNVTAL;
    or
                                    (SEQ ID NO: 6)
    GQTSKLLTMQSSVTVQEGLCVHVPCSFSYPSHGWI

YPGPVVHGYWFREGANTDQDAPVATNNPARAVWEE

TRDRFHLLGDPHTKNCTLSIRDARRSDAGRYFFRM

EKGSIKWNYKHHRLSVNVTAL.
```

According to an aspect of some embodiments of the present invention there is provided a polynucleotide encoding the chimeric receptor.

According to an aspect of some embodiments of the present invention there is provided a host cell expressing the chimeric receptor.

According to some embodiments of the invention, the host cell being an immune cell.

According to some embodiments of the invention, the immune cell is a T cell.

According to some embodiments of the invention, the immune cell is an NK cell.

According to an aspect of some embodiments of the present invention there is provided an NK cell expressing a chimeric receptor comprising:

(a) an extracellular domain comprising an amino acid sequence of a Siglec-7 or a Siglec-9 receptor capable of binding a Siglec-7 and/or a Siglec-9 ligand; and (b) an intracellular domain comprising an amino acid sequence capable of transmitting an activating signal and/or a co-stimulatory signal in an immune cell expressing the chimeric receptor upon binding of the extracellular domain to the ligand.

According to some embodiments of the invention, the chimeric receptor is the chimeric receptor disclosed herein.

According to an aspect of some embodiments of the present invention there is provided a method of treating a disease associated with cells expressing a Siglec-7 and/or a Siglec-9 ligand in a subject in need thereof, the method comprising administering to the subject a therapeutically effective amount of the chimeric receptor, the polynucleotide or the cells, thereby treating the disease in the subject.

According to an aspect of some embodiments of the present invention there is provided the chimeric receptor, the polynucleotide or the cell, for use in the treatment of a disease associated with cells expressing the Siglec-7 and/or the Siglec-9 ligand.

According to some embodiments of the invention, the disease is cancer or an infection.

According to some embodiments of the invention, the cancer is selected form the group consisting of melanoma, hepatocellular cancer, pancreatic cancer, colon adenocarcinoma, cervical cancer, breast cancer, lung cancer lymphoma and leukaemia.

According to some embodiments of the invention, the cancer is selected form the group consisting of ovarian carcinoma, cervical cancer, pancreatic adenocarcinoma, leukaemia, melanoma, colon carcinoma, breast carcinoma and lung adenocarcinoma.

According to some embodiments of the invention, the infection is an HIV infection.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

(SIGL9_HUMAN); CD28: P10747 (CD28_HUMAN); and P20963 (CD3Z_HUMAN). EC: extracellular domain, TM: transmembrane domain, IC: intracellular domain.

Figure 2:
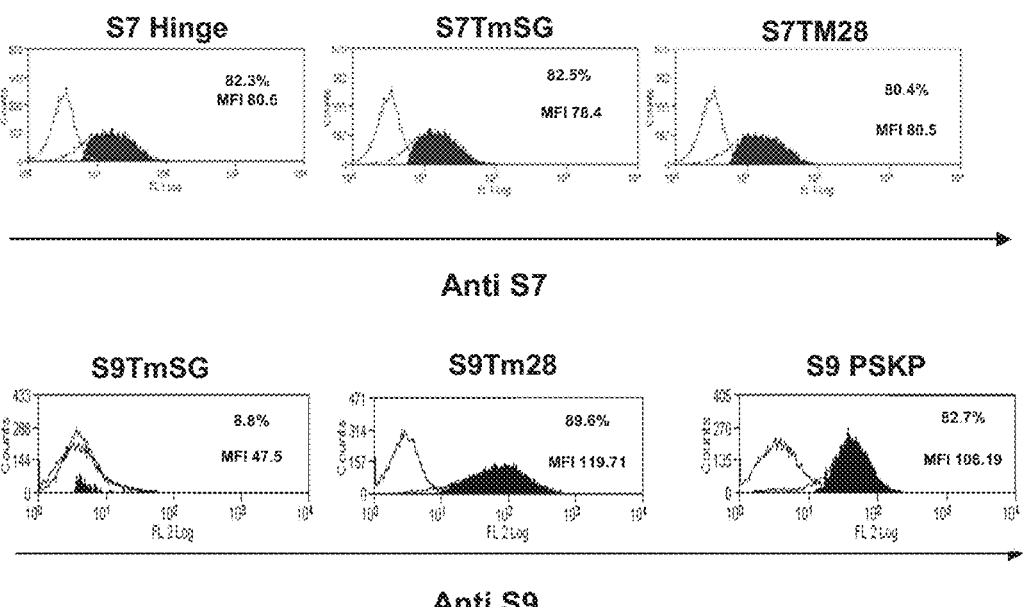

FIG. 2 shows flow cytometry analysis plots demonstrating electroporation efficiency of lymphocytes with the indicated Siglec-7/9 chimeric constructs. The percentage of positive cells and MFI (Mean Fluorescent Intensity) are indicated. The anti-fab staining of the non-electroporated control is shown as a white peak in each histogram. The results are representatives of 3 independent experiments performed with 3 different donors.

Figure 3:
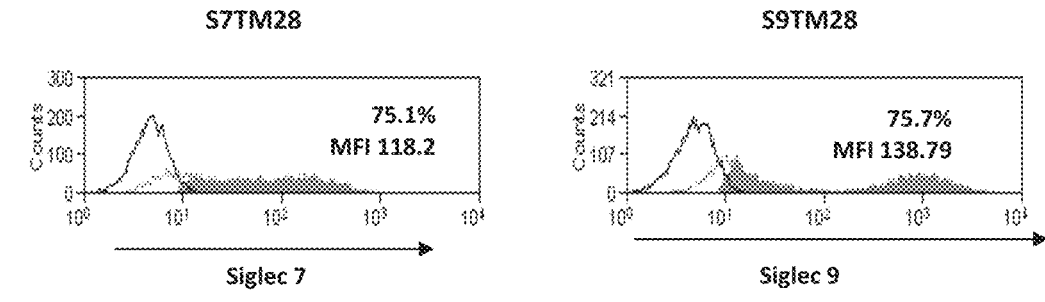

FIG. 3 shows flow cytometry analysis plots demonstrating expression of the Siglec-7/9 chimeric S7TM28 and S9TM28 constructs in transduced OKT3-stimulated human primary PBLs. The mock-transduced control is shown as a dotted line peak. The percentage of positive cells and the MFI are indicated.

Figure 4:
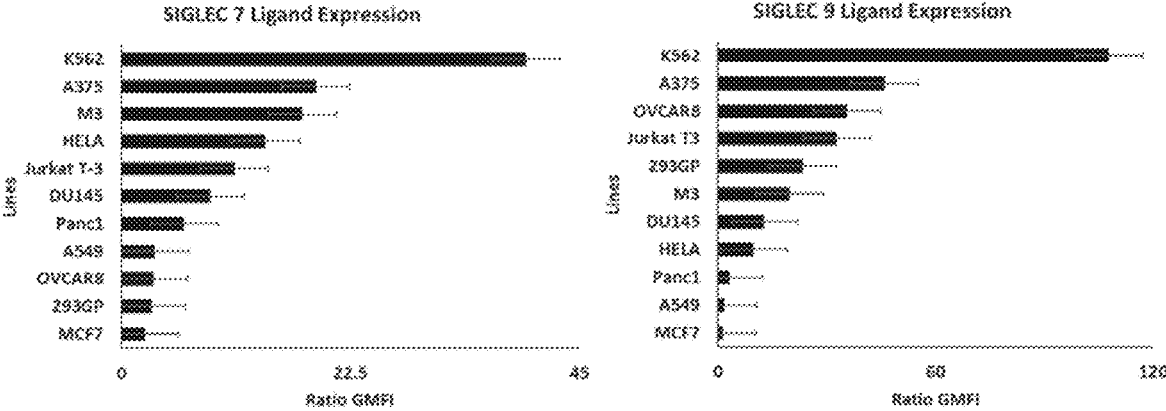

FIG. 4 demonstrates expression of Siglec-7/9 ligands in the indicated cell lines, as determined by flow cytometry. Results are shown as the MFI ratio of stained sample out of background staining.

Figure 5:
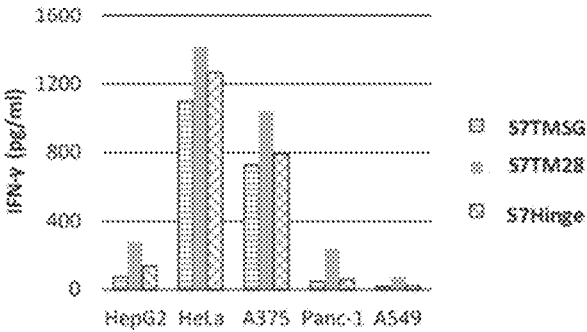
Figure 5:
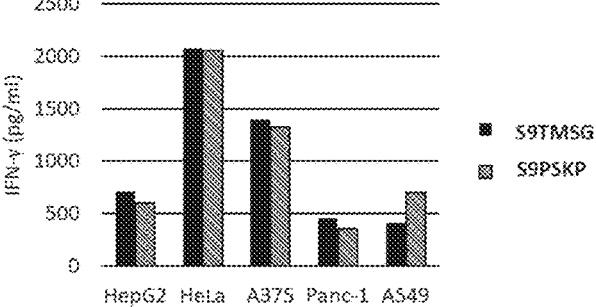

FIG. 5 shows graphs of IFNγ secretion by lymphocytes electroporated with the indicated Siglec-7/9 chimeric constructs following co-culture with the indicated cell lines, as determined by ELISA. The cell line A549 served as a negative control.

Figures 6, 7:
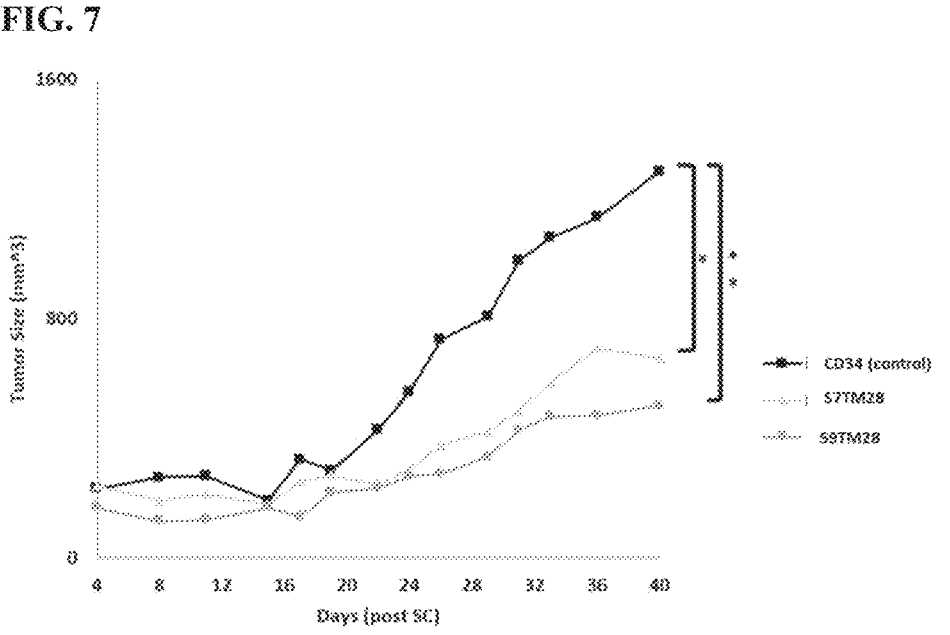

FIG. 6 shows graphs of IFNγ secretion by OKT3-stimulated human primary PBLs transduced with the indicated Siglec-7/9 chimeric constructs following co-culture with the indicated cell lines, as determined by ELISA. A truncated CD34 construct was used to transduce T-cells as a negative control. The results are representatives of 3 independent experiments.

FIG. 7 demonstrates the in-vivo anti-tumor effect of T cells transduced with Siglec-7/9 chimeric constructs. NSG-mice were inoculated 3 times with $5 \times 10^6$ T-cells transduced with S7TM28 and S9TM28 constructs and $2 \times 10^6$ K562 tumor cells in the upper flank (4 mice per group) in 200 μl Matrigel. Tumor growth was calculated as Dd^2*Pi/2.

Figure 8:
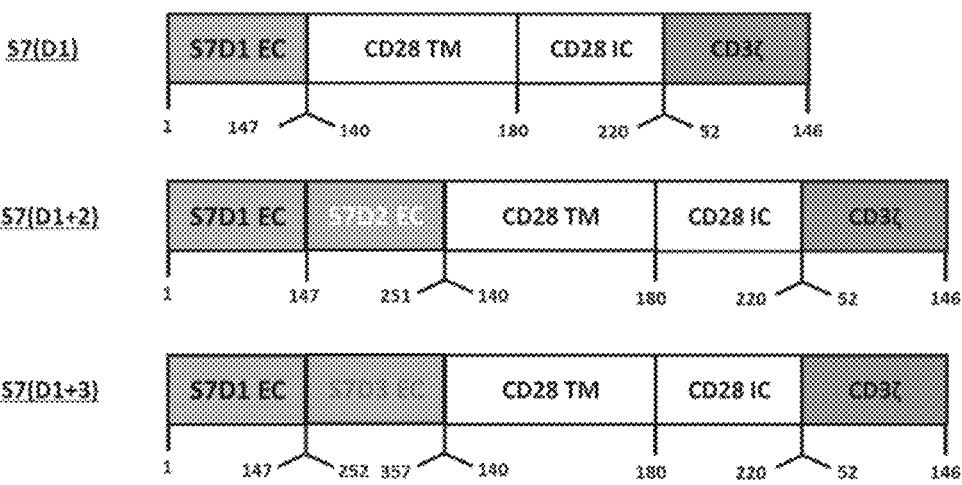

FIG. 8 is a schematic representation of Siglec-7/9 chimeric constructs encompassing different Siglec-7/9 domains in the extracellular part of the receptor. The numbering relates to the amino acids coordinates in the original protein (SIGLEC 7: Q9Y286 (SIGL7_HUMAN); SIGLEC 9: Q9Y336 (SIGL9_HUMAN); CD28: P10747 (CD28_HUMAN); and P20963 (CD3Z_HUMAN). EC: extracellular domain, TM: transmembrane domain, IC: intracellular domain.

Figure 9:
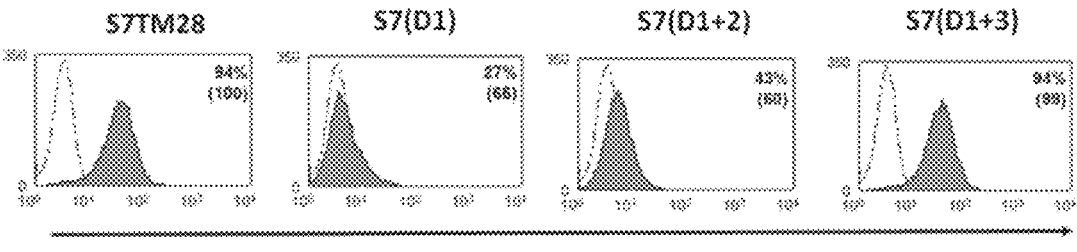

FIG. 9 shows flow cytometry analysis plots demonstrating expression of the indicated Siglec-7/9 chimeric constructs in transduced OKT3-stimulated human primary PBLs. The mock-transduced control is shown as a dotted line peak. The percentage of positive cells and the MFI (in brackets) are indicated.

Figure 10:
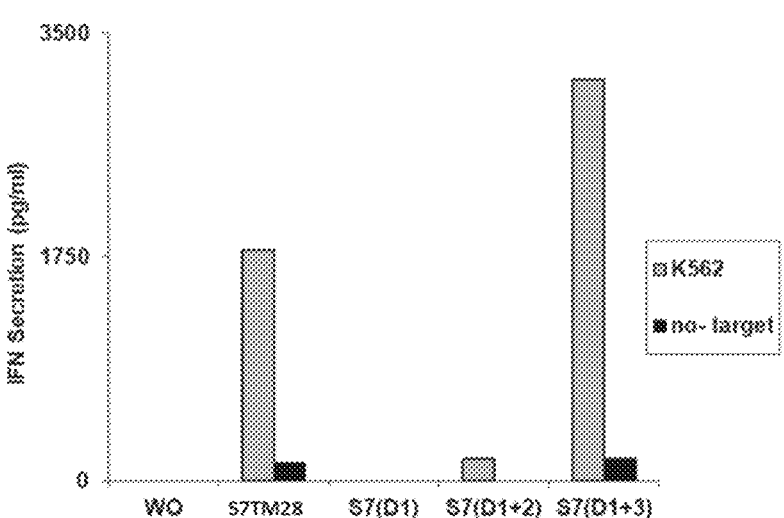

FIG. 10 is a graph of IFNγ secretion by OKT3-stimulated human primary PBLs transduced with the indicated Siglec-7/9 chimeric constructs following co-culture with K562 cells, as determined by ELISA.

Figure 11:
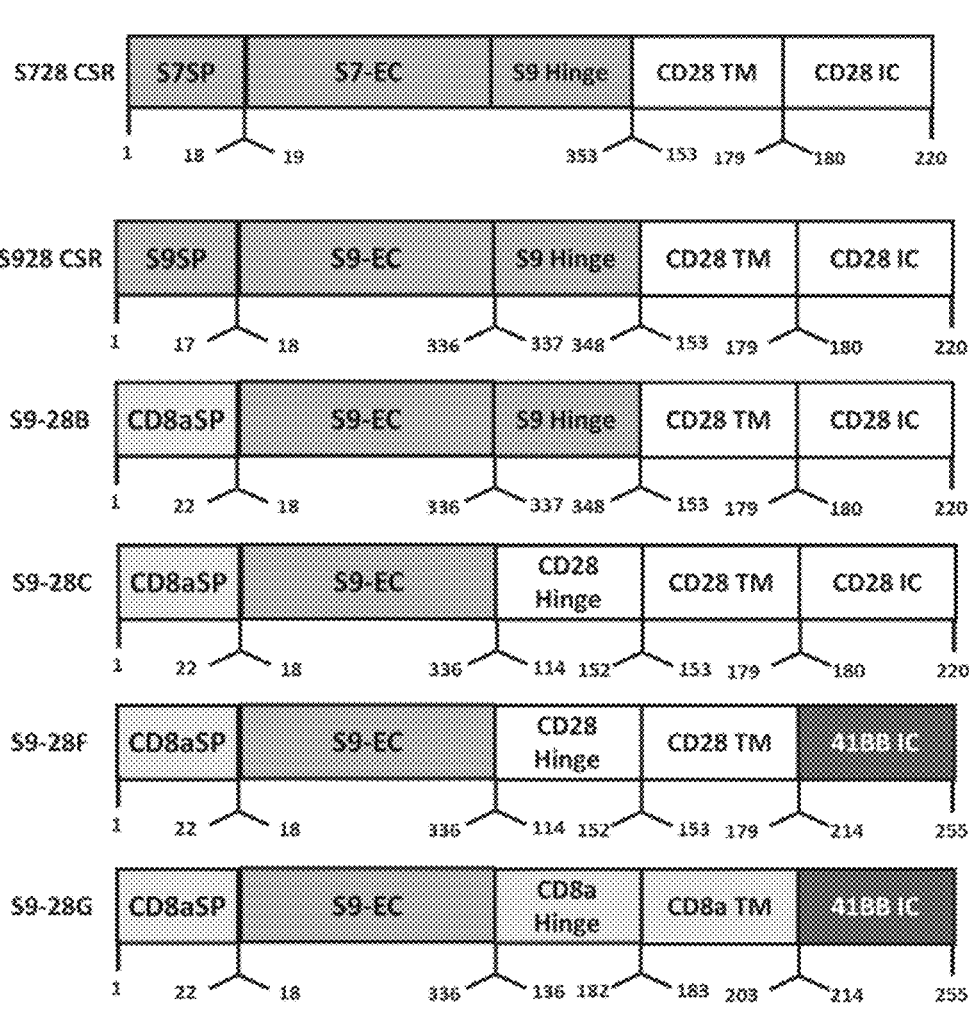

FIG. 11 is a schematic representation of different Siglec-7/9 chimeric Co-stimulatory switch receptors (CSR). The numbering relates to the amino acids coordinates in the original protein [SIGLEC 7: Q9Y286 (SIGL7_HUMAN); SIGLEC 9: Q9Y336 (SIGL9_HUMAN); CD28: P10747 (CD28_HUMAN); CD8a: P01732 (CD8A_HUMAN); 41BB Q07011 (TNR9_HUMAN); and P20963 (CD3Z_HUMAN)]. EC: extracellular domain, TM: transmembrane domain, IC: intracellular domain.

Figure 12:
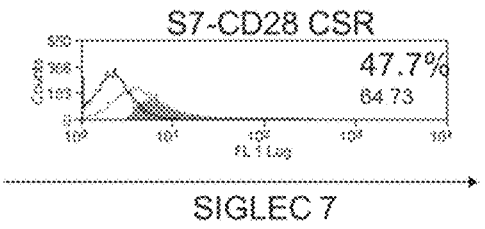
Figure 12:

FIG. 12 shows flow cytometry analysis plots demonstrating expression of the indicated Siglec-7/9 CSR constructs in transduced OKT3-stimulated human primary PBLs. The mock-transduced control is shown as a black line peak. The percentage of positive cells and the MFI are indicated.

Figure 13:
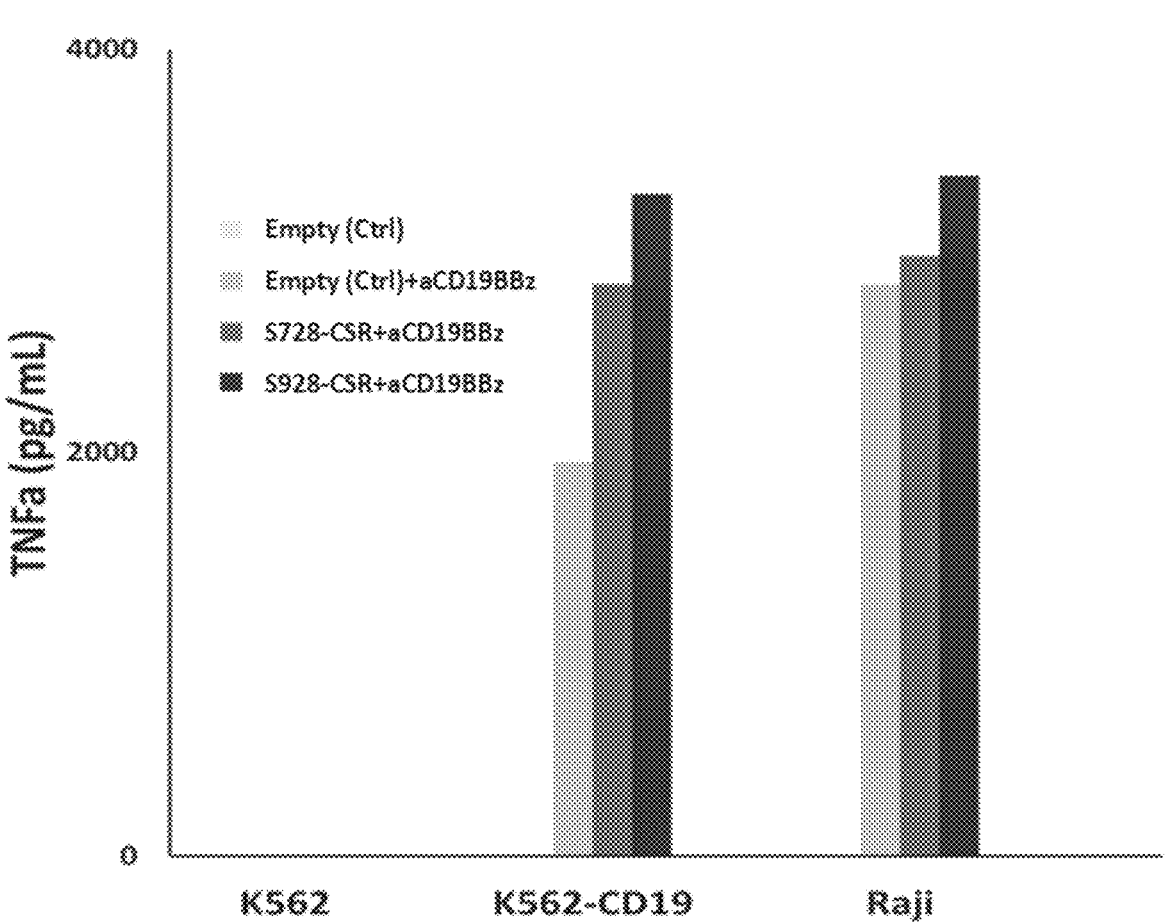

FIG. 13 is a graph of TNFα secretion by OKT3-stimulated human primary PBLs transduced with the indicated Siglec-7/9 CSR+CD19-specific 4-1BB CAR constructs following co-culture with K562/cd19 or Raji cells, as determined by ELISA. Co-culture with K562 cells served as a negative control.

Figure 14:
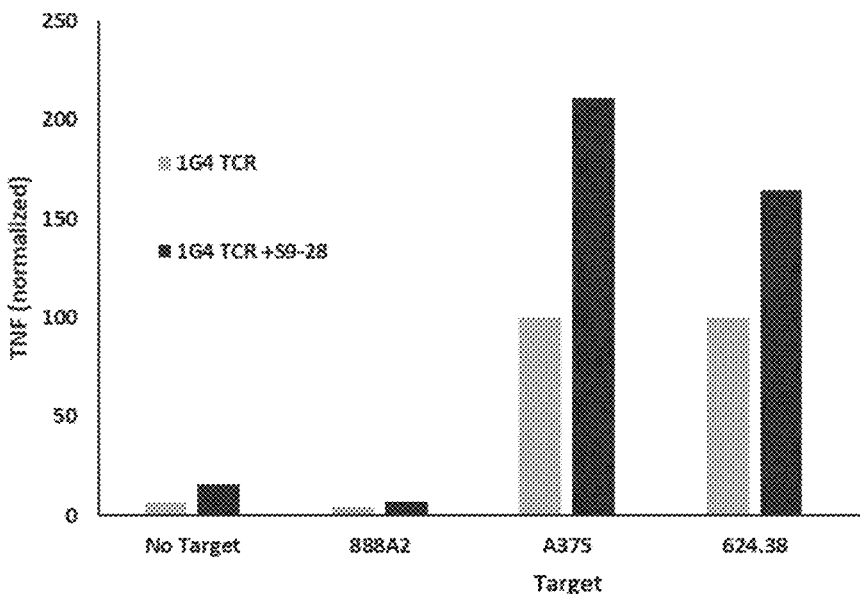

FIG. 14 is a graph of TNFα secretion by OKT3-stimulated human primary PBLs transduced with the indicated Siglec-9 CSR+NYESO1-specific 1G4 TCR constructs following co-culture with A375 and 624.38 cells, as determined by ELISA. Co-culture with 888A2 cells served as a negative control. The results were normalized to that obtained in the positive control—A375 with TCR 1G4 only.

Figure 15:
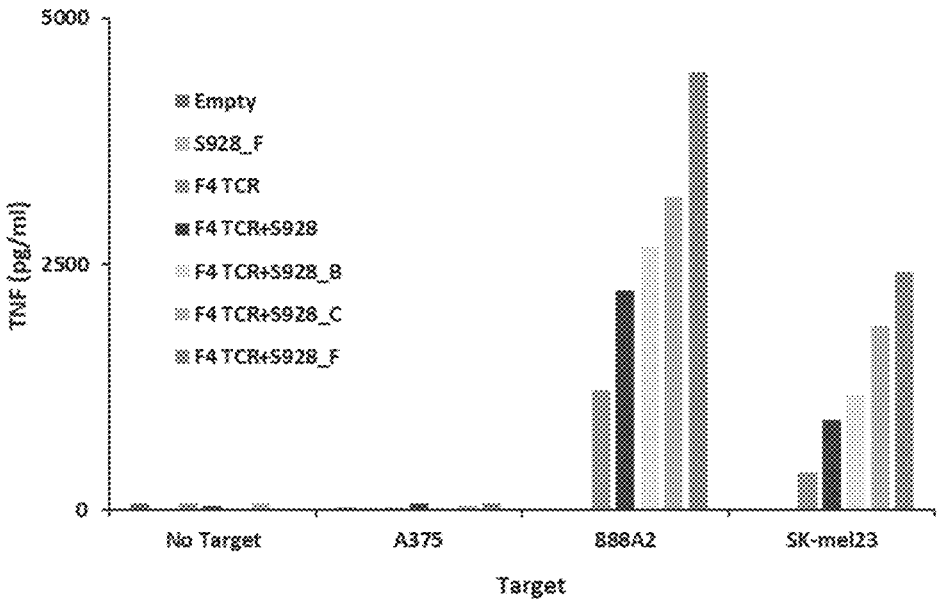

FIG. 15 is a graph of TNFα secretion by OKT3-stimulated human primary PBLs transduced with the indicated Siglec-9 CSRs+MART1-specific F4 TCR constructs following co-culture with 888A2 and SKMEL23 cells, as determined by ELISA. Co-culture with A375 cells served as a negative control.

Figure 16:
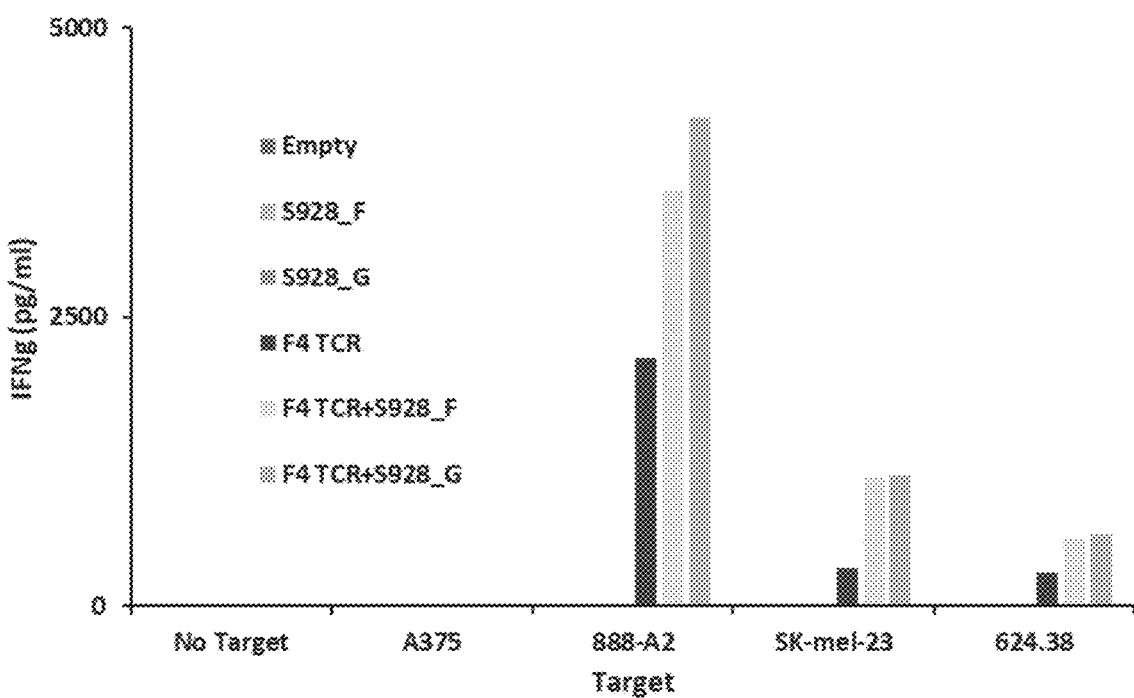

FIG. 16 is a graph of IFNγ secretion by OKT3-stimulated human primary PBLs transduced with the indicated Siglec-9 CSRs+MART1-specific F4 TCR constructs following co-culture with 888A2, 624.38 and SKMEL23 cells, as determined by ELISA. Co-culture with A375 cells served as a negative control.

DESCRIPTION OF SPECIFIC EMBODIMENTS OF THE INVENTION

The present invention, in some embodiments thereof, relates to Siglec-based chimeric polypeptides and uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Siglecs (Sialic acid-binding immunoglobulin-type lectins) are cell surface Type I transmembrane proteins that bind sialic acid, and more specifically sialic acid-containing carbohydrates (sialoglycans). Siglecs contain an extracellular N-terminal V-type immunoglobulin-like domain (Ig-like domain) that acts as the binding receptor for sialic acid. All Siglecs extend from the cell surface by means of intervening C2-type Ig-like domains which have no binding activity. The cytoplasmic domains of most Siglecs contain immunoreceptor tyrosine-based inhibitory motifs (ITIMs), which recruit the tyrosine phosphatases, SHP1 and/or SHP2 thereby inhibit immune cell activation.

Upon malignant transformation, sialylation of cell surface glycoconjugates is frequently altered in tumor cells, resulting in the expression of sialylated tumor-associated carbohydrate antigens that are specific markers for the disease. As sialoglycans are involved in many biological processes, their expression by tumor cells has been shown to influence many crucial steps in tumor biology. Over the years it has been observed that expression of sialic acids on cancer cells serves as a mechanism for evading the immune response elicited against the cancer. By this strategy, tumor cells might counter, for example, NK cell activation by interacting with the ITIM-containing Siglec receptors expressed on the NK cell (Jandus C, et al. *J. Clin. Invest* 2014; 124: 1810-20).

Whilst reducing specific embodiments of the present invention to practice, the present inventors designed and expressed several chimeric receptors comprising an extracellular domain of a Siglec-7 or a Siglec-9 receptor capable of binding a Siglec-7 and/or a Siglec-9 ligand and a signaling amino acid sequence capable of transmitting an activating signal (e.g. CD3 zeta) and/or a co-stimulatory signal (e.g. CD28, 4-1BB) (Examples 1-3 of the Examples section which follows). As is illustrated hereinunder and in the examples section, which follows, the present inventors further show that the generated chimeric receptors can be expressed in immune cells and induce in-vitro and in-vivo anti-tumor effects.

Consequently, specific embodiments of the present teachings suggest immune cells (e.g. T cells, NK cells) genetically engineered to express the chimeric receptor; and methods of using these immune cells to treat diseases associated with cells expressing a Siglec-7 and/or a Siglec-9 ligand (e.g. cancer).

Thus, according to an aspect of the present invention, there is provided a chimeric receptor comprising:

(a) an extracellular domain comprising an amino acid sequence of a Siglec-7 or a Siglec-9 receptor capable of binding a Siglec-7 and/or a Siglec-9 ligand; and (b) an intracellular domain comprising an amino acid sequence capable of transmitting a co-stimulatory signal in an immune cell expressing the chimeric receptor upon binding of said extracellular domain to said ligand, said intracellular domain being devoid of an amino acid sequence capable of transmitting an activating signal.

According to an additional or an alternative aspect of the present invention, there is provided a chimeric receptor comprising:

(a) an extracellular domain comprising an amino acid sequence of a Siglec-7 or a Siglec-9 receptor capable of binding a Siglec-7 and/or a Siglec-9 ligand and an Ig-like C2-type domain; and (b) an intracellular domain comprising an amino acid sequence capable of transmitting an activating signal and/or a co-stimulatory signal in an immune cell expressing the chimeric receptor upon binding of said extracellular domain to said ligand.

According to an additional or an alternative aspect of the present invention, there is provided a chimeric receptor comprising:

(a) an extracellular domain comprising an amino acid sequence of a Siglec-7 or a Siglec-9 receptor capable of binding a Siglec-7 and/or a Siglec-9 ligand;

(b) an intracellular domain comprising an amino acid sequence capable of transmitting an activating signal and/or a co-stimulatory signal in an immune cell expressing the chimeric receptor upon binding of said extracellular domain to said ligand; and (c) a transmembrane domain of CD28 or CD8a.

According to an additional or an alternative aspect of the present invention, there is provided a chimeric receptor comprising:

(a) an extracellular domain comprising an amino acid sequence of a Siglec-7 or a Siglec-9 receptor capable of binding a Siglec-7 and/or a Siglec-9 ligand;

(b) an intracellular domain comprising an amino acid sequence capable of transmitting an activating signal and/or a co-stimulatory signal in an immune cell expressing the chimeric receptor upon binding of said extracellular domain to said ligand; and (c) a transmembrane domain of CD28.

The term "receptor", hereinafter also referred to as "a polypeptide", comprises an extracellular binding domain, a transmembrane domain and an intracellular signalling domain.

As used herein, the terms "polypeptide" and "peptide", which are interchangeably used herein, encompass native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein.

As used herein, the term "chimeric receptor" or "chimeric polypeptide", also known as fusion receptor, refers to a receptor comprising an amino acid sequence having two or more parts which are not found together as a dingle protein expression product in nature.

The chimeric receptor disclosed herein comprises at least an extracellular domain comprising an amino acid sequence capable of binding a Siglec-7 and/or a Siglec-9 ligand and a heterologous intracellular signaling amino acid sequence.

As used herein, the term "heterologous" refers to an amino acid sequence which is not native to the recited amino acid sequence (e.g. an amino acid sequence capable of binding a Siglec-7 and/or a Siglec-9 ligand) at least in localization or is completely absent from the native sequence of the recited amino acid sequence.

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

A used herein, the phrase "an amino acid sequence of a Siglec-7 or a Siglec-9 receptor capable of binding a Siglec-7 and/or a Siglec-9 ligand" refers to a fragment of a Siglec-7 of a Siglec-9 receptor which comprises an extracellular domain of Siglec-7 of a Siglec-9 receptor capable of binding a Siglec-7 and/or a Siglec-9 ligand. Assays for testing binding are well known in the art and include, but not limited to flow cytometry, BiaCore, bio-layer interferometry Blitz® assay, HPLC, surface plasmon resonance.

According to specific embodiments, the Siglec-7 or a Siglec-9 receptor capable of binding a Siglec-7 and/or a Siglec-9 ligand binds the Siglec-7 and/or a Siglec-9 ligand with a Kd $\geq 10^{-5}$, $10^{-4}$ or $10^{-3}$.

According to specific embodiments, the Siglec-7 or a Siglec-9 receptor capable of binding a Siglec-7 and/or a Siglec-9 ligand binds the Siglec-7 and/or a Siglec-9 ligand with a Kd of $10^{-3}$-$10^{-4}$ M.

As used herein, the term "Siglec-7 receptor", also known as CD328, refers to the polypeptide expression product of the SIGLEC7 gene (Gene ID 27036). According to specific embodiments, Siglec-7 is the human Siglec-7, such as provided in the following Accession Nos. NP_055200, NP_001264130, NP_057627.

Siglec-7 ligands include, but are not limited to, alpha-2,8-, alpha-2,6 and alpha-2,3-linked sialic acid, disialoganglio-sides (disialogalactosyl globoside, disialyl lactotetraosylceramide, disialyl GalNAc lactotetraoslylceramide), disialyl Lewis-a and sialyl 6-sulfo Lewis-x.

The term "Siglec-7" also encompasses functional homo-logues (naturally occurring or synthetically/recombinantly produced), which exhibit the desired activity (i.e., binding a Siglec-7 ligand). Such homologues can be, for example, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide provided in Accession No. NP_055200 (SEQ ID NO: 1), NP_001264130, or NP_057627; or at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same.

Sequence identity or homology can be determined using any protein or nucleic acid sequence alignment algorithm such as Blast, ClustalW, and MUSCLE.

The homolog may also refer to an ortholog, a deletion, insertion, or substitution variant, including a conservative and non-conservative amino acid substitution, as further described hereinbelow.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions, the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH[(—CH$_2$)$_5$—COOH]—CO— for aspartic acid. Those non-conservative substitutions which fall under the scope of the present invention are those which still constitute an amino acid sequence capable of binding an anti-CD3 antibody.

According to specific embodiments, the amino acid sequence of Siglec-7 receptor capable of binding a Siglec-7 and/or a Siglec-9 ligand comprises an Ig-like V-type domain (InterPro database entry IPRO13106, Pfam database entry PF07686).

According to specific embodiments, the amino acid sequence of Siglec-7 receptor capable of binding a Siglec-7 and/or a Siglec-9 ligand comprises an amino acid sequence having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to

```
                                  (SEQ ID NO: 2)
QKSNRKDYSLTMQSSVTVQEGMCVHVRCSFSYPVD

SQTDSDPVHGYWFRAGNDISWKAPVATNNPAWAVQ

EETRDRFHLLGDPQTKNCTLSIRDARMSDAGRYFF

RMEKGNIKWNYKYDQLSVNVTAL
```

According to specific embodiments, the amino acid sequence of Siglec-7 receptor capable of binding a Siglec-7 and/or a Siglec-9 ligand comprises an amino acid sequence having at least 80% identity to SEQ ID NO: 2.

According to specific embodiments, the amino acid sequence of Siglec-7 receptor capable of binding a Siglec-7 and/or a Siglec-9 ligand comprises SEQ ID NO: 2.

According to specific embodiments, the amino acid sequence of Siglec-7 receptor capable of binding a Siglec-7 and/or a Siglec-9 ligand consists of SEQ ID NO: 2.

As used herein, the term "Siglec-9 receptor", also known as CD329, refers to the polypeptide expression product of the SIGLEC9 gene (Gene ID 27180). According to specific embodiments, Siglec-7 is the human Siglec-7, such as provided in the following Accession Nos. NP_001185487, NP_055256.

Siglec-9 ligands include, but are not limited to, sialic acid in either the alpha-2,3- or alpha-2,6-linked sialic acid, MUC16, vascular adhesion protein 1 (VAP-1), MUC1.

The term "Siglec-9" also encompasses functional homologues (naturally occurring or synthetically/recombinantly produced), which exhibit the desired activity (i.e., binding a Siglec-7 ligand). Such homologues can be, for example, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide provided in Accession No. NP_001185487 or NP_055256; or at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same.

According to specific embodiments, the amino acid sequence of Siglec-9 receptor capable of binding a Siglec-7 and/or a Siglec-9 ligand comprises an Ig-like V-type domain (InterPro database entry IPR013106, Pfam database entry PF07686).

According to specific embodiments, the amino acid sequence of Siglec-9 receptor capable of binding a Siglec-7 and/or a Siglec-9 ligand comprises an amino acid sequence having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to

```
                                  (SEQ ID NO: 6)
GQTSKLLTMQSSVTVQEGLCVHVPCSFSYPSHGWI

YPGPVVHGYWFREGANTDQDAPVATNNPARAVWEE

TRDRFHLLGDPHTKNCTLSIRDARRSDAGRYFFRM

EKGSIKWNYKHHRLSVNVTAL.
```

According to specific embodiments, the amino acid sequence of Siglec-9 receptor capable of binding a Siglec-7 and/or a Siglec-9 ligand comprises an amino acid sequence having at least 80% identity to SEQ ID NO: 6.

According to specific embodiments, the amino acid sequence of Siglec-9 receptor capable of binding a Siglec-7 and/or a Siglec-9 ligand comprises SEQ ID NO: 6.

According to specific embodiments, the amino acid sequence of Siglec-9 receptor capable of binding a Siglec-7 and/or a Siglec-9 ligand consists of SEQ ID NO: 6.

According to specific embodiments, the extracellular domain comprises an Ig-like C2-type domain.

The Ig-like C2-type domain may be located C-terminally or N-terminally to the amino acid sequence capable of binding the Siglec-7 and/or the Siglec-9 ligand.

According to specific embodiments, the Ig-like C2-type domain is located C-terminally to the amino acid sequence capable of binding the Siglec-7 and/or the Siglec-9 ligand.

As used herein the phrase "Ig-like C2-type domain" refers to an amino acid sequence which comprises a protein motif as set forth in InterPro database entry IPR008424 or Pfam database entry PF05790.

According to specific embodiments, the Ig-like C2-type domain is of a Siglec-7 or a Siglec-9 receptor.

According to specific embodiments, the Ig-like C2-type domain has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to the Ig-like C2-type domain of a Siglec-7 or a Siglec-9 receptor.

As Siglec 7 and Siglec 9 receptors comprises two Ig-like C2-type domains, the extracellular domain may comprise an amino acid sequence of one of the Ig-like C2-type domains or of the two Ig-like C2-type domains.

According to specific embodiments, the extracellular domain comprises an amino acid sequence of only one of the Siglec 7 or Siglec 9 receptor Ig-like C2-type domains.

According to specific embodiments, the extracellular domain of the chimeric receptor comprises a single Ig-like C2-type domain.

According to specific embodiments, the Ig-like C2-type domain is the third Ig-like domain located N to C in a full length Siglec-7 or Siglec-9 receptor.

According to specific embodiments, the Ig-like C2-type domain has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to the third Ig-like domain located N to C in a full length Siglec-7 or Siglec-9 receptor.

According to specific embodiments, the Ig-like C2-type domain corresponds to amino acids coordinates 251-336 of NP_055200 (SEQ ID NO: 1).

According to specific embodiments, the Ig-like C2-type domain corresponds to amino acids coordinates 247-341 of NP_001185487 (SEQ ID NO: 5).

According to specific embodiments, the amino acid sequence of the Ig-like C2-type domain comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 4 or 8.

According to specific embodiments, the amino acid sequence of the Ig-like C2-type domain comprises an amino acid sequence having at least 80% identity to SEQ ID NO: 4 or 8.

According to specific embodiments, the amino acid sequence of the Ig-like C2-type domain comprises SEQ ID NO: 4 or 8.

According to specific embodiments, the amino acid sequence of the Ig-like C2-type domain consists of SEQ ID NO: 4 or 8.

According to specific embodiments, the amino acid sequence of the Ig-like C2-type domain is at least 60, at least 65, at least 70, at least 75, at least 80, at least 85, at least 90 or at least 91 amino acids in length, each possibility represents a separate embodiment of the present invention.

According to specific embodiments, the Ig-like C2-type domain is not the Ig-like C2-type domain which is the second Ig-like domain located N to C in a full length Siglec-7 or Siglec-9 receptor.

According to specific embodiments, the Ig-like C2-type domain is not the Ig-like C2-type domain corresponding to amino acid coordinates 144-233 of NP_055200 (SEQ ID NO: 1) or amino acid coordinates 144-233 of NP_001185487 (SEQ ID NO: 5).

According to specific embodiments, the Ig-like C2-type domain is not the Ig-like C2-type domain comprising SEQ ID NO: 3 or 7.

According to specific embodiments, the extracellular domain of the chimeric receptor is devoid of an Ig-like C2-type domain which is the second Ig-like domain located N to C in a full length Siglec-7 or Siglec-9 receptor.

According to specific embodiments, the extracellular domain of the chimeric receptor is devoid of an Ig-like C2-type domain corresponding to amino acid coordinates 144-233 of NP_055200 (SEQ ID NO: 1) or amino acid coordinates 144-233 of NP_001185487 (SEQ ID NO: 5).

According to specific embodiments, the extracellular domain of the chimeric receptor is devoid of an Ig-like C2-type domain comprising an amino acid sequence of SEQ ID NO: 3 or 7. As noted, the chimeric receptor disclosed herein comprises an intracellular domain comprising an amino acid sequence capable of transmitting an activating and/or a co-stimulatory signal upon binding of the extracellular domain to the ligand.

According to specific embodiments, the chimeric receptor comprises a co-stimulatory signal amino acid sequence and is devoid of an activating amino acid sequence.

As used herein the phrase "activating signal" refers to an amino acid sequence capable of transmitting a primary stimulatory signal resulting in cellular proliferation, maturation, cytokine production and/or induction of regulatory or effector functions. Typically, an activating signal domain comprises an ITAM domain.

Any known activating signal domain can be used with specific embodiments of the present invention. Non-limiting examples of activating signaling domains include the signaling domains of CD3zeta, FcR gamma, FcR beta, CD3 gamma, CD3 delta, CD3 epsilon, CD5, CD22, CD79a, CD79b, and CD66d.

According to specific embodiments, the amino acid sequence capable of transmitting an activating signal comprises an amino acid sequence of CD3zeta.

As used herein the term "CD3zeta" also known as TCRzeta or CD247 refers to the polypeptide expression product of the CD247 gene (Gene ID 919). According to a specific embodiment, the CD3zeta protein refers to the human protein, such as provided in the following GenBank Numbers NP_000725 and/or NP_932170.

According to specific embodiments, the amino acid sequence of CD3zeta comprises SEQ ID NO: 24.

According to specific embodiments, the amino acid sequence capable of transmitting an activating signal comprises an amino acid sequence of FcR gamma.

As used herein the phrase "FcR gamma" refers to the polypeptide expression product of the FCER1G gene (Gene ID 2207). According to specific embodiments, FcR gamma protein refers to the human protein, such as provided in the following GenBank Number NP_004097.

Methods of determining signaling of a stimulatory signal are well known in the art, and include, but are not limited to, enzymatic activity assays such as kinase activity assays, and expression of molecules involved in the signaling cascade using e.g. PCR, Western blot, immunoprecipation and immunohistochemistry. Additionally or alternatively, determining transmission of an activating signal can be effected by evaluating T cell activation or function. Methods of evaluating T cell activation or function are well known in the art and include, but are not limited to, proliferation assays such as CFSE staining, MTT, Alamar blue, BRDU and thymidine incorporation, cytotoxicity assays such as CFSE staining, chromium release, Calcin AM, cytokine secretion assays such as intracellular cytokine staining, ELISPOT and ELISA, expression of activation markers such as CD25, CD69, CD137, CD107a, PD1, and CD62L using flow cytometry.

According to a specific embodiment, the intracellular domain of the chimeric receptor is devoid of an amino acid sequence capable of transmitting an activating signal.

According to a specific embodiment, the intracellular domain of the chimeric receptor is devoid of an ITAM domain.

According to a specific embodiment, the intracellular domain of the chimeric receptor is devoid of CD3zeta signalling domain.

As used herein, the phrase "co-stimulatory signal" refers to an amino acid sequence of a co-stimulatory molecule capable of transmitting a secondary stimulatory signal resulting in activation of the T cell. Typically, a co-stimulatory signal domain does not comprise an ITAM domain. Non-limiting examples of co-stimulatory signal domains include YXXM (SEQ ID NO: 51) e.g. YMNM (SEQ ID NO: 52, PRRP (SEQ ID NO: 53)/PYAP (SEQ ID NO: 54)/YRS, YVN, QEED (SEQ ID NO: 55)/EEEE (SEQ ID NO: 56), TPIQEE (SEQ ID NO: 57)/EEGKE (SEQ ID NO: 58), VTTVEVEET (SEQ ID NO: 59), PIQED (SEQ ID NO: 60).

Any known co-stimulatory signal domain can be used with specific embodiments of the present invention. Non-limiting examples of co-stimulatory signal domains include the signaling domains of 4-1BB, CD28, OX40, ICOS, CD27, GITR, HVEM, TIM1, LFA1(CD11a), CD2, CD40L, LIGHT, CD30, DNAM.

According to specific embodiments, the amino acid sequence capable of transmitting a co-stimulatory signal comprises an amino acid sequence of 4-1BB, OX40, CD28, CD27, ICOS, CD40L, GITR, LIGHT, HVEM and/or CD30.

According to specific embodiments, the amino acid sequence capable of transmitting a co-stimulatory signal comprises an amino acid sequence of CD28. As used herein the term "CD28" refers to the polypeptide of the CD28 gene (Gene ID 940). According to a specific embodiment, the CD28 protein refers to the human protein, such as provided in the following GenBank Number NP_001230006, NP_001230007, NP_006130.

According to specific embodiments, the co-stimulatory signal amino acid sequence of CD28 comprises SEQ ID NO: 25.

According to specific embodiments, the amino acid sequence capable of transmitting a co-stimulatory signal comprises an amino acid sequence of 4-1BB.

As used herein the term "4-1BB (also known as CD137 and TNFRSF9)" refers to the polypeptide of the TNFRSF9 gene (Gene ID 3604). According to a specific embodiment, the 4-1BB protein refers to the human protein, such as provided in the following GenBank Number NP_001552.

According to specific embodiments, the co-stimulatory signal amino acid sequence of 4-1BB comprises SEQ ID NO: 26.

The chimeric receptor disclosed herein further comprises a hinge domain and/or a transmembrane domain.

The hinge domain and/or the transmembrane domain of any transmembrane receptor may be used with specific embodiments of the invention. According to specific embodiments, the chimeric receptor comprises a hinge domain and/or a transmembrane domain of a protein selected from the group consisting of Siglec 7, Siglec 9, CD28 and CD8.

According to a specific embodiment, the chimeric receptor comprises a hinge domain and/or a transmembrane domain of CD28.

According to specific embodiments, the transmembrane domain of CD28 comprises SEQ ID NO: 27.

According to specific embodiments, the hinge domain of CD28 comprises SEQ ID NO: 28.

According to a specific embodiment, the chimeric receptor comprises a hinge domain and/or a transmembrane domain of Siglec-7.

According to specific embodiments, the transmembrane domain of Siglec-7 comprises SEQ ID NO: 29.

According to specific embodiments, the hinge domain of Siglec-7 comprises SEQ ID NO: 30 or 31.

According to a specific embodiment, the chimeric receptor comprises a hinge domain and/or a transmembrane domain of Siglec-9.

According to specific embodiments, the transmembrane domain of Siglec-9 comprises SEQ ID NO: 32.

According to specific embodiments, the hinge domain of Siglec-9 comprises SEQ ID NO: 33.

According to specific embodiments, the chimeric receptor comprises a hinge domain and/or a transmembrane domain of a CD8.

As used herein the term "CD8" refers to the polypeptide of the CD8A or CD8B gene (Gene ID 925 or 926). According to a specific embodiment, the CD8 protein refers to the human CD8a protein, such as provided in the following GenBank Number NP_001139345, NP_001759, NP_741969. According to a specific embodiment, the CD8 protein refers to the human CD8b protein, such as provided in the following GenBank Number NP_742099, NP_004922, NP_757362, NP_001171571, NP_742100.

According to specific embodiments, the chimeric receptor comprises a hinge domain and/or a transmembrane domain of a CD8a.

According to specific embodiments, the transmembrane domain of CD8a comprises SEQ ID NO: 35

According to specific embodiments, the hinge domain of CD8a comprises SEQ ID NO: 34.

The components of the chimeric receptor described herein may be linked to each other directly or via a linker. Any linker known in the art can be used with specific embodiments of the invention. According to specific embodiments, the linker may be derived from naturally-occurring multi-domain proteins or is an empirical linker as described, for example, in Chichili et al., (2013), Protein Sci. 22(2): 153-167, Chen et al, (2013), Adv Drug Deliv Rev. 65(10): 1357-1369, the entire contents of which are hereby incorporated by reference. In some embodiments, the linker may be designed using linker designing databases and computer programs such as those described in Chen et al., (2013), Adv Drug Deliv Rev. 65(10): 1357-1369 and Crasto et al., (2000), Protein Eng. 13(5):309-312, the entire contents of which are hereby incorporated by reference.

According to specific embodiments, the linker is a synthetic linker.

According to specific embodiments, the linker is a polypeptide.

Non-limiting examples of linkers that can be used include AS, GS, (GGGGS)$_n$ (n=1-4) (SEQ ID NO: 62), GGGGSGGGG (SEQ ID NO: 32), (Gly)$_8$, (Gly)$_6$, (EAAAK)$_n$ (n=1-3) (SEQ ID NO: 63), PAPAP (SEQ ID NO: 64).

According to a specific embodiment, the components of the chimeric receptor described herein are directly linked to each other without any linker.

According to a specific embodiment, the components of the chimeric receptor described herein are linked to each via a short linker such as AS or GS.

According to specific embodiments, the chimeric receptor comprises an amino acid sequence selected from the group consisting of SEQ ID NO: 9-23, each possibility represents a separate embodiment of the present invention.

According to specific embodiments, the chimeric receptor comprises an amino acid sequence selected from the group consisting of SEQ ID NO: 7 and 12.

According to specific embodiments, the chimeric receptor comprises SEQ ID NO: 17.

According to specific embodiments, the chimeric receptor comprises an amino acid sequence selected from the group consisting of SEQ ID NO: 18-23, each possibility represents a separate embodiment of the present invention.

According to specific embodiments, the chimeric receptor may further comprise a detectable tag. Non-limiting examples of detectable tags include chitin binding protein (CBP)-tag, maltose binding protein (MBP)-tag, glutathione-S-transferase (GST)-tag, poly(His)-tag, FLAG tag, Epitope tags, such as, V5-tag, c-myc-tag, and HA-tag, and fluorescence tags such as green fluorescent protein (GFP), red fluorescent protein (RFP), yellow fluorescent protein (YFP), blue fluorescent protein (BFP), and cyan fluorescent protein (CFP); as well as derivatives of these tags, or any tag known in the art.

The receptors of some embodiments of the invention may be synthesized and purified by any techniques that are known to those skilled in the art of peptide synthesis, such as, but not limited to, solid phase and recombinant techniques.

According to specific embodiments, production of the polypeptide involves solid phase synthesis.

For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

According to specific embodiments, the polypeptide is produced by recombinant DNA technology.

Thus, according to an aspect of the present invention, there is provided a polynucleotide encoding the chimeric receptor.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

A non-limiting example of a polynucleotide encoding the chimeric receptor of some embodiments of the invention is provided in SEQ ID NO: 36-50, each possibility represents a separate embodiment of the present invention.

To express any of the disclosed polypeptides in a cell, a polynucleotide sequence encoding the polypeptide is preferably ligated into a nucleic acid construct suitable for cell expression. Such a nucleic acid construct includes a promoter sequence for directing transcription of the polynucleotide sequence in the cell in a constitutive or inducible manner.

The nucleic acid construct (also referred to herein as an "expression vector") of some embodiments of the invention includes additional sequences which render this vector suitable for replication and integration (e.g., shuttle vectors). In addition, a typical cloning vector may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes or encodes a signal sequence for targeting the polypeptide to the cell surface. According to a specific embodiment, the signal sequence for this purpose is a mammalian signal sequence or the signal sequence of the polypeptide variants of some embodiments of the invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed, i.e. T cells. Examples of T cell specific promoters include lymphoid specific promoters [Calame et al., (1988) Adv. Immunol. 43:235-275]; in particular promoters of T-cell receptors [Winoto et al., (1989) EMBO J. 8:729-733].

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long-term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) or a self-cleavable peptide; and sequences for genomic integration of the promoter-chimeric polypeptide.

It will be appreciated that the individual elements comprised in the expression vector can be arranged in a variety of configurations. For example, enhancer elements, promoters and the like, and even the polynucleotide sequence(s) encoding the polypeptide can be arranged in a "head-to-tail" configuration, may be present as an inverted complement, or in a complementary configuration, as an anti-parallel strand. While such variety of configuration is more likely to occur with non-coding elements of the expression vector, alternative configurations of the coding sequence within the expression vector are also envisioned.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A⁺, pMT010/A⁺, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The ability to select suitable vectors for transforming immune cells (e.g. T cells, NK cells) is well within the capabilities of the ordinary skilled artisan and as such no general description of selection consideration is provided herein.

Recombinant viral vectors are useful for in vivo expression of the polypeptides since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of some embodiments of the invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for targeting the polypeptide to the desired site in a cell. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Specific embodiments of the present invention also contemplates cells comprising the chimeric polypeptide described herein and method of generating same.

Thus, according to an aspect of the present invention, there is provided a host cell expressing the polypeptide or the polynucleotide encoding same.

According to an additional or an alternative aspect of the present invention, there is provided a method of expressing a chimeric receptor in a cell, the method comprising introducing into a cell the polynucleotide encoding the chimeric receptor, under conditions which allow expression of the chimeric receptor.

Such conditions may be for example an appropriate temperature (e.g., 37° C.), atmosphere (e.g., air plus 5% $CO_2$), pH, light, medium, supplements and the like.

According to other specific embodiments, the introducing is effected in-vivo.

According to specific embodiments, the introducing is effected in-vitro or ex-vivo.

According to specific embodiments, the cell is a human cell.

According to specific embodiments, the cell is of a healthy subject.

According to specific embodiments, the cell is of a subject suffering from a pathology (e.g. cancer).

According to specific embodiments, the cell is an immune cell.

Non-limiting examples of immune cells that can be used with specific embodiments of the invention include T cells, NK cells, NKT cells, B cells, macrophages, dendritic cells (DCs) and granulocytes.

Methods of obtaining immune cells are well known in the art. Thus, for examples, PBMCs can be isolated by drawing whole blood from a subject and collection in a container containing an anti-coagulant (e.g. heparin or citrate); and apheresis. According to other specific embodiments, the immune cells are obtained from a tissue comprising cells associated with a pathology. Methods for obtaining a tissue sample from a subject are well known in the art and include e.g. biopsy, surgery or necropsy and preparing a single cell suspension thereof. Following, according to specific embodiments, at least one type of an immune cell is purified from the peripheral blood or from the single cell suspension. There are several methods and reagents known to those skilled in the art for purifying immune cells such as leukapheresis, sedimentation, density gradient centrifugation (e.g. ficoll), centrifugal elutriation, fractionation, chemical lysis of e.g. red blood cells (e.g. by ACK), selection of specific cell types using cell surface markers (using e.g. FACS sorter or magnetic cell separation techniques such as are commercially available e.g. from Invitrogen, Stemcell Technologies, Cellpro, Advanced Magnetics, or Miltenyi Biotec.), and depletion of specific cell types by methods such as eradication (e.g. killing) with specific antibodies or by affinity based purification based on negative selection (using e.g. magnetic cell separation techniques, FACS sorter and/or capture ELISA labeling). Such methods are described for example in THE HANDBOOK OF EXPERIMENTAL IMMUNOLOGY, Volumes 1 to 4, (D. N. Weir, editor) and FLOW CYTOMETRY AND CELL SORTING (A. Radbruch, editor, Springer Verlag, 2000).

According to specific embodiments, the immune cell is a T cell.

As used herein, the term "T cell" refers to a differentiated lymphocyte with a CD3+, T cell receptor (TCR)+ having either CD4+ or CD8+ phenotype.

According to specific embodiments, the T cell is an effector cell.

As used herein, the term "effector T cell" refers to a T cell that activates or directs other immune cells e.g. by producing cytokines or has a cytotoxic activity e.g., CD4+, Th1/Th2, CD8+ cytotoxic T lymphocyte.

According to other specific embodiments, the T cell is a regulatory cell.

As used herein, the term "regulatory T cell" or "Treg" refers to a T cell that negatively regulates the activation of other T cells, including effector T cells, as well as innate immune system cells. Treg cells are characterized by sustained suppression of effector T cell responses. According to a specific embodiment, the Treg is a CD4+CD25+Foxp3+ T cell.

According to specific embodiments, the T cell is a CD4+ T cell.

According to other specific embodiments, the T cell is a CD8+ T cell.

According to specific embodiments, the T cell is a naïve T cell.

According to specific embodiments, the T cell is a memory T cell. Non-limiting examples of memory T cells include effector memory CD4+ T cells with a CD3+/CD4+/CD45RA−/CCR7− phenotype, central memory CD4+ T cells with a CD3+/CD4+/CD45RA−/CCR7+ phenotype, effector memory CD8+ T cells with a CD3+/CD8+ CD45RA−/CCR7− phenotype and central memory CD8+ T cells with a CD3+/CD8+CD45RA−/CCR7+ phenotype.

According to specific embodiments, the T cell is expressing a T cell receptor specific for a pathologic (diseased, e.g. cancerous) cell, i.e. recognizes an antigen presented in the context of MHC which is overexpressed or solely expressed by a pathologic cell as compared to a non-pathologic cell.

According to specific embodiments, the pathologic cell is expressing a Siglec-7 and/or a Siglec-9 ligand.

According to specific embodiments, the T cell is endogenously expressing a T cell receptor specific for a pathologic cell (e.g. cancerous cell).

According to specific embodiments, the T cell is an engineered T cells transduced with a T cell receptor (TCR).

As used herein the phrase "transduced with a TCR" or "genetically engineered to express a TCR" refers to cloning of variable α- and β-chains from T cells with specificity against a desired antigen presented in the context of MHC. Methods of transducing with a TCR are known in the art and are disclosed e.g. in Nicholson et al. Adv Hematol. 2012; 2012:404081; Wang and Rivière Cancer Gene Ther. 2015 March; 22(2):85-94); and Lamers et al, Cancer Gene Therapy (2002) 9, 613-623. According to specific embodiments, the TCR is specific for a pathologic cell.

According to specific embodiments, the method further comprises transducing the T cell with a TCR.

According to specific embodiments, the T cell is an engineered T cells transduced with a chimeric antigen receptor (CAR).

As used herein, the phrase "transduced with a CAR" or "genetically engineered to express a CAR" refers to cloning of a nucleic acid sequence encoding a chimeric antigen receptor (CAR), wherein the CAR comprises an antigen recognition moiety and a T-cell activation moiety. A chimeric antigen receptor (CAR) is an artificially constructed hybrid protein or polypeptide containing an antigen binding domain of an antibody (e.g., a single chain variable fragment (scFv)) linked to T-cell signaling or T-cell activation domains. Method of transducing with a CAR are known in the art and are disclosed e.g. in Davila et al. Oncoimmunology. 2012 Dec. 1; 1(9):1577-1583; Wang and Rivière Cancer Gene Ther. 2015 March; 22(2):85-94); Maus et al. Blood. 2014 Apr. 24; 123(17):2625-35; Porter D L The New England journal of medicine. 2011, 365(8):725-733; Jackson H J, Nat Rev Clin Oncol. 2016; 13(6):370-383; and Globerson-Levin et al. Mol Ther. 2014; 22(5):1029-1038.

According to specific embodiments, the antigen recognition moiety is specific for a pathologic (diseased, e.g. cancerous) cell, i.e. recognizes an antigen which is overexpressed or solely expressed by a pathologic cell as compared to a non-pathologic cell.

According to other specific embodiments, the T cell is not transduced (i.e. does not express) a CAR.

According to specific embodiments, the method further comprises transducing the T cell with a CAR.

According to specific embodiments, the immune cells comprise NK cells.

Thus, according to an aspect of the present invention, there is provided an NK cell expressing a chimeric receptor comprising:

(a) an extracellular domain comprising an amino acid sequence of a Siglec-7 or a Siglec-9 receptor capable of binding a Siglec-7 and/or a Siglec-9 ligand; and (b) an intracellular domain comprising an amino acid sequence capable of transmitting an activating signal and/or a co-stimulatory signal in an immune cell expressing the chimeric receptor upon binding of said extracellular domain to said ligand.

As used herein the term "NK cells" refers to differentiated lymphocytes with a CD16+ CD56+ and/or CD57+ TCR− phenotype. NK are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

According to specific embodiments, the immune cells comprise NKT cells.

As used herein the term "NKT cells" refers to a specialized population of T cells that express a semi-invariant αβ T-cell receptor, but also express a variety of molecular markers that are typically associated with NK cells, such as NK1.1. NKT cells include NK1.1+ and NK1.1−, as well as CD4+, CD4−, CD8+ and CD8− cells. The TCR on NKT cells is unique in that it recognizes glycolipid antigens presented by the MHC I-like molecule CD1d. NKT cells can have either protective or deleterious effects due to their abilities to produce cytokines that promote either inflammation or immune tolerance.

According to specific embodiments, the immune cells comprise B cells.

As used herein the term "B cells" refers to a lymphocyte with a B cell receptor (BCR)+, CD19+ and or B220+ phenotype. B cells are characterized by their ability to bind a specific antigen and elicit a humoral response.

According to specific embodiments, the immune cells comprise phagocytic cells.

As used herein, the term "phagocytic cells" refer to a cell that is capable of phagocytosis and include both professional and non-professional phagocytic cells. Methods of analyzing phagocytosis are well known in the art and include for examples killing assays, flow cytometry and/or microscopic evaluation (live cell imaging, fluorescence microscopy, confocal microscopy, electron microscopy). According to specific embodiments, the phagocytic cells are selected from the group consisting of monocytes, dendritic cells (DCs) and granulocytes.

According to specific embodiments, the immune cells comprise monocytes.

According to specific embodiments, the term "monocytes" refers to both circulating monocytes and to macrophages (also referred to as mononuclear phagocytes) present in a tissue.

According to specific embodiments, the monocytes comprise macrophages. Typically, cell surface phenotype of macrophages include CD14, CD40, CD11b, CD64, F4/80 (mice)/EMR1 (human), lysozyme M, MAC-1/MAC-3 and CD68.

According to specific embodiments, the monocytes comprise circulating monocytes. Typically, cell surface phenotypes of circulating monocytes include CD14 and CD16 (e.g. CD14++CD16−, CD14+CD16++, CD14++CD16+).

According to specific embodiments, the immune cells comprise DCs.

As used herein the term "dendritic cells (DCs)" refers to any member of a diverse population of morphologically similar cell types found in lymphoid or non-lymphoid tissues. DCs are a class of professional antigen presenting cells, and have a high capacity for sensitizing HLA-restricted T cells. DCs include, for example, plasmacytoid dendritic cells, myeloid dendritic cells (including immature and mature dendritic cells), Langerhans cells, interdigitating cells, follicular dendritic cells. Dendritic cells may be recognized by function, or by phenotype, particularly by cell surface phenotype. These cells are characterized by their distinctive morphology having veil-like projections on the cell surface, intermediate to high levels of surface HLA-class II expression and ability to present antigen to T cells, particularly to naive T cells (See Steinman R, et al., Ann. Rev. Immunol. 1991; 9:271-196.). Typically, cell surface phenotype of DCs include CD1a+, CD4+, CD86+, or HLA-DR. The term DCs encompasses both immature and mature DCs.

According to specific embodiments, the immune cells comprise granulocytes.

As used herein, the tern "granulocytes" refer to polymorphonuclear leukocytes characterized by the presence of granules in their cytoplasm.

According to specific embodiments, the granulocytes comprise neutrophils.

According to specific embodiments, the granulocytes comprise mast-cells.

According to specific embodiments, when the chimeric receptor comprises a co-stimulatory signal amino acid sequence and is devoid of an activating amino acid sequence, the cells (e.g. T cells) endogenously or exogenously express an activating receptor (e.g. TCR, CAR) specific for a pathologic (e.g. cancerous) cell.

According to specific embodiments, the cells can be freshly isolated, stored e.g., cryopreserved (i.e. frozen) at e.g. liquid nitrogen temperature at any stage for long periods of time (e.g., months, years) for future use; and cell lines.

Methods of cryopreservation are commonly known by one of ordinary skill in the art and are disclosed e.g. in International Patent Application Publication Nos. WO2007054160 and WO 2001039594 and US Patent Application Publication No. US20120149108.

According to specific embodiments, the cells can be stored in a cell bank or a depository or storage facility.

Consequently, the present teachings further suggest the use of the cells and the methods disclosed herein as, but not limited to, a source for adoptive cells therapies.

Thus, according to an aspect of the present invention, the cells (e.g. immune cells) disclosed herein are for use in adoptive cell therapy.

The cells used according to specific embodiments of the present invention may be autologous or non-autologous; they can be syngeneic or non-syngeneic: allogeneic or xenogeneic to the subject; each possibility represents a separate embodiment of the present invention.

According to specific embodiments, the cells are autologous to the subject.

According to specific embodiments, the cells are non-autologous to the subject.

According to specific embodiments, the cells described herein are cultured, expanded and/or activated ex-vivo prior to administration to the subject.

Methods of culturing, expanding and activating cells such as immune cells are well known to the skilled in the art. For example, T cells may be activated ex-vivo in the presence of one or more molecule such as, but not limited to, an anti-CD3 antibody, an anti-CD28 antibody, anti-CD3 and anti-CD28 coated beads (such as the CD3CD28 MACSi-Beads obtained from Miltenyi Biotec), IL-2, phytohemoag-glutinin, an antigen-loaded antigen presenting cell [APC, e.g. dendritic cell], a peptide loaded recombinant MHC.

Since the cells of specific embodiments of the present invention are activated upon binding of the binding domain of the chimeric receptor to a Siglec-7 and/or Siglec-9 ligand, they may be used for, but not limited to, treating diseases associated with cells expressing a Siglec-7 and/or a Siglec-9 ligand.

Thus, according to an aspect of the present invention, there is provided a method of treating a disease associated with cells expressing a Siglec-7 and/or a Siglec-9 ligand in a subject in need thereof, the method comprising administering to the subject a therapeutically effective amount of the chimeric receptor, the polynucleotide or the cells of disclosed herein, thereby treating the disease in the subject.

According to an additional or an alternative aspect of the present invention, there is provided the chimeric receptor, the polynucleotide or the cell disclosed herein, for use in the treatment of a disease associated with cells expressing said Siglec-7 and/or said Siglec-9 ligand.

As used herein, the term "subject" or "subject in need thereof" includes mammals, preferably human beings at any age or gender. The subject may be healthy or showing preliminary signs of a pathology, e.g. cancer. This term also encompasses individuals who are at risk to develop the pathology.

As used herein the term "treating" refers to curing, reversing, attenuating, alleviating, minimizing, suppressing or halting the deleterious effects of a disease or disorder (e.g. cancer). Those of skill in the art will understand that various methodologies and assays can be used to assess the development of a pathology, and similarly, various methodologies and assays may be used to assess the reduction, remission or regression of a pathology (e.g. a malignancy), as discussed below.

As used herein the phrase, "a disease associated with cells expressing a Siglec-7 and/or a Siglec-9 ligand" means that cells expressing a Siglec-7 and/or a Siglec-9 ligand drive onset and/or progression of the disease.

According to specific embodiments, the expression of Siglec-7 and/or Siglec-9 ligand on the cells is at least 2 fold, at least 2.5 fold or at least 3 fold higher compared to background (i.e. non-specific staining), as determined by flow cytometry [e.g. using mean fluorescence intensity (MFI)].

According to specific embodiments, the disease can benefit from activating the immune cells of the subject.

As used herein the phrase "a disease that can benefit from activating immune cells" refers to diseases in which the subject's immune response activity may be sufficient to at least ameliorate symptoms of the disease or delay onset of symptoms, however for any reason the activity of the subject's immune response in doing so is less than optimal.

Non-limiting examples of diseases treated by some embodiments of the invention include cancer, infections, inflammatory diseases and autoimmune diseases.

According to specific embodiments, the disease comprises an infection.

As used herein, the term "infection" or "infectious disease" refers to a disease induced by a pathogen. Specific examples of pathogens include, viral pathogens, bacterial pathogens e.g., intracellular mycobacterial pathogens (such as, for example, *Mycobacterium tuberculosis*), intracellular bacterial pathogens (such as, for example, *Listeria monocytogenes*), or intracellular protozoan pathogens (such as, for example, *Leishmania* and *Trypanosoma*).

Specific types of viral pathogens causing infectious diseases include, but are not limited to, retroviruses, circoviruses, parvoviruses, papovaviruses, adenoviruses, herpesviruses, iridoviruses, poxviruses, hepadnaviruses, picornaviruses, caliciviruses, togaviruses, flaviviruses, reoviruses, orthomyxoviruses, paramyxoviruses, rhabdoviruses, bunyaviruses, coronaviruses, arenaviruses, and filoviruses.

Specific examples of viral infections which may be treated according to specific embodiments of the present invention include, but are not limited to, human immunodeficiency virus (HIV)-induced acquired immunodeficiency syndrome (AIDS), Group B Strep Infection, influenza, rhinoviral infection, viral meningitis, Epstein-Barr virus (EBV) infection, hepatitis A, B or C virus infection, measles, papilloma virus infection/warts, cytomegalovirus (CMV) infection, Herpes simplex virus infection, yellow fever, Ebola virus infection, rabies, etc.

According to a specific embodiment, the infection is an HIV infection.

According to specific embodiments, the disease is cancer.

Cancers which may be treated by some embodiments of the invention can be any solid or non-solid tumor, cancer metastasis and/or a pre-cancer.

According to specific embodiments, the cancer is a malignant cancer.

Examples of cancer include but are not limited to, carcinoma, blastoma, sarcoma and lymphoma. More particular examples of such cancers include, but are not limited to, tumors of the gastrointestinal tract (colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, Biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic; breast cancer, susceptibility to breast cancer, type 4 breast cancer, breast cancer-1, breast cancer-3; breast-ovarian cancer), squamous cell carcinoma (e.g., in head and neck), neurogenic tumor, astrocytoma, ganglio-blastoma, neuroblastoma, lymphomas (e.g., Hodgkin's disease, non-Hodgkin's lymphoma, B cell, Burkitt, cutaneous T cell, histiocytic, lymphoblastic, T cell, thymic), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocel-lular, transitional cell, undifferentiated, carcino sarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohy-bridoma, heteromyeloma, histiocytoma, hybridoma (e.g., B cell), hypernephroma, insulinoma, islet tumor, keratoma, leiomyoblastoma, leiomyosarcoma, leukemia (e.g., acute lymphatic, acute lymphoblastic, acute lymphoblastic pre-B cell, acute lymphoblastic T cell leukemia, acute-megakaryo-blastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia), lym-phosarcoma, melanoma, mammary tumor, mastocytoma, medulloblastoma, mesothelioma, metastatic tumor, mono-cyte tumor, multiple myeloma, myelodysplastic syndrome, myeloma, nephroblastoma, nervous tissue glial tumor, ner-vous tissue neuronal tumor, neurinoma, neuroblastoma, oli-godendroglioma, osteochondroma, osteomyeloma, osteosar-coma (e.g., Ewing's), papilloma, transitional cell, pheochromocytoma, pituitary tumor (invasive), plasmacy-toma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblas-toma multiforme; multiple glomus tumors, Li-Fraumeni syndrome, liposarcoma, lynch cancer family syndrome II, male germ cell tumor, mast cell leukemia, medullary thy-roid, multiple meningioma, endocrine neoplasia myxosar-coma, paraganglioma, familial nonchromaffin, pilomatri-coma, papillary, familial and sporadic, rhabdoid predisposition syndrome, familial, rhabdoid tumors, soft tissue sarcoma, and Turcot syndrome with glioblastoma.

According to specific embodiments, the cancer is a pre-malignant cancer.

Pre-cancers are well characterized and known in the art (refer, for example, to Berman J J. and Henson D E., 2003. Classifying the pre-cancers: a metadata approach. BMC Med Inform Decis Mak. 3:8). Examples of pre-cancers include, but are not limited to, acquired small pre-cancers, acquired large lesions with nuclear atypia, precursor lesions occurring with inherited hyperplastic syndromes that prog-ress to cancer, and acquired diffuse hyperplasias and diffuse metaplasias. Non-limiting examples of small pre-cancers include HGSIL (High grade squamous intraepithelial lesion of uterine cervix), AIN (anal intraepithelial neoplasia), dysplasia of vocal cord, aberrant crypts (of colon), PIN (pros-tatic intraepithelial neoplasia).

Non-limiting examples of acquired large lesions with nuclear atypia include tubular adenoma, AILD (angioimmu-noblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian pap-illoma. Non-limiting examples of precursor lesions occur-ring with inherited hyperplastic syndromes that progress to cancer include atypical mole syndrome, C cell adenomatosis and MEA. Non-limiting examples of acquired diffuse hyper-plasias and diffuse metaplasias include Paget's disease of bone and ulcerative colitis.

According to specific embodiments, the cancer is selected form the group consisting of melanoma, hepatocellular cancer, pancreatic cancer, colon adenocarcinoma, cervical cancer, breast cancer, lung cancer lymphoma and leukaemia.

According to specific embodiments, the cancer is selected form the group consisting of ovarian carcinoma, cervical cancer, pancreatic adenocarcinoma, leukaemia, melanoma, colon carcinoma, breast carcinoma and lung adenocarci-noma.

According to specific embodiments, the cancer is mela-noma.

According to specific embodiments, the disease is an inflammatory disease. Non-limiting examples of inflamma-tory diseases that can be treated according to specific embodiments of the present invention include liver fibrosis, airway inflammatory diseases e.g. chronic rhinosinusitis.

According to specific embodiments, chimeric receptor, the polynucleotide or the cell disclosed herein can be administered to a subject in combination with other estab-lished or experimental therapeutic regimen to treat a disease associated with cells expressing a Siglec-7 and/or a Siglec-9 ligand (e.g. cancer) including, but not limited to analgesics, chemotherapeutic agents, radiotherapeutic agents, cytotoxic therapies (conditioning), hormonal therapy and other treat-ment regimens (e.g., surgery) which are well known in the art.

The chimeric receptor, the polynucleotide or the cell disclosed herein can be administered to the subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administra-tion of a compound to an organism.

Herein the term "active ingredient" refers to the chimeric receptor, the polynucleotide or the cell accountable for the biological effect.

Thus, according to specific embodiments, the chimeric receptor, the polynucleotide or the cell disclosed herein is the active ingredient in the formulation.

According to specific embodiments, the chimeric recep-tor, the polynucleotide or the cell disclosed herein is the only active ingredient in the formulation.

Hereinafter, the phrases "physiologically acceptable car-rier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, intradermal, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Alternative embodiments include depots providing sustained release or prolonged duration of activity of the active ingredient in the subject, as are well known in the art.

Pharmaceutical compositions suitable for use in context of some embodiments of the invention include compositions wherein the active ingredients are contained in an amount effective to achieve the intended purpose. More specifically, a therapeutically effective amount means an amount of active ingredients effective to prevent, alleviate or ameliorate symptoms of a disorder (e.g., cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262;

3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

PBMcs and cell lines—PBLs were obtained from healthy donors from the Israeli Blood Bank (Tel-Hashomer, Israel) after obtaining an informed consent. The following cells and cell lines were used: DU-145 (ATCC/HTB-81), a prostate cancer line derived from metastatic site (brain); HeLa (ATCC/CCL-2), a cervix adenocarcinoma line; K562 (ATCC/CCL-243), a chronic myelogenous leukemia (CML) line; A375 (ATCC/CRL-1619), an epithelial skin melanoma line; 624.38 (CVCL_C588)), a melanoma cell line, HLA*A0201$^+$, MART1$^+$, NYESO-1$^+$; 888A2 (CVCL_4632) HLA*A0201$^+$, MART1$^+$, NYESO-1$^-$, a melanoma cell line; SK-MEL23 is a HLA-A2$^+$ melanoma cell line (CVCL_6027) HLA*A0201$^+$, MART1$^+$; Jurkat T-3.5 (ATCC/TIB-153), a T-cell leukemia line; PANC-1 (ATCC/CRL-1469), a pancreatic epitheloid carcinoma; A549 (ATCC/CCL-185), a lung epithelial carcinoma line; MCF7 (ATCC/HTB-22), an adenocarcinoma breast cancer of the mammary gland, derived from metastatic site; OVCAR8 a High grade ovarian serous adenocarcinoma cell line; M #3 and M #14, melanoma primary tumors (previously described in Eisenberg et al., Frontiers in immunology, 2017); packaging line 293GP (expressing GAG and POL, previously described in Eisenberg et al.). Tumor cells were cultured in RPMI (Invitrogen, Carlsbad, Calif., USA) or in DMEM (Invitrogen, Carlsbad, Calif., USA), both supplemented with 10% FBS (Biological Industries, Beth Haemek, Israel). Lymphocytes were cultured in BioTarget medium (Biological Industries, Beth Haemek, Israel), 10% FBS, and 300 IU/ml IL-2. Cells were maintained at 37° C. and 5% $CO_2$.

SIGLEC 7/9 chimeras constructs—The different chimeras (FIGS. 2, 8 and 11, SEQ ID NOs: 9-23, 36-50) were created by overlapping PCR with the DNA plasmid encoding the human SIGLEC 7/9 receptors. These chimeras were cloned into a retroviral vector backbone.

T-cell receptors (TCRs) and chimeric antigen receptor (CARs) constructs—The α and β chains from previously characterized TCRs specific for MART-1$_{26-35}$/HLA*0201 termed F4 were subcloned into the MSGV1 vector as described previously (Haga-Friedman A, Horovitz-Fried M, Cohen C J. J Immunol 2012; 188:5538-46).

Similarly, the chains encoding a codon-optimized version of the 1G4 TCR which is specific for the NYESO-1$_{157-165}$/HLA*A0201 epitope, were cloned in this retroviral vector. Similarly, an anti-CD19 CAR, that is composed of a scFv specific for the lymphoma CD19 (FMC63), fused to a 41BB and CD3z signaling molecules (aCD19BBz CAR), was synthesized and cloned into this vector.

Electroporation of PBLs—Effected as described in Haga-Friedman et al, JI, (2012). Briefly, in-vitro-transcribed mRNA for SIGLEC-7/9 different chimeric receptors were electroporated into OKT3-stimulated PBLs at 400V/500 μs using an ElectroSquare Porator ECM 830 (BTX, San Diego, Calif.). The amount of in-vitro-transcribed mRNA was 2 μg per $1\times10^6$ PBMCs.

Transduction of PBLs—For virus production, transfection of $2\times10^6$ 293 GP cells with 9 μg DNA of MSGV1-based retroviral construct and 4.5 μg envelop plasmid (VSV-G) was performed using JetPrime transfection reagent (Poly-plus, France). Retroviral supernatant was collected 36 hours following DNA transfection. Freshly isolated human PBLs were stimulated for 48 hours in the presence of 50 ng/ml OKT3 (eBioscience, San Diego, Calif., USA) prior to trans-duction. Following stimulation, lymphocytes were trans-duced with retroviral vectors by transfer to non-treated tissue culture dishes (Nunc, Rochester, N.Y., USA) that had been pre-coated with RetroNectin (Takara, Japan) and ret-roviral vectors as previously described (Eisenberg et al, Front. Immun., 2017).

Flow cytometry analysis and antibodies—Fluorophore-labeled anti-human CD8, CD137, SIGLEC-7 and SIGLEC-9 were purchased from BioLegend (San Diego, Calif., USA). For ligand expression tests, a recombinant Human Siglec-7/9 Fc Chimera Protein and as a secondary antibody-Human IgG Fc PE-conjugated Antibody (R&D Systems, Minneapolis, Minn., USA) were used. Immuno-fluorescence, analyzed as the relative log fluorescence of live cells, was measured using a CyAn-ADP flow cytometer (Beckman Coulter, Brea, Calif., USA). Approximately $1\times10^4$-$1\times10^5$ cells were analyzed. Cells were stained in a FACS buffer made of PBS, 0.5% BSA, and 0.02% sodium azide.

Cytokine release assays—Lymphocyte cultures were tested for reactivity in cytokine release assays using com-mercially available ELISA kits for IFNγ and TNFα (R&D Systems, Minneapolis, Minn., USA). For these assays, $2\times10^5$ responder cells (T-cells) and $1\times10^5$ stimulator cells (tumor cells) were incubated in a 0.2-ml culture volume in individual wells of 96-wells plates. Stimulator cells and responder cells were co-cultured for 18 hours. Cytokine secretion was measured in culture supernatants diluted to be in the linear range of the assay.

Cell-Mediated cytotoxicity assay—For cytotoxicity assay the CytoTox-ONE™ Homogeneous Membrane Integrity Assay was used, according to the manufacturer's instruc-tions (Promega). Cytotoxicity was analyzed as follows: Percent Cytotoxicity=100×(Experimental−Culture Medium Background)\(Maximum LDH Release−Culture Medium Background). Cells were incubated in 37° C. for 4 hours, at different effector:target (E:T) ratios (as indicated in the figure legend).

Animal Models and in Vivo Experiments—1-2×$10^6$ tumor cells were injected subcutaneously into the back flank area of 6 to 8 weeks year-old NOD-SCID-IL2R-mice (Har-lan, Jerusalem, Israel). Mice received three IV injections of $5\times10^6$ transduced lymphocytes, at a volume of 200 μL in HBSS medium four days following SC injection and there-after two injections every three days. Tumor size was measured (every 2 days) in a blinded fashion using a caliper and calculated using the following formula: [D×d2]×II/6, where D is the largest tumor diameter and d its perpendicular one. The study was conducted in compliance with the protocols approved by the Animal Care and Use Committees of Bar Ilan University, Ramat Gan, Israel.

Example 1

Figure 1:
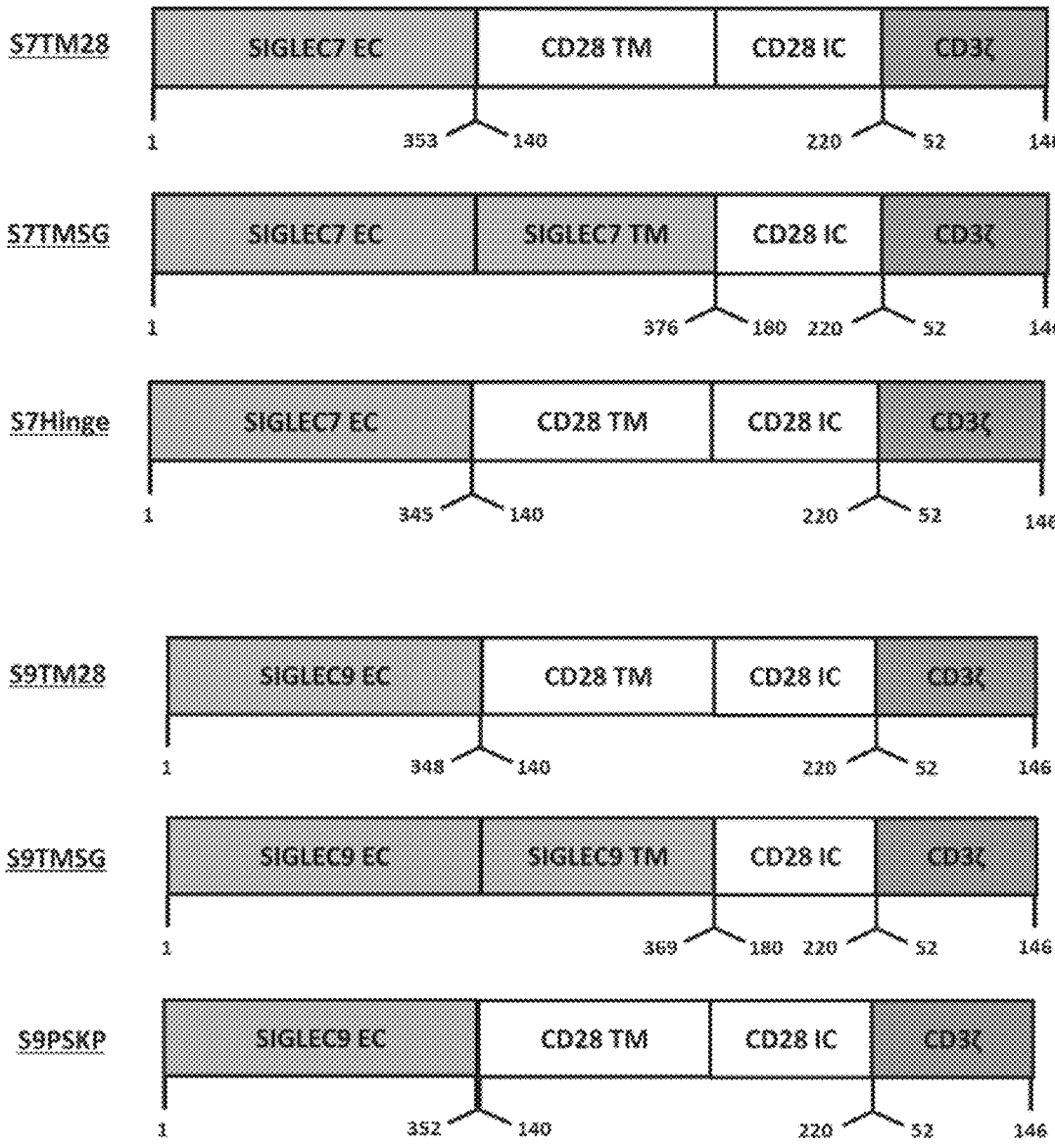
FIG. 1 is a schematic representation of the Siglec-7/9 chimeric constructs. The numbering relates to the amino acids coordinates in the original protein (SIGLEC 7: Q9Y286 (SIGL7_HUMAN); SIGLEC 9: Q9Y336

Expression of Functional Siglec-7 and Siglec-9 Based Chimeric Receptors in Lymphocytes Several chimeric receptors based on the extracellular domain of Siglec-7 or Siglec-9 fused to activating and/or co-stimulatory signaling moieties were generated (FIG. 1). These constructs were expressed in primary T-cells either by electroporation of by retroviral transduction and their expression was assessed by flow cytometry following stain-ing with an anti-Siglec-7 or anti-Siglec-9 fluorescent anti-body (FIGS. 2 and 3).

Following, the expression of Siglec-7 and Siglec-9 ligands on multiple tumor lines was assessed (FIG. 4), indicating most of the tested cell lines express significant levels of Siglec-7 and/or Siglec-9 ligands. Hence, the func-tion of the Siglec-7/9 based chimeric receptors expressed in T-cells was assessed in-vitro in co-cultures with several tumor lines by determining secretion of IFNγ as an immu-nological activity marker (FIGS. 5 and 6).

Overall, all the Siglec-7/9 chimeric receptors were func-tionally expressed, while the Siglec-7/9 chimeric receptors comprising a CD28 transmembrane region were the best constructs in both terms of expression and function.

To further evaluate the therapeutic potential of these generated Siglec-7/9 based chimeric receptors, T-cells engi-neered to express the Siglec-7/9 chimeric receptors com-prising a CD28 transmembrane region were adoptively transferred to NSG mice that were previously inoculated with 2e6 M #3 melanoma cells. As shown in FIG. 7, T cells expressing Siglec-7 or Siglec-9 based chimeric receptors significantly inhibited tumor growth compared to control injections (CD34), thus demonstrating the utility of this approach for targeting tumors in-vivo.

Example 2

The Ig-Like V-Type Domain and the Ig-Like C2-Type Domain of Siglec-7/9 Mediate Recognition and Function of the Siglec-7/9 Based Chimeric Receptors In order to determine which of the 3 Ig-like domains of Siglec-7/9 receptor are essential for the recognition and function of the Siglec-7/9 based chimeric receptors, con-structs encoding chimeric receptors wherein the extracellu-lar Siglec-based moiety comprises either the N terminal Ig-like V-type domain (domain 1), the N-terminal Ig-like V-type domain and the intermediate Ig-like C2-type domain (domains 1+2) or the N-terminal Ig-like V-type domain and the C-terminal Ig-like C2-type domain (domains 1+3) were generated (FIG. 8).

These constructs were expressed in primary T-cells and their expression was analyzed by flow cytometry (FIG. 9). Subsequently, their function was also assessed in co-cultures with the K562 cells as target cells, by determining secretion of IFNγ (FIG. 10).

As shown in FIGS. 9-10, inclusion of either domain 2 or 3 in the construct increased both expression and function of the chimeric receptor.

Example 3

Expression of Functional Siglec-7 and Siglec-9 Based Chimeric Co-Stimulatory Switch Receptors in Lymphocytes An additional possibility to harness the presence of Siglec-7/9 ligands on the surface tumor cells in the context of T-cell engineering is to use chimeric co-stimulatory switch receptors (CSR) based on the extracellular domain of Siglec-7 or Siglec-9 fused to a co-stimulatory signaling moiety without a an activating signaling moiety (FIG. 11). Such co-stimulatory signaling moiety can be the intracellular domain of CD28 or any other co-stimulatory molecule (e.g. 41BB, OX40, ICOS).

To demonstrate the potential of Siglec-7/9 based CSR, the generated CSR construct S728 or S929 was transduced along with a CD19 specific 4-1BB based CAR into primary human T-cells and expression was analyzed by flow cytometry (FIG. 12). Subsequently, the function of the transduced cells was also assessed in co-cultures with K562 or Raji target cells, by determining secretion of TNFα (FIG. 13).

As shown in FIGS. 12-13, Siglec-7/9 based CSRs enhanced the anti-tumor function of CAR-T cells.

In the next step, the potential of Siglec-7/9 based CSR, was assessed in the context of T-cells engineered to express an exogenous TCR directed against a defined epitope.

To demonstrate the potential of Siglec-based CSR, S928 (FIG. 11) was transduced along with an NYESO-1 specific TCR (termed 1G4) into primary human T-cells. Subsequently, the function of the transduced cells was assessed in co-cultures with A375 and 624.38 target cells, by determining secretion of TNFα (FIG. 14). T-cells expressing the 1G4

TCR and S928 secreted significantly more cytokine compared to T-cells that expressed only the TCR.

Following, the enhancing effect mediated by SIGLEC-based CSRs was determined with another TCR, namely a melanoma specific TCR (termed F4) that recognize a MART-1 derived specific epitope. To this end, primary human T-cells were transduced with the F4 TCR and different Siglec9-based CSR (FIG. 11) and their function was assessed in co-cultures with 888A2, SK-me123 and 624.38 target cells, by determining secretion of TNFα or IFNγ. As shown in FIGS. 15-16, Siglec-based CSRs enhanced the anti-tumor function of the TCR transduced-T cells.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

---

What is claimed is:

1. A chimeric receptor comprising:
   (a) an extracellular domain comprising an amino acid sequence of a Siglec-7 or a Siglec-9 receptor, wherein said amino acid sequence comprises an Ig-like V-type domain that binds a Siglec-7 and/or a Siglec-9 ligand and an Ig-like C2-domain; and
   (b) an intracellular immune activation and/or co-stimulatory signaling domain which transmits an activating signal and/or a co-stimulatory signal in an immune cell expressing the chimeric receptor upon binding of said extracellular domain to said ligand.

2. The chimeric receptor of claim 1, wherein said Ig-like C2-type domain is located C-terminally to said Ig-like V-type domain.

3. The chimeric receptor of claim 1, wherein said Ig-like C2-type domain is a single Ig-like C2-type domain.

4. The chimeric receptor of claim 1, wherein said Ig-like C2-type domain is the third Ig-like domain located N to C in a full length Siglec-7 or Siglec-9 receptor.

5. The chimeric receptor of claim 1, wherein an amino acid sequence of said Ig-like C2-type domain comprises an amino acid sequence having at least 80% identity to SEQ ID NO: 4 or 8.

6. The chimeric receptor of claim 1, wherein said amino acid sequence of said Ig-like C2-type domain comprises SEQ ID NO: 4 or 8.

7. The chimeric receptor of claim 1, wherein said immune activation signaling domain is of CD3zeta or FcR gamma.

8. The chimeric receptor of claim 1, wherein said immune costimulatory signaling domain is of a protein selected from the group consisting of 4-1BB, OX40, CD28, CD27, ICOS, CD40L, GITR, LIGHT, HVEM and CD30.

9. The chimeric receptor of claim 1, wherein the amino acid sequence of said Ig-like V-type domain has at least 80% identity to SEQ ID NO: 2 or 6.

10. The chimeric receptor of claim 1, wherein the amino acid sequence of said Ig-like V-type domain comprises SEQ ID NO: 2 or 6.

11. The chimeric receptor of claim 1, further comprising a transmembrane domain of CD28 or CD8a situated between the extracellular domain and the intracellular domain.

12. A polynucleotide encoding the chimeric receptor of claim 1.

13. A host cell expressing the chimeric receptor of claim 1.

14. The host cell of claim 13, being an immune cell.

15. The host cell of claim 14, wherein the immune cell is an NK cell.

16. A method of treating cancer expressing a Siglec-7 and/or a Siglec-9 ligand in a subject in need thereof, the method comprising administering to the subject a therapeutically effective amount of the cells of claim 14, thereby treating the cancer in the subject.

*    *    *    *    *

SEQUENCE LISTING

```
<160> NUMBER OF SEQ ID NOS: 64

<210> SEQ ID NO 1
<211> LENGTH: 467
<212> TYPE: PRT
<213> ORGANISM: Homo sapiens

<400> SEQUENCE: 1

Met Leu Leu Leu Leu Leu Leu Pro Leu Leu Trp Gly Arg Glu Arg Val
1               5                   10                  15

Glu Gly Gln Lys Ser Asn Arg Lys Asp Tyr Ser Leu Thr Met Gln Ser
            20                  25                  30

Ser Val Thr Val Gln Glu Gly Met Cys Val His Val Arg Cys Ser Phe
        35                  40                  45

Ser Tyr Pro Val Asp Ser Gln Thr Asp Ser Asp Pro Val His Gly Tyr
    50                  55                  60

Trp Phe Arg Ala Gly Asn Asp Ile Ser Trp Lys Ala Pro Val Ala Thr
65                  70                  75                  80

Asn Asn Pro Ala Trp Ala Val Gln Glu Glu Thr Arg Asp Arg Phe His
                85                  90                  95

Leu Leu Gly Asp Pro Gln Thr Lys Asn Cys Thr Leu Ser Ile Arg Asp
            100                 105                 110

Ala Arg Met Ser Asp Ala Gly Arg Tyr Phe Phe Arg Met Glu Lys Gly
        115                 120                 125

Asn Ile Lys Trp Asn Tyr Lys Tyr Asp Gln Leu Ser Val Asn Val Thr
    130                 135                 140
```

-continued

```
Ala Leu Thr His Arg Pro Asn Ile Leu Ile Pro Gly Thr Leu Glu Ser
145                 150                 155                 160

Gly Cys Phe Gln Asn Leu Thr Cys Ser Val Pro Trp Ala Cys Glu Gln
                165                 170                 175

Gly Thr Pro Pro Met Ile Ser Trp Met Gly Thr Ser Val Ser Pro Leu
                180                 185                 190

His Pro Ser Thr Thr Arg Ser Ser Val Leu Thr Leu Ile Pro Gln Pro
                195                 200                 205

Gln His His Gly Thr Ser Leu Thr Cys Gln Val Thr Leu Pro Gly Ala
                210                 215                 220

Gly Val Thr Thr Asn Arg Thr Ile Gln Leu Asn Val Ser Tyr Pro Pro
225                 230                 235                 240

Gln Asn Leu Thr Val Thr Val Phe Gln Gly Glu Gly Thr Ala Ser Thr
                245                 250                 255

Ala Leu Gly Asn Ser Ser Ser Leu Ser Val Leu Glu Gly Gln Ser Leu
                260                 265                 270

Arg Leu Val Cys Ala Val Asp Ser Asn Pro Pro Ala Arg Leu Ser Trp
                275                 280                 285

Thr Trp Arg Ser Leu Thr Leu Tyr Pro Ser Gln Pro Ser Asn Pro Leu
                290                 295                 300

Val Leu Glu Leu Gln Val His Leu Gly Asp Glu Gly Glu Phe Thr Cys
305                 310                 315                 320

Arg Ala Gln Asn Ser Leu Gly Ser Gln His Val Ser Leu Asn Leu Ser
                325                 330                 335

Leu Gln Gln Glu Tyr Thr Gly Lys Met Arg Pro Val Ser Gly Val Leu
                340                 345                 350

Leu Gly Ala Val Gly Gly Ala Gly Ala Thr Ala Leu Val Phe Leu Ser
                355                 360                 365

Phe Cys Val Ile Phe Ile Val Val Arg Ser Cys Arg Lys Lys Ser Ala
                370                 375                 380

Arg Pro Ala Ala Asp Val Gly Asp Ile Gly Met Lys Asp Ala Asn Thr
385                 390                 395                 400

Ile Arg Gly Ser Ala Ser Gln Gly Asn Leu Thr Glu Ser Trp Ala Asp
                405                 410                 415

Asp Asn Pro Arg His His Gly Leu Ala Ala His Ser Ser Gly Glu Glu
                420                 425                 430

Arg Glu Ile Gln Tyr Ala Pro Leu Ser Phe His Lys Gly Glu Pro Gln
                435                 440                 445

Asp Leu Ser Gly Gln Glu Ala Thr Asn Asn Glu Tyr Ser Glu Ile Lys
                450                 455                 460

Ile Pro Lys
465
```

```
<210> SEQ ID NO 2
<211> LENGTH: 128
<212> TYPE: PRT
<213> ORGANISM: Artificial sequence
<220> FEATURE:
<223> OTHER INFORMATION: IgG-like V domain of Siglec7

<400> SEQUENCE: 2

Gln Lys Ser Asn Arg Lys Asp Tyr Ser Leu Thr Met Gln Ser Ser Val
1               5                   10                  15

Thr Val Gln Glu Gly Met Cys Val His Val Arg Cys Ser Phe Ser Tyr
                20                  25                  30
```

-continued

```
Pro Val Asp Ser Gln Thr Asp Ser Asp Pro Val His Gly Tyr Trp Phe
        35              40              45

Arg Ala Gly Asn Asp Ile Ser Trp Lys Ala Pro Val Ala Thr Asn Asn
        50              55              60

Pro Ala Trp Ala Val Gln Glu Glu Thr Arg Asp Arg Phe His Leu Leu
65              70              75              80

Gly Asp Pro Gln Thr Lys Asn Cys Thr Leu Ser Ile Arg Asp Ala Arg
                85              90              95

Met Ser Asp Ala Gly Arg Tyr Phe Phe Arg Met Glu Lys Gly Asn Ile
            100             105             110

Lys Trp Asn Tyr Lys Tyr Asp Gln Leu Ser Val Asn Val Thr Ala Leu
        115             120             125
```

```
<210> SEQ ID NO 3
<211> LENGTH: 90
<212> TYPE: PRT
<213> ORGANISM: Artificial sequence
<220> FEATURE:
<223> OTHER INFORMATION: IgG-like C2 domain of Siglec 7 (domain 2)

<400> SEQUENCE: 3
```

```
His Arg Pro Asn Ile Leu Ile Pro Gly Thr Leu Glu Ser Gly Cys Phe
1               5               10              15

Gln Asn Leu Thr Cys Ser Val Pro Trp Ala Cys Glu Gln Gly Thr Pro
        20              25              30

Pro Met Ile Ser Trp Met Gly Thr Ser Val Ser Pro Leu His Pro Ser
        35              40              45

Thr Thr Arg Ser Ser Val Leu Thr Leu Ile Pro Gln Pro Gln His His
        50              55              60

Gly Thr Ser Leu Thr Cys Gln Val Thr Leu Pro Gly Ala Gly Val Thr
65              70              75              80

Thr Asn Arg Thr Ile Gln Leu Asn Val Ser
                85              90
```

```
<210> SEQ ID NO 4
<211> LENGTH: 91
<212> TYPE: PRT
<213> ORGANISM: Artificial sequence
<220> FEATURE:
<223> OTHER INFORMATION: IgG-like C2 domain of Siglec 7 (domain 3)

<400> SEQUENCE: 4
```

```
Glu Gly Thr Ala Ser Thr Ala Leu Gly Asn Ser Ser Ser Leu Ser Val
1               5               10              15

Leu Glu Gly Gln Ser Leu Arg Leu Val Cys Ala Val Asp Ser Asn Pro
        20              25              30

Pro Ala Arg Leu Ser Trp Thr Trp Arg Ser Leu Thr Leu Tyr Pro Ser
        35              40              45

Gln Pro Ser Asn Pro Leu Val Leu Glu Leu Gln Val His Leu Gly Asp
        50              55              60

Glu Gly Glu Phe Thr Cys Arg Ala Gln Asn Ser Leu Gly Ser Gln His
65              70              75              80

Val Ser Leu Asn Leu Ser Leu Gln Gln Glu Tyr
                85              90
```

```
<210> SEQ ID NO 5
<211> LENGTH: 479
<212> TYPE: PRT
<213> ORGANISM: Homo sapiens
```

-continued

<400> SEQUENCE: 5

```
Met Leu Leu Leu Leu Leu Pro Leu Leu Trp Gly Arg Glu Arg Ala Glu
1               5                   10                  15

Gly Gln Thr Ser Lys Leu Leu Thr Met Gln Ser Ser Val Thr Val Gln
            20                  25                  30

Glu Gly Leu Cys Val His Val Pro Cys Ser Phe Ser Tyr Pro Ser His
        35                  40                  45

Gly Trp Ile Tyr Pro Gly Pro Val Val His Gly Tyr Trp Phe Arg Glu
    50                  55                  60

Gly Ala Asn Thr Asp Gln Asp Ala Pro Val Ala Thr Asn Asn Pro Ala
65                  70                  75                  80

Arg Ala Val Trp Glu Glu Thr Arg Asp Arg Phe His Leu Leu Gly Asp
                85                  90                  95

Pro His Thr Lys Asn Cys Thr Leu Ser Ile Arg Asp Ala Arg Arg Ser
            100                 105                 110

Asp Ala Gly Arg Tyr Phe Phe Arg Met Glu Lys Gly Ser Ile Lys Trp
            115                 120                 125

Asn Tyr Lys His His Arg Leu Ser Val Asn Val Thr Ala Leu Thr His
        130                 135                 140

Arg Pro Asn Ile Leu Ile Pro Gly Thr Leu Glu Ser Gly Cys Pro Gln
145                 150                 155                 160

Asn Leu Thr Cys Ser Val Pro Trp Ala Cys Glu Gln Gly Thr Pro Pro
                165                 170                 175

Met Ile Ser Trp Ile Gly Thr Ser Val Ser Pro Leu Asp Pro Ser Thr
            180                 185                 190

Thr Arg Ser Ser Val Leu Thr Leu Ile Pro Gln Pro Gln Asp His Gly
            195                 200                 205

Thr Ser Leu Thr Cys Gln Val Thr Phe Pro Gly Ala Ser Val Thr Thr
        210                 215                 220

Asn Lys Thr Val His Leu Asn Val Ser Tyr Pro Pro Gln Asn Leu Thr
225                 230                 235                 240

Met Thr Val Phe Gln Gly Asp Gly Thr Val Ser Thr Val Leu Gly Asn
                245                 250                 255

Gly Ser Ser Leu Ser Leu Pro Glu Gly Gln Ser Leu Arg Leu Val Cys
            260                 265                 270

Ala Val Asp Ala Val Asp Ser Asn Pro Pro Ala Arg Leu Ser Leu Ser
            275                 280                 285

Trp Arg Gly Leu Thr Leu Cys Pro Ser Gln Pro Ser Asn Pro Gly Val
    290                 295                 300

Leu Glu Leu Pro Trp Val His Leu Arg Asp Ala Ala Glu Phe Thr Cys
305                 310                 315                 320

Arg Ala Gln Asn Pro Leu Gly Ser Gln Gln Val Tyr Leu Asn Val Ser
            325                 330                 335

Leu Gln Ser Lys Ala Thr Ser Gly Val Thr Gln Gly Val Val Gly Gly
            340                 345                 350

Ala Gly Ala Thr Ala Leu Val Phe Leu Ser Phe Cys Val Ile Phe Val
        355                 360                 365

Val Val Arg Ser Cys Arg Lys Lys Ser Ala Arg Pro Ala Ala Gly Val
        370                 375                 380

Gly Asp Thr Gly Ile Glu Asp Ala Asn Ala Val Arg Gly Ser Ala Ser
385                 390                 395                 400

Gln Ile Leu Asn His Phe Ile Gly Phe Pro Thr Phe Leu Gly Leu Gly
```

-continued

```
                    405                 410                 415

Phe Glu Phe Leu Leu Asn Leu Arg Asp Leu Cys Cys His Pro Asp Ser
            420                 425                 430

Glu Phe Tyr Val Tyr His Phe Ser His Phe Arg Leu Ile Lys Asn Ile
        435                 440                 445

Ala Gly Glu Ile Val Trp Ser Leu Glu Gly Lys Ile Leu Trp Leu Leu
    450                 455                 460

Asp Val Ser Asp Phe Phe His Trp Phe Phe Leu Ile Cys Val Gly
465                 470                 475

<210> SEQ ID NO 6
<211> LENGTH: 126
<212> TYPE: PRT
<213> ORGANISM: Artificial sequence
<220> FEATURE:
<223> OTHER INFORMATION: IgG-like V domain of Siglec9

<400> SEQUENCE: 6

Gly Gln Thr Ser Lys Leu Leu Thr Met Gln Ser Ser Val Thr Val Gln
1               5                   10                  15

Glu Gly Leu Cys Val His Val Pro Cys Ser Phe Ser Tyr Pro Ser His
            20                  25                  30

Gly Trp Ile Tyr Pro Gly Pro Val Val His Gly Tyr Trp Phe Arg Glu
        35                  40                  45

Gly Ala Asn Thr Asp Gln Asp Ala Pro Val Ala Thr Asn Asn Pro Ala
    50                  55                  60

Arg Ala Val Trp Glu Glu Thr Arg Asp Arg Phe His Leu Leu Gly Asp
65                  70                  75                  80

Pro His Thr Lys Asn Cys Thr Leu Ser Ile Arg Asp Ala Arg Arg Ser
                85                  90                  95

Asp Ala Gly Arg Tyr Phe Phe Arg Met Glu Lys Gly Ser Ile Lys Trp
            100                 105                 110

Asn Tyr Lys His His Arg Leu Ser Val Asn Val Thr Ala Leu
        115                 120                 125

<210> SEQ ID NO 7
<211> LENGTH: 90
<212> TYPE: PRT
<213> ORGANISM: Artificial sequence
<220> FEATURE:
<223> OTHER INFORMATION: IgG-like C2 domain of Siglec 9 (domain 2)

<400> SEQUENCE: 7

His Arg Pro Asn Ile Leu Ile Pro Gly Thr Leu Glu Ser Gly Cys Pro
1               5                   10                  15

Gln Asn Leu Thr Cys Ser Val Pro Trp Ala Cys Glu Gln Gly Thr Pro
            20                  25                  30

Pro Met Ile Ser Trp Ile Gly Thr Ser Val Ser Pro Leu Asp Pro Ser
        35                  40                  45

Thr Thr Arg Ser Ser Val Leu Thr Leu Ile Pro Gln Pro Gln Asp His
    50                  55                  60

Gly Thr Ser Leu Thr Cys Gln Val Thr Phe Pro Gly Ala Ser Val Thr
65                  70                  75                  80

Thr Asn Lys Thr Val His Leu Asn Val Ser
                85                  90

<210> SEQ ID NO 8
<211> LENGTH: 95
```

<212> TYPE: PRT
<213> ORGANISM: Artificial sequence
<220> FEATURE:
<223> OTHER INFORMATION: IgG-like C2 domain of Siglec 9 (domain 3)

<400> SEQUENCE: 8

Asp Gly Thr Val Ser Thr Val Leu Gly Asn Gly Ser Ser Leu Ser Leu
1               5                   10                  15

Pro Glu Gly Gln Ser Leu Arg Leu Val Cys Ala Val Asp Ala Val Asp
            20                  25                  30

Ser Asn Pro Pro Ala Arg Leu Ser Leu Ser Trp Arg Gly Leu Thr Leu
        35                  40                  45

Cys Pro Ser Gln Pro Ser Asn Pro Gly Val Leu Glu Leu Pro Trp Val
    50                  55                  60

His Leu Arg Asp Ala Ala Glu Phe Thr Cys Arg Ala Gln Asn Pro Leu
65                  70                  75                  80

Gly Ser Gln Gln Val Tyr Leu Asn Val Ser Leu Gln Ser Lys Ala
                85                  90                  95

<210> SEQ ID NO 9
<211> LENGTH: 536
<212> TYPE: PRT
<213> ORGANISM: Artificial sequence
<220> FEATURE:
<223> OTHER INFORMATION: S7TM28 construct aa sequence

<400> SEQUENCE: 9

Met Ser Leu Leu Leu Leu Leu Leu Pro Leu Leu Trp Gly Arg Glu Arg
1               5                   10                  15

Val Glu Gly Gln Lys Ser Asn Arg Lys Asp Tyr Ser Leu Thr Met Gln
            20                  25                  30

Ser Ser Val Thr Val Gln Glu Gly Met Cys Val His Val Arg Cys Ser
        35                  40                  45

Phe Ser Tyr Pro Val Asp Ser Gln Thr Asp Ser Asp Pro Val His Gly
    50                  55                  60

Tyr Trp Phe Arg Ala Gly Asn Asp Ile Ser Trp Lys Ala Pro Val Ala
65                  70                  75                  80

Thr Asn Asn Pro Ala Trp Ala Val Gln Glu Glu Thr Arg Asp Arg Phe
                85                  90                  95

His Leu Leu Gly Asp Pro Gln Thr Lys Asn Cys Thr Leu Ser Ile Arg
                100                 105                 110

Asp Ala Arg Met Ser Asp Ala Gly Arg Tyr Phe Phe Arg Met Glu Lys
            115                 120                 125

Gly Asn Ile Lys Trp Asn Tyr Lys Tyr Asp Gln Leu Ser Val Asn Val
        130                 135                 140

Thr Ala Leu Thr His Arg Pro Asn Ile Leu Ile Pro Gly Thr Leu Glu
145                 150                 155                 160

Ser Gly Cys Phe Gln Asn Leu Thr Cys Ser Val Pro Trp Ala Cys Glu
                165                 170                 175

Gln Gly Thr Pro Pro Met Ile Ser Trp Met Gly Thr Ser Val Ser Pro
            180                 185                 190

Leu His Pro Ser Thr Thr Arg Ser Ser Val Leu Thr Leu Ile Pro Gln
            195                 200                 205

Pro Gln His His Gly Thr Ser Leu Thr Cys Gln Val Thr Leu Pro Gly
        210                 215                 220

Ala Gly Val Thr Thr Asn Arg Thr Ile Gln Leu Asn Val Ser Tyr Pro
225                 230                 235                 240

```
Pro Gln Asn Leu Thr Val Thr Val Phe Gln Gly Gly Thr Ala Ser
            245             250             255

Thr Ala Leu Gly Asn Ser Ser Ser Leu Ser Val Leu Glu Gly Gln Ser
            260             265             270

Leu Arg Leu Val Cys Ala Val Asp Ser Asn Pro Pro Ala Arg Leu Ser
            275             280             285

Trp Thr Trp Arg Ser Leu Thr Leu Tyr Pro Ser Gln Pro Ser Asn Pro
    290             295             300

Leu Val Leu Glu Leu Gln Val His Leu Gly Asp Glu Gly Glu Phe Thr
305             310             315             320

Cys Arg Ala Gln Asn Ser Leu Gly Ser Gln His Val Ser Leu Asn Leu
            325             330             335

Ser Leu Gln Gln Glu Tyr Thr Gly Lys Met Arg Pro Val Ser Gly Val
            340             345             350

Leu Leu Ala Ser Phe Trp Val Leu Val Val Val Gly Gly Val Leu Ala
            355             360             365

Cys Tyr Ser Leu Leu Val Thr Val Ala Phe Ile Ile Phe Trp Val Arg
    370             375             380

Ser Lys Arg Ser Arg Leu Leu His Ser Asp Tyr Met Asn Met Thr Pro
385             390             395             400

Arg Arg Pro Gly Pro Thr Arg Lys His Tyr Gln Pro Tyr Ala Pro Pro
            405             410             415

Arg Asp Phe Ala Ala Tyr Arg Ser Arg Val Lys Phe Ser Arg Ser Ala
            420             425             430

Asp Ala Pro Ala Tyr Gln Gln Gly Gln Asn Gln Leu Tyr Asn Glu Leu
            435             440             445

Asn Leu Gly Arg Arg Glu Glu Tyr Asp Val Leu Asp Lys Arg Arg Gly
    450             455             460

Arg Asp Pro Glu Met Gly Gly Lys Pro Arg Arg Lys Asn Pro Gln Glu
465             470             475             480

Gly Leu Tyr Asn Glu Leu Gln Lys Asp Lys Met Ala Glu Ala Tyr Ser
            485             490             495

Glu Ile Gly Met Lys Gly Glu Arg Arg Arg Gly Lys Gly His Asp Gly
            500             505             510

Leu Tyr Gln Gly Leu Ser Thr Ala Thr Lys Asp Thr Tyr Asp Ala Leu
            515             520             525

His Met Gln Ala Leu Pro Pro Arg
            530             535
```

```
<210> SEQ ID NO 10
<211> LENGTH: 530
<212> TYPE: PRT
<213> ORGANISM: Artificial sequence
<220> FEATURE:
<223> OTHER INFORMATION: S7TMSG construct aa sequence

<400> SEQUENCE: 10
```

```
Met Ser Leu Leu Leu Leu Leu Leu Pro Leu Leu Trp Gly Arg Glu Arg
1               5               10              15

Val Glu Gly Gln Lys Ser Asn Arg Lys Asp Tyr Ser Leu Thr Met Gln
            20              25              30

Ser Ser Val Thr Val Gln Glu Gly Met Cys Val His Val Arg Cys Ser
        35              40              45

Phe Ser Tyr Pro Val Asp Ser Gln Thr Asp Ser Asp Pro Val His Gly
    50              55              60
```

-continued

```
Tyr Trp Phe Arg Ala Gly Asn Asp Ile Ser Trp Lys Ala Pro Val Ala
65                  70                  75                  80

Thr Asn Asn Pro Ala Trp Ala Val Gln Glu Glu Thr Arg Asp Arg Phe
                85                  90                  95

His Leu Leu Gly Asp Pro Gln Thr Lys Asn Cys Thr Leu Ser Ile Arg
                100                 105                 110

Asp Ala Arg Met Ser Asp Ala Gly Arg Tyr Phe Phe Arg Met Glu Lys
                115                 120                 125

Gly Asn Ile Lys Trp Asn Tyr Lys Tyr Asp Gln Leu Ser Val Asn Val
        130                 135                 140

Thr Ala Leu Thr His Arg Pro Asn Ile Leu Ile Pro Gly Thr Leu Glu
145                 150                 155                 160

Ser Gly Cys Phe Gln Asn Leu Thr Cys Ser Val Pro Trp Ala Cys Glu
                165                 170                 175

Gln Gly Thr Pro Pro Met Ile Ser Trp Met Gly Thr Ser Val Ser Pro
                180                 185                 190

Leu His Pro Ser Thr Thr Arg Ser Ser Val Leu Thr Leu Ile Pro Gln
                195                 200                 205

Pro Gln His His Gly Thr Ser Leu Thr Cys Gln Val Thr Leu Pro Gly
        210                 215                 220

Ala Gly Val Thr Thr Asn Arg Thr Ile Gln Leu Asn Val Ser Tyr Pro
225                 230                 235                 240

Pro Gln Asn Leu Thr Val Thr Val Phe Gln Gly Glu Gly Thr Ala Ser
                245                 250                 255

Thr Ala Leu Gly Asn Ser Ser Ser Leu Ser Val Leu Glu Gly Gln Ser
                260                 265                 270

Leu Arg Leu Val Cys Ala Val Asp Ser Asn Pro Pro Ala Arg Leu Ser
        275                 280                 285

Trp Thr Trp Arg Ser Leu Thr Leu Tyr Pro Ser Gln Pro Ser Asn Pro
        290                 295                 300

Leu Val Leu Glu Leu Gln Val His Leu Gly Asp Glu Gly Glu Phe Thr
305                 310                 315                 320

Cys Arg Ala Gln Asn Ser Leu Gly Ser Gln His Val Ser Leu Asn Leu
                325                 330                 335

Ser Leu Gln Gln Glu Tyr Thr Gly Lys Met Arg Pro Val Ser Gly Val
                340                 345                 350

Leu Leu Gly Ala Val Gly Gly Ala Gly Ala Thr Ala Leu Val Phe Leu
        355                 360                 365

Ser Phe Cys Val Ile Phe Ile Val Val Arg Ser Lys Arg Ser Arg Leu
        370                 375                 380

Leu His Ser Asp Tyr Met Asn Met Thr Pro Arg Arg Pro Gly Pro Thr
385                 390                 395                 400

Arg Lys His Tyr Gln Pro Tyr Ala Pro Pro Arg Asp Phe Ala Ala Tyr
                405                 410                 415

Arg Ser Arg Val Lys Phe Ser Arg Ser Ala Asp Ala Pro Ala Tyr Gln
                420                 425                 430

Gln Gly Gln Asn Gln Leu Tyr Asn Glu Leu Asn Leu Gly Arg Arg Glu
        435                 440                 445

Glu Tyr Asp Val Leu Asp Lys Arg Arg Gly Arg Asp Pro Glu Met Gly
        450                 455                 460

Gly Lys Pro Arg Arg Lys Asn Pro Gln Glu Gly Leu Tyr Asn Glu Leu
465                 470                 475                 480
```

```
Gln Lys Asp Lys Met Ala Glu Ala Tyr Ser Glu Ile Gly Met Lys Gly
                485                 490                 495

Glu Arg Arg Arg Gly Lys Gly His Asp Gly Leu Tyr Gln Gly Leu Ser
            500                 505                 510

Thr Ala Thr Lys Asp Thr Tyr Asp Ala Leu His Met Gln Ala Leu Pro
        515                 520                 525

Pro Arg
    530

<210> SEQ ID NO 11
<211> LENGTH: 528
<212> TYPE: PRT
<213> ORGANISM: Artificial sequence
<220> FEATURE:
<223> OTHER INFORMATION: S7HINGE construct aa sequence

<400> SEQUENCE: 11

Met Ser Leu Leu Leu Leu Leu Leu Pro Leu Leu Trp Gly Arg Glu Arg
1               5                   10                  15

Val Glu Gly Gln Lys Ser Asn Arg Lys Asp Tyr Ser Leu Thr Met Gln
            20                  25                  30

Ser Ser Val Thr Val Gln Glu Gly Met Cys Val His Val Arg Cys Ser
        35                  40                  45

Phe Ser Tyr Pro Val Asp Ser Gln Thr Asp Ser Asp Pro Val His Gly
        50                  55                  60

Tyr Trp Phe Arg Ala Gly Asn Asp Ile Ser Trp Lys Ala Pro Val Ala
65                  70                  75                  80

Thr Asn Asn Pro Ala Trp Ala Val Gln Glu Glu Thr Arg Asp Arg Phe
                85                  90                  95

His Leu Leu Gly Asp Pro Gln Thr Lys Asn Cys Thr Leu Ser Ile Arg
            100                 105                 110

Asp Ala Arg Met Ser Asp Ala Gly Arg Tyr Phe Phe Arg Met Glu Lys
            115                 120                 125

Gly Asn Ile Lys Trp Asn Tyr Lys Tyr Asp Gln Leu Ser Val Asn Val
        130                 135                 140

Thr Ala Leu Thr His Arg Pro Asn Ile Leu Ile Pro Gly Thr Leu Glu
145                 150                 155                 160

Ser Gly Cys Phe Gln Asn Leu Thr Cys Ser Val Pro Trp Ala Cys Glu
                165                 170                 175

Gln Gly Thr Pro Pro Met Ile Ser Trp Met Gly Thr Ser Val Ser Pro
            180                 185                 190

Leu His Pro Ser Thr Thr Arg Ser Ser Val Leu Thr Leu Ile Pro Gln
        195                 200                 205

Pro Gln His His Gly Thr Ser Leu Thr Cys Gln Val Thr Leu Pro Gly
        210                 215                 220

Ala Gly Val Thr Thr Asn Arg Thr Ile Gln Leu Asn Val Ser Tyr Pro
225                 230                 235                 240

Pro Gln Asn Leu Thr Val Thr Val Phe Gln Gly Glu Gly Thr Ala Ser
                245                 250                 255

Thr Ala Leu Gly Asn Ser Ser Ser Leu Ser Val Leu Glu Gly Gln Ser
            260                 265                 270

Leu Arg Leu Val Cys Ala Val Asp Ser Asn Pro Pro Ala Arg Leu Ser
        275                 280                 285

Trp Thr Trp Arg Ser Leu Thr Leu Tyr Pro Ser Gln Pro Ser Asn Pro
        290                 295                 300
```

-continued

```
Leu Val Leu Glu Leu Gln Val His Leu Gly Asp Glu Gly Glu Phe Thr
305                 310                 315                 320

Cys Arg Ala Gln Asn Ser Leu Gly Ser Gln His Val Ser Leu Asn Leu
                325                 330                 335

Ser Leu Gln Gln Glu Tyr Thr Gly Lys Met Arg Pro Phe Trp Val Leu
                340                 345                 350

Val Val Val Gly Gly Val Leu Ala Cys Tyr Ser Leu Leu Val Thr Val
                355                 360                 365

Ala Phe Ile Ile Phe Trp Val Arg Ser Lys Arg Ser Arg Leu Leu His
                370                 375                 380

Ser Asp Tyr Met Asn Met Thr Pro Arg Arg Pro Gly Pro Thr Arg Lys
385                 390                 395                 400

His Tyr Gln Pro Tyr Ala Pro Pro Arg Asp Phe Ala Ala Tyr Arg Ser
                405                 410                 415

Arg Val Lys Phe Ser Arg Ser Ala Asp Ala Pro Ala Tyr Gln Gln Gly
                420                 425                 430

Gln Asn Gln Leu Tyr Asn Glu Leu Asn Leu Gly Arg Arg Glu Glu Tyr
                435                 440                 445

Asp Val Leu Asp Lys Arg Arg Gly Arg Asp Pro Glu Met Gly Gly Lys
                450                 455                 460

Pro Arg Arg Lys Asn Pro Gln Glu Gly Leu Tyr Asn Glu Leu Gln Lys
465                 470                 475                 480

Asp Lys Met Ala Glu Ala Tyr Ser Glu Ile Gly Met Lys Gly Glu Arg
                485                 490                 495

Arg Arg Gly Lys Gly His Asp Gly Leu Tyr Gln Gly Leu Ser Thr Ala
                500                 505                 510

Thr Lys Asp Thr Tyr Asp Ala Leu His Met Gln Ala Leu Pro Pro Arg
                515                 520                 525
```

```
<210> SEQ ID NO 12
<211> LENGTH: 529
<212> TYPE: PRT
<213> ORGANISM: Artificial sequence
<220> FEATURE:
<223> OTHER INFORMATION: S9TM28 construct aa sequence

<400> SEQUENCE: 12

Met Ser Leu Leu Leu Leu Leu Pro Leu Leu Trp Gly Arg Glu Arg Ala
1                 5                   10                  15

Glu Gly Gln Thr Ser Lys Leu Leu Thr Met Gln Ser Ser Val Thr Val
                20                  25                  30

Gln Glu Gly Leu Cys Val His Val Pro Cys Ser Phe Ser Tyr Pro Ser
                35                  40                  45

His Gly Trp Ile Tyr Pro Gly Pro Val Val His Gly Tyr Trp Phe Arg
        50                  55                  60

Glu Gly Ala Asn Thr Asp Gln Asp Ala Pro Val Ala Thr Asn Asn Pro
65                  70                  75                  80

Ala Arg Ala Val Trp Glu Glu Thr Arg Asp Arg Phe His Leu Leu Gly
                85                  90                  95

Asp Pro His Thr Lys Asn Cys Thr Leu Ser Ile Arg Asp Ala Arg Arg
                100                 105                 110

Ser Asp Ala Gly Arg Tyr Phe Phe Arg Met Glu Lys Gly Ser Ile Lys
                115                 120                 125

Trp Asn Tyr Lys His His Arg Leu Ser Val Asn Val Thr Ala Leu Thr
        130                 135                 140
```

```
His Arg Pro Asn Ile Leu Ile Pro Gly Thr Leu Glu Ser Gly Cys Pro
145                 150                 155                 160

Gln Asn Leu Thr Cys Ser Val Pro Trp Ala Cys Glu Gln Gly Thr Pro
                165                 170                 175

Pro Met Ile Ser Trp Ile Gly Thr Ser Val Ser Pro Leu Asp Pro Ser
                180                 185                 190

Thr Thr Arg Ser Ser Val Leu Thr Leu Ile Pro Gln Pro Gln Asp His
                195                 200                 205

Gly Thr Ser Leu Thr Cys Gln Val Thr Phe Pro Gly Ala Ser Val Thr
        210                 215                 220

Thr Asn Lys Thr Val His Leu Asn Val Ser Tyr Pro Pro Gln Asn Leu
225                 230                 235                 240

Thr Met Thr Val Phe Gln Gly Asp Gly Thr Val Ser Thr Val Leu Gly
                245                 250                 255

Asn Gly Ser Ser Leu Ser Leu Pro Glu Gly Gln Ser Leu Arg Leu Val
                260                 265                 270

Cys Ala Val Asp Ala Val Asp Ser Asn Pro Pro Ala Arg Leu Ser Leu
                275                 280                 285

Ser Trp Arg Gly Leu Thr Leu Cys Pro Ser Gln Pro Ser Asn Pro Gly
        290                 295                 300

Val Leu Glu Leu Pro Trp Val His Leu Arg Asp Ala Ala Glu Phe Thr
305                 310                 315                 320

Cys Arg Ala Gln Asn Pro Leu Gly Ser Gln Gln Val Tyr Leu Asn Val
                325                 330                 335

Ser Leu Gln Ser Lys Ala Thr Ser Gly Val Thr Gln Gly Phe Trp Val
                340                 345                 350

Leu Val Val Val Gly Gly Val Leu Ala Cys Tyr Ser Leu Leu Val Thr
                355                 360                 365

Val Ala Phe Ile Ile Phe Trp Val Arg Ser Lys Arg Ser Arg Leu Leu
        370                 375                 380

His Ser Asp Tyr Met Asn Met Thr Pro Arg Arg Pro Gly Pro Thr Arg
385                 390                 395                 400

Lys His Tyr Gln Pro Tyr Ala Pro Pro Arg Asp Phe Ala Ala Tyr Arg
                405                 410                 415

Ser Arg Val Lys Phe Ser Arg Ser Ala Asp Ala Pro Ala Tyr Gln Gln
                420                 425                 430

Gly Gln Asn Gln Leu Tyr Asn Glu Leu Asn Leu Gly Arg Arg Glu Glu
                435                 440                 445

Tyr Asp Val Leu Asp Lys Arg Arg Gly Arg Asp Pro Glu Met Gly Gly
        450                 455                 460

Lys Pro Arg Arg Lys Asn Pro Gln Glu Gly Leu Tyr Asn Glu Leu Gln
465                 470                 475                 480

Lys Asp Lys Met Ala Glu Ala Tyr Ser Glu Ile Gly Met Lys Gly Glu
                485                 490                 495

Arg Arg Arg Gly Lys Gly His Asp Gly Leu Tyr Gln Gly Leu Ser Thr
                500                 505                 510

Ala Thr Lys Asp Thr Tyr Asp Ala Leu His Met Gln Ala Leu Pro Pro
                515                 520                 525

Arg
```

<210> SEQ ID NO 13
<211> LENGTH: 524
<212> TYPE: PRT
<213> ORGANISM: Artificial sequence
<220> FEATURE:
<223> OTHER INFORMATION: S9TMSG construct aa sequence

<400> SEQUENCE: 13

```
Met Ser Leu Leu Leu Leu Leu Pro Leu Leu Trp Gly Arg Glu Arg Ala
1               5                   10                  15

Glu Gly Gln Thr Ser Lys Leu Leu Thr Met Gln Ser Ser Val Thr Val
            20                  25                  30

Gln Glu Gly Leu Cys Val His Val Pro Cys Ser Phe Ser Tyr Pro Ser
        35                  40                  45

His Gly Trp Ile Tyr Pro Gly Pro Val Val His Gly Tyr Trp Phe Arg
    50                  55                  60

Glu Gly Ala Asn Thr Asp Gln Asp Ala Pro Val Ala Thr Asn Asn Pro
65                  70                  75                  80

Ala Arg Ala Val Trp Glu Glu Thr Arg Asp Arg Phe His Leu Leu Gly
                85                  90                  95

Asp Pro His Thr Lys Asn Cys Thr Leu Ser Ile Arg Asp Ala Arg Arg
            100                 105                 110

Ser Asp Ala Gly Arg Tyr Phe Phe Arg Met Glu Lys Gly Ser Ile Lys
        115                 120                 125

Trp Asn Tyr Lys His His Arg Leu Ser Val Asn Val Thr Ala Leu Thr
    130                 135                 140

His Arg Pro Asn Ile Leu Ile Pro Gly Thr Leu Glu Ser Gly Cys Pro
145                 150                 155                 160

Gln Asn Leu Thr Cys Ser Val Pro Trp Ala Cys Glu Gln Gly Thr Pro
                165                 170                 175

Pro Met Ile Ser Trp Ile Gly Thr Ser Val Ser Pro Leu Asp Pro Ser
            180                 185                 190

Thr Thr Arg Ser Ser Val Leu Thr Leu Ile Pro Gln Pro Gln Asp His
            195                 200                 205

Gly Thr Ser Leu Thr Cys Gln Val Thr Phe Pro Gly Ala Ser Val Thr
    210                 215                 220

Thr Asn Lys Thr Val His Leu Asn Val Ser Tyr Pro Pro Gln Asn Leu
225                 230                 235                 240

Thr Met Thr Val Phe Gln Gly Asp Gly Thr Val Ser Thr Val Leu Gly
                245                 250                 255

Asn Gly Ser Ser Leu Ser Leu Pro Glu Gly Gln Ser Leu Arg Leu Val
            260                 265                 270

Cys Ala Val Asp Ala Val Asp Ser Asn Pro Pro Ala Arg Leu Ser Leu
        275                 280                 285

Ser Trp Arg Gly Leu Thr Leu Cys Pro Ser Gln Pro Ser Asn Pro Gly
    290                 295                 300

Val Leu Glu Leu Pro Trp Val His Leu Arg Asp Ala Ala Glu Phe Thr
305                 310                 315                 320

Cys Arg Ala Gln Asn Pro Leu Gly Ser Gln Gln Val Tyr Leu Asn Val
                325                 330                 335

Ser Leu Gln Ser Lys Ala Thr Ser Gly Val Thr Gln Gly Val Val Gly
            340                 345                 350

Gly Ala Gly Ala Thr Ala Leu Val Phe Leu Ser Phe Cys Val Ile Phe
        355                 360                 365

Val Val Val Arg Ser Lys Arg Ser Arg Leu Leu His Ser Asp Tyr Met
    370                 375                 380

Asn Met Thr Pro Arg Arg Pro Gly Pro Thr Arg Lys His Tyr Gln Pro
385                 390                 395                 400
```

```
Tyr Ala Pro Pro Arg Asp Phe Ala Ala Tyr Arg Ser Arg Val Lys Phe
            405             410             415

Ser Arg Ser Ala Asp Ala Pro Ala Tyr Gln Gln Gly Gln Asn Gln Leu
            420             425             430

Tyr Asn Glu Leu Asn Leu Gly Arg Arg Glu Glu Tyr Asp Val Leu Asp
            435             440             445

Lys Arg Arg Gly Arg Asp Pro Glu Met Gly Gly Lys Pro Arg Arg Lys
            450             455             460

Asn Pro Gln Glu Gly Leu Tyr Asn Glu Leu Gln Lys Asp Lys Met Ala
465             470             475             480

Glu Ala Tyr Ser Glu Ile Gly Met Lys Gly Glu Arg Arg Arg Gly Lys
            485             490             495

Gly His Asp Gly Leu Tyr Gln Gly Leu Ser Thr Ala Thr Lys Asp Thr
            500             505             510

Tyr Asp Ala Leu His Met Gln Ala Leu Pro Pro Arg
            515             520
```

```
<210> SEQ ID NO 14
<211> LENGTH: 533
<212> TYPE: PRT
<213> ORGANISM: Artificial sequence
<220> FEATURE:
<223> OTHER INFORMATION: S9-PSKP construct aa sequence

<400> SEQUENCE: 14

Met Ser Leu Leu Leu Leu Leu Pro Leu Leu Trp Gly Arg Glu Arg Ala
1               5               10              15

Glu Gly Gln Thr Ser Lys Leu Leu Thr Met Gln Ser Ser Val Thr Val
            20              25              30

Gln Glu Gly Leu Cys Val His Val Pro Cys Ser Phe Ser Tyr Pro Ser
            35              40              45

His Gly Trp Ile Tyr Pro Gly Pro Val Val His Gly Tyr Trp Phe Arg
            50              55              60

Glu Gly Ala Asn Thr Asp Gln Asp Ala Pro Val Ala Thr Asn Asn Pro
65              70              75              80

Ala Arg Ala Val Trp Glu Glu Thr Arg Asp Arg Phe His Leu Leu Gly
            85              90              95

Asp Pro His Thr Lys Asn Cys Thr Leu Ser Ile Arg Asp Ala Arg Arg
            100             105             110

Ser Asp Ala Gly Arg Tyr Phe Phe Arg Met Glu Lys Gly Ser Ile Lys
            115             120             125

Trp Asn Tyr Lys His His Arg Leu Ser Val Asn Val Thr Ala Leu Thr
            130             135             140

His Arg Pro Asn Ile Leu Ile Pro Gly Thr Leu Glu Ser Gly Cys Pro
145             150             155             160

Gln Asn Leu Thr Cys Ser Val Pro Trp Ala Cys Glu Gln Gly Thr Pro
            165             170             175

Pro Met Ile Ser Trp Ile Gly Thr Ser Val Ser Pro Leu Asp Pro Ser
            180             185             190

Thr Thr Arg Ser Ser Val Leu Thr Leu Ile Pro Gln Pro Gln Asp His
            195             200             205

Gly Thr Ser Leu Thr Cys Gln Val Thr Phe Pro Gly Ala Ser Val Thr
            210             215             220

Thr Asn Lys Thr Val His Leu Asn Val Ser Tyr Pro Pro Gln Asn Leu
225             230             235             240
```

-continued

```
Thr Met Thr Val Phe Gln Gly Asp Gly Thr Val Ser Thr Val Leu Gly
            245                 250                 255

Asn Gly Ser Ser Leu Ser Leu Pro Glu Gly Gln Ser Leu Arg Leu Val
            260                 265                 270

Cys Ala Val Asp Ala Val Asp Ser Asn Pro Pro Ala Arg Leu Ser Leu
            275                 280                 285

Ser Trp Arg Gly Leu Thr Leu Cys Pro Ser Gln Pro Ser Asn Pro Gly
            290                 295                 300

Val Leu Glu Leu Pro Trp Val His Leu Arg Asp Ala Ala Glu Phe Thr
305                 310                 315                 320

Cys Arg Ala Gln Asn Pro Leu Gly Ser Gln Gln Val Tyr Leu Asn Val
            325                 330                 335

Ser Leu Gln Ser Lys Ala Thr Ser Gly Val Thr Gln Gly Pro Ser Lys
            340                 345                 350

Pro Phe Trp Val Leu Val Val Val Gly Gly Val Leu Ala Cys Tyr Ser
            355                 360                 365

Leu Leu Val Thr Val Ala Phe Ile Ile Phe Trp Val Arg Ser Lys Arg
            370                 375                 380

Ser Arg Leu Leu His Ser Asp Tyr Met Asn Met Thr Pro Arg Arg Pro
385                 390                 395                 400

Gly Pro Thr Arg Lys His Tyr Gln Pro Tyr Ala Pro Pro Arg Asp Phe
            405                 410                 415

Ala Ala Tyr Arg Ser Arg Val Lys Phe Ser Arg Ser Ala Asp Ala Pro
            420                 425                 430

Ala Tyr Gln Gln Gly Gln Asn Gln Leu Tyr Asn Glu Leu Asn Leu Gly
            435                 440                 445

Arg Arg Glu Glu Tyr Asp Val Leu Asp Lys Arg Arg Gly Arg Asp Pro
            450                 455                 460

Glu Met Gly Gly Lys Pro Arg Arg Lys Asn Pro Gln Glu Gly Leu Tyr
465                 470                 475                 480

Asn Glu Leu Gln Lys Asp Lys Met Ala Glu Ala Tyr Ser Glu Ile Gly
            485                 490                 495

Met Lys Gly Glu Arg Arg Arg Gly Lys Gly His Asp Gly Leu Tyr Gln
            500                 505                 510

Gly Leu Ser Thr Ala Thr Lys Asp Thr Tyr Asp Ala Leu His Met Gln
            515                 520                 525

Ala Leu Pro Pro Arg
            530
```

<210> SEQ ID NO 15
<211> LENGTH: 341
<212> TYPE: PRT
<213> ORGANISM: Artificial sequence
<220> FEATURE:
<223> OTHER INFORMATION: S7D1 construct aa sequence

<400> SEQUENCE: 15

```
Met Ser Leu Leu Leu Leu Leu Leu Pro Leu Leu Trp Gly Arg Glu Arg
1               5                   10                  15

Val Glu Gly Gln Lys Ser Asn Arg Lys Asp Tyr Ser Leu Thr Met Gln
            20                  25                  30

Ser Ser Val Thr Val Gln Glu Gly Met Cys Val His Val Arg Cys Ser
            35                  40                  45

Phe Ser Tyr Pro Val Asp Ser Gln Thr Asp Ser Asp Pro Val His Gly
            50                  55                  60
```

```
Tyr Trp Phe Arg Ala Gly Asn Asp Ile Ser Trp Lys Ala Pro Val Ala
65                  70                  75                  80

Thr Asn Asn Pro Ala Trp Ala Val Gln Glu Glu Thr Arg Asp Arg Phe
                85                  90                  95

His Leu Leu Gly Asp Pro Gln Thr Lys Asn Cys Thr Leu Ser Ile Arg
            100                 105                 110

Asp Ala Arg Met Ser Asp Ala Gly Arg Tyr Phe Phe Arg Met Glu Lys
            115                 120                 125

Gly Asn Ile Lys Trp Asn Tyr Lys Tyr Asp Gln Leu Ser Val Asn Val
            130                 135                 140

Thr Ala Leu Thr Gly Lys Met Arg Pro Val Ser Gly Val Leu Leu Ala
145                 150                 155                 160

Ser Phe Trp Val Leu Val Val Val Gly Gly Val Leu Ala Cys Tyr Ser
                165                 170                 175

Leu Leu Val Thr Val Ala Phe Ile Ile Phe Trp Val Arg Ser Lys Arg
                180                 185                 190

Ser Arg Leu Leu His Ser Asp Tyr Met Asn Met Thr Pro Arg Arg Pro
            195                 200                 205

Gly Pro Thr Arg Lys His Tyr Gln Pro Tyr Ala Pro Pro Arg Asp Phe
            210                 215                 220

Ala Ala Tyr Arg Ser Arg Val Lys Phe Ser Arg Ser Ala Asp Ala Pro
225                 230                 235                 240

Ala Tyr Gln Gln Gly Gln Asn Gln Leu Tyr Asn Glu Leu Asn Leu Gly
                245                 250                 255

Arg Arg Glu Glu Tyr Asp Val Leu Asp Lys Arg Arg Gly Arg Asp Pro
            260                 265                 270

Glu Met Gly Gly Lys Pro Arg Arg Lys Asn Pro Gln Glu Gly Leu Tyr
            275                 280                 285

Asn Glu Leu Gln Lys Asp Lys Met Ala Glu Ala Tyr Ser Glu Ile Gly
            290                 295                 300

Met Lys Gly Glu Arg Arg Arg Gly Lys Gly His Asp Gly Leu Tyr Gln
305                 310                 315                 320

Gly Leu Ser Thr Ala Thr Lys Asp Thr Tyr Asp Ala Leu His Met Gln
                325                 330                 335

Ala Leu Pro Pro Arg
            340

<210> SEQ ID NO 16
<211> LENGTH: 445
<212> TYPE: PRT
<213> ORGANISM: Artificial sequence
<220> FEATURE:
<223> OTHER INFORMATION: S7D1+2 construct aa sequence

<400> SEQUENCE: 16

Met Ser Leu Leu Leu Leu Leu Leu Pro Leu Leu Trp Gly Arg Glu Arg
1               5                   10                  15

Val Glu Gly Gln Lys Ser Asn Arg Lys Asp Tyr Ser Leu Thr Met Gln
                20                  25                  30

Ser Ser Val Thr Val Gln Glu Gly Met Cys Val His Val Arg Cys Ser
            35                  40                  45

Phe Ser Tyr Pro Val Asp Ser Gln Thr Asp Ser Asp Pro Val His Gly
        50                  55                  60

Tyr Trp Phe Arg Ala Gly Asn Asp Ile Ser Trp Lys Ala Pro Val Ala
65                  70                  75                  80
```

```
Thr Asn Asn Pro Ala Trp Ala Val Gln Glu Glu Thr Arg Asp Arg Phe
            85                  90                  95

His Leu Leu Gly Asp Pro Gln Thr Lys Asn Cys Thr Leu Ser Ile Arg
            100                 105                 110

Asp Ala Arg Met Ser Asp Ala Gly Arg Tyr Phe Phe Arg Met Glu Lys
            115                 120                 125

Gly Asn Ile Lys Trp Asn Tyr Lys Tyr Asp Gln Leu Ser Val Asn Val
            130                 135                 140

Thr Ala Leu Thr His Arg Pro Asn Ile Leu Ile Pro Gly Thr Leu Glu
145                 150                 155                 160

Ser Gly Cys Phe Gln Asn Leu Thr Cys Ser Val Pro Trp Ala Cys Glu
            165                 170                 175

Gln Gly Thr Pro Pro Met Ile Ser Trp Met Gly Thr Ser Val Ser Pro
            180                 185                 190

Leu His Pro Ser Thr Thr Arg Ser Ser Val Leu Thr Leu Ile Pro Gln
            195                 200                 205

Pro Gln His His Gly Thr Ser Leu Thr Cys Gln Val Thr Leu Pro Gly
            210                 215                 220

Ala Gly Val Thr Thr Asn Arg Thr Ile Gln Leu Asn Val Ser Tyr Pro
225                 230                 235                 240

Pro Gln Asn Leu Thr Val Thr Val Phe Gln Gly Thr Gly Lys Met Arg
            245                 250                 255

Pro Val Ser Gly Val Leu Leu Ala Ser Phe Trp Val Leu Val Val Val
            260                 265                 270

Gly Gly Val Leu Ala Cys Tyr Ser Leu Leu Val Thr Val Ala Phe Ile
            275                 280                 285

Ile Phe Trp Val Arg Ser Lys Arg Ser Arg Leu Leu His Ser Asp Tyr
290                 295                 300

Met Asn Met Thr Pro Arg Arg Pro Gly Pro Thr Arg Lys His Tyr Gln
305                 310                 315                 320

Pro Tyr Ala Pro Pro Arg Asp Phe Ala Ala Tyr Arg Ser Arg Val Lys
            325                 330                 335

Phe Ser Arg Ser Ala Asp Ala Pro Ala Tyr Gln Gln Gly Gln Asn Gln
            340                 345                 350

Leu Tyr Asn Glu Leu Asn Leu Gly Arg Arg Glu Glu Tyr Asp Val Leu
            355                 360                 365

Asp Lys Arg Arg Gly Arg Asp Pro Glu Met Gly Gly Lys Pro Arg Arg
            370                 375                 380

Lys Asn Pro Gln Glu Gly Leu Tyr Asn Glu Leu Gln Lys Asp Lys Met
385                 390                 395                 400

Ala Glu Ala Tyr Ser Glu Ile Gly Met Lys Gly Glu Arg Arg Arg Gly
            405                 410                 415

Lys Gly His Asp Gly Leu Tyr Gln Gly Leu Ser Thr Ala Thr Lys Asp
            420                 425                 430

Thr Tyr Asp Ala Leu His Met Gln Ala Leu Pro Pro Arg
            435                 440                 445
```

```
<210> SEQ ID NO 17
<211> LENGTH: 446
<212> TYPE: PRT
<213> ORGANISM: Artificial sequence
<220> FEATURE:
<223> OTHER INFORMATION: S7D1+3 construct aa sequence

<400> SEQUENCE: 17
```

```
Met Ser Leu Leu Leu Leu Leu Leu Pro Leu Leu Trp Gly Arg Glu Arg
1               5                   10                  15

Val Glu Gly Gln Lys Ser Asn Arg Lys Asp Tyr Ser Leu Thr Met Gln
                20                  25                  30

Ser Ser Val Thr Val Gln Glu Gly Met Cys Val His Val Arg Cys Ser
            35                  40                  45

Phe Ser Tyr Pro Val Asp Ser Gln Thr Asp Ser Asp Pro Val His Gly
        50                  55                  60

Tyr Trp Phe Arg Ala Gly Asn Asp Ile Ser Trp Lys Ala Pro Val Ala
65                  70                  75                  80

Thr Asn Asn Pro Ala Trp Ala Val Gln Glu Glu Thr Arg Asp Arg Phe
                85                  90                  95

His Leu Leu Gly Asp Pro Gln Thr Lys Asn Cys Thr Leu Ser Ile Arg
            100                 105                 110

Asp Ala Arg Met Ser Asp Ala Gly Arg Tyr Phe Phe Arg Met Glu Lys
            115                 120                 125

Gly Asn Ile Lys Trp Asn Tyr Lys Tyr Asp Gln Leu Ser Val Asn Val
        130                 135                 140

Thr Ala Leu Thr Tyr Pro Pro Gln Asn Leu Thr Val Thr Val Phe Gln
145                 150                 155                 160

Gly Glu Gly Thr Ala Ser Thr Ala Leu Gly Asn Ser Ser Ser Leu Ser
                165                 170                 175

Val Leu Glu Gly Gln Ser Leu Arg Leu Val Cys Ala Val Asp Ser Asn
            180                 185                 190

Pro Pro Ala Arg Leu Ser Trp Thr Trp Arg Ser Leu Thr Leu Tyr Pro
            195                 200                 205

Ser Gln Pro Ser Asn Pro Leu Val Leu Glu Leu Gln Val His Leu Gly
        210                 215                 220

Asp Glu Gly Glu Phe Thr Cys Arg Ala Gln Asn Ser Leu Gly Ser Gln
225                 230                 235                 240

His Val Ser Leu Asn Leu Ser Leu Gln Gln Glu Tyr Thr Gly Lys Met
                245                 250                 255

Arg Pro Val Ser Gly Val Leu Leu Ala Ser Phe Trp Val Leu Val Val
            260                 265                 270

Val Gly Gly Val Leu Ala Cys Tyr Ser Leu Leu Val Thr Val Ala Phe
            275                 280                 285

Ile Ile Phe Trp Val Arg Ser Lys Arg Ser Arg Leu Leu His Ser Asp
        290                 295                 300

Tyr Met Asn Met Thr Pro Arg Arg Pro Gly Pro Thr Arg Lys His Tyr
305                 310                 315                 320

Gln Pro Tyr Ala Pro Pro Arg Asp Phe Ala Ala Tyr Arg Ser Arg Val
                325                 330                 335

Lys Phe Ser Arg Ser Ala Asp Ala Pro Ala Tyr Gln Gln Gly Gln Asn
            340                 345                 350

Gln Leu Tyr Asn Glu Leu Asn Leu Gly Arg Arg Glu Glu Tyr Asp Val
            355                 360                 365

Leu Asp Lys Arg Arg Gly Arg Asp Pro Glu Met Gly Gly Lys Pro Arg
        370                 375                 380

Arg Lys Asn Pro Gln Glu Gly Leu Tyr Asn Glu Leu Gln Lys Asp Lys
385                 390                 395                 400

Met Ala Glu Ala Tyr Ser Glu Ile Gly Met Lys Gly Glu Arg Arg Arg
                405                 410                 415
```

-continued

```
Gly Lys Gly His Asp Gly Leu Tyr Gln Gly Leu Ser Thr Ala Thr Lys
            420                 425                 430

Asp Thr Tyr Asp Ala Leu His Met Gln Ala Leu Pro Pro Arg
        435                 440                 445

<210> SEQ ID NO 18
<211> LENGTH: 424
<212> TYPE: PRT
<213> ORGANISM: Artificial sequence
<220> FEATURE:
<223> OTHER INFORMATION: S728 CSR construct aa sequence

<400> SEQUENCE: 18

Met Ser Leu Leu Leu Leu Leu Leu Pro Leu Leu Trp Gly Arg Glu Arg
1               5                   10                  15

Val Glu Gly Gln Lys Ser Asn Arg Lys Asp Tyr Ser Leu Thr Met Gln
            20                  25                  30

Ser Ser Val Thr Val Gln Glu Gly Met Cys Val His Val Arg Cys Ser
        35                  40                  45

Phe Ser Tyr Pro Val Asp Ser Gln Thr Asp Ser Asp Pro Val His Gly
    50                  55                  60

Tyr Trp Phe Arg Ala Gly Asn Asp Ile Ser Trp Lys Ala Pro Val Ala
65                  70                  75                  80

Thr Asn Asn Pro Ala Trp Ala Val Gln Glu Glu Thr Arg Asp Arg Phe
                85                  90                  95

His Leu Leu Gly Asp Pro Gln Thr Lys Asn Cys Thr Leu Ser Ile Arg
            100                 105                 110

Asp Ala Arg Met Ser Asp Ala Gly Arg Tyr Phe Phe Arg Met Glu Lys
            115                 120                 125

Gly Asn Ile Lys Trp Asn Tyr Lys Tyr Asp Gln Leu Ser Val Asn Val
        130                 135                 140

Thr Ala Leu Thr His Arg Pro Asn Ile Leu Ile Pro Gly Thr Leu Glu
145                 150                 155                 160

Ser Gly Cys Phe Gln Asn Leu Thr Cys Ser Val Pro Trp Ala Cys Glu
                165                 170                 175

Gln Gly Thr Pro Pro Met Ile Ser Trp Met Gly Thr Ser Val Ser Pro
            180                 185                 190

Leu His Pro Ser Thr Thr Arg Ser Ser Val Leu Thr Leu Ile Pro Gln
            195                 200                 205

Pro Gln His His Gly Thr Ser Leu Thr Cys Gln Val Thr Leu Pro Gly
    210                 215                 220

Ala Gly Val Thr Thr Asn Arg Thr Ile Gln Leu Asn Val Ser Tyr Pro
225                 230                 235                 240

Pro Gln Asn Leu Thr Val Thr Val Phe Gln Gly Glu Gly Thr Ala Ser
            245                 250                 255

Thr Ala Leu Gly Asn Ser Ser Ser Leu Ser Val Leu Glu Gly Gln Ser
            260                 265                 270

Leu Arg Leu Val Cys Ala Val Asp Ser Asn Pro Pro Ala Arg Leu Ser
            275                 280                 285

Trp Thr Trp Arg Ser Leu Thr Leu Tyr Pro Ser Gln Pro Ser Asn Pro
    290                 295                 300

Leu Val Leu Glu Leu Gln Val His Leu Gly Asp Glu Gly Glu Phe Thr
305                 310                 315                 320

Cys Arg Ala Gln Asn Ser Leu Gly Ser Gln His Val Ser Leu Asn Leu
            325                 330                 335
```

-continued

```
Ser Leu Gln Gln Glu Tyr Thr Gly Lys Met Arg Pro Val Ser Gly Val
            340                 345                 350

Leu Leu Ala Ser Phe Trp Val Leu Val Val Gly Gly Val Leu Ala
            355                 360                 365

Cys Tyr Ser Leu Leu Val Thr Val Ala Phe Ile Ile Phe Trp Val Arg
    370                 375                 380

Ser Lys Arg Ser Arg Leu Leu His Ser Asp Tyr Met Asn Met Thr Pro
385                 390                 395                 400

Arg Arg Pro Gly Pro Thr Arg Lys His Tyr Gln Pro Tyr Ala Pro Pro
                405                 410                 415

Arg Asp Phe Ala Ala Tyr Arg Ser
            420

<210> SEQ ID NO 19
<211> LENGTH: 417
<212> TYPE: PRT
<213> ORGANISM: Artificial sequence
<220> FEATURE:
<223> OTHER INFORMATION: S928 CSR construct aa sequence

<400> SEQUENCE: 19

Met Ser Leu Leu Leu Leu Leu Pro Leu Leu Trp Gly Arg Glu Arg Ala
1               5                   10                  15

Glu Gly Gln Thr Ser Lys Leu Leu Thr Met Gln Ser Ser Val Thr Val
            20                  25                  30

Gln Glu Gly Leu Cys Val His Val Pro Cys Ser Phe Ser Tyr Pro Ser
            35                  40                  45

His Gly Trp Ile Tyr Pro Gly Pro Val Val His Gly Tyr Trp Phe Arg
    50                  55                  60

Glu Gly Ala Asn Thr Asp Gln Asp Ala Pro Val Ala Thr Asn Asn Pro
65                  70                  75                  80

Ala Arg Ala Val Trp Glu Glu Thr Arg Asp Arg Phe His Leu Leu Gly
                85                  90                  95

Asp Pro His Thr Lys Asn Cys Thr Leu Ser Ile Arg Asp Ala Arg Arg
            100                 105                 110

Ser Asp Ala Gly Arg Tyr Phe Phe Arg Met Glu Lys Gly Ser Ile Lys
            115                 120                 125

Trp Asn Tyr Lys His His Arg Leu Ser Val Asn Val Thr Ala Leu Thr
    130                 135                 140

His Arg Pro Asn Ile Leu Ile Pro Gly Thr Leu Glu Ser Gly Cys Pro
145                 150                 155                 160

Gln Asn Leu Thr Cys Ser Val Pro Trp Ala Cys Glu Gln Gly Thr Pro
                165                 170                 175

Pro Met Ile Ser Trp Ile Gly Thr Ser Val Ser Pro Leu Asp Pro Ser
            180                 185                 190

Thr Thr Arg Ser Ser Val Leu Thr Leu Ile Pro Gln Pro Gln Asp His
            195                 200                 205

Gly Thr Ser Leu Thr Cys Gln Val Thr Phe Pro Gly Ala Ser Val Thr
            210                 215                 220

Thr Asn Lys Thr Val His Leu Asn Val Ser Tyr Pro Pro Gln Asn Leu
225                 230                 235                 240

Thr Met Thr Val Phe Gln Gly Asp Gly Thr Val Ser Thr Val Leu Gly
                245                 250                 255

Asn Gly Ser Ser Leu Ser Leu Pro Glu Gly Gln Ser Leu Arg Leu Val
            260                 265                 270
```

-continued

```
Cys Ala Val Asp Ala Val Asp Ser Asn Pro Pro Ala Arg Leu Ser Leu
        275             280             285

Ser Trp Arg Gly Leu Thr Leu Cys Pro Ser Gln Pro Ser Asn Pro Gly
    290             295             300

Val Leu Glu Leu Pro Trp Val His Leu Arg Asp Ala Ala Glu Phe Thr
305             310             315             320

Cys Arg Ala Gln Asn Pro Leu Gly Ser Gln Gln Val Tyr Leu Asn Val
            325             330             335

Ser Leu Gln Ser Lys Ala Thr Ser Gly Val Thr Gln Gly Phe Trp Val
            340             345             350

Leu Val Val Val Gly Gly Val Leu Ala Cys Tyr Ser Leu Leu Val Thr
            355             360             365

Val Ala Phe Ile Ile Phe Trp Val Arg Ser Lys Arg Ser Arg Leu Leu
    370             375             380

His Ser Asp Tyr Met Asn Met Thr Pro Arg Arg Pro Gly Pro Thr Arg
385             390             395             400

Lys His Tyr Gln Pro Tyr Ala Pro Pro Arg Asp Phe Ala Ala Tyr Arg
            405             410             415

Ser
```

```
<210> SEQ ID NO 20
<211> LENGTH: 421
<212> TYPE: PRT
<213> ORGANISM: Artificial sequence
<220> FEATURE:
<223> OTHER INFORMATION: S928_B CSR construct aa sequence

<400> SEQUENCE: 20
```

```
Met Ser Ala Leu Pro Val Thr Ala Leu Leu Leu Pro Leu Ala Leu Leu
1               5               10              15

Leu His Ala Ala Arg Pro Gln Thr Ser Lys Leu Leu Thr Met Gln Ser
            20              25              30

Ser Val Thr Val Gln Glu Gly Leu Cys Val His Val Pro Cys Ser Phe
            35              40              45

Ser Tyr Pro Ser His Gly Trp Ile Tyr Pro Gly Pro Val Val His Gly
    50              55              60

Tyr Trp Phe Arg Glu Gly Ala Asn Thr Asp Gln Asp Ala Pro Val Ala
65              70              75              80

Thr Asn Asn Pro Ala Arg Ala Val Trp Glu Glu Thr Arg Asp Arg Phe
            85              90              95

His Leu Leu Gly Asp Pro His Thr Lys Asn Cys Thr Leu Ser Ile Arg
            100             105             110

Asp Ala Arg Arg Ser Asp Ala Gly Arg Tyr Phe Phe Arg Met Glu Lys
            115             120             125

Gly Ser Ile Lys Trp Asn Tyr Lys His His Arg Leu Ser Val Asn Val
    130             135             140

Thr Ala Leu Thr His Arg Pro Asn Ile Leu Ile Pro Gly Thr Leu Glu
145             150             155             160

Ser Gly Cys Pro Gln Asn Leu Thr Cys Ser Val Pro Trp Ala Cys Glu
            165             170             175

Gln Gly Thr Pro Pro Met Ile Ser Trp Ile Gly Thr Ser Val Ser Pro
            180             185             190

Leu Asp Pro Ser Thr Thr Arg Ser Ser Val Leu Thr Leu Ile Pro Gln
            195             200             205

Pro Gln Asp His Gly Thr Ser Leu Thr Cys Gln Val Thr Phe Pro Gly
```

-continued

```
        210             215             220

Ala Ser Val Thr Thr Asn Lys Thr Val His Leu Asn Val Ser Tyr Pro
225             230             235             240

Pro Gln Asn Leu Thr Met Thr Val Phe Gln Gly Asp Gly Thr Val Ser
            245             250             255

Thr Val Leu Gly Asn Gly Ser Ser Leu Ser Leu Pro Glu Gly Gln Ser
            260             265             270

Leu Arg Leu Val Cys Ala Val Asp Ala Val Asp Ser Asn Pro Pro Ala
            275             280             285

Arg Leu Ser Leu Ser Trp Arg Gly Leu Thr Leu Cys Pro Ser Gln Pro
            290             295             300

Ser Asn Pro Gly Val Leu Glu Leu Pro Trp Val His Leu Arg Asp Ala
305             310             315             320

Ala Glu Phe Thr Cys Arg Ala Gln Asn Pro Leu Gly Ser Gln Gln Val
            325             330             335

Tyr Leu Asn Val Ser Leu Gln Ser Lys Ala Thr Ser Gly Val Thr Gln
            340             345             350

Gly Phe Trp Val Leu Val Val Val Gly Gly Val Leu Ala Cys Tyr Ser
            355             360             365

Leu Leu Val Thr Val Ala Phe Ile Ile Phe Trp Val Arg Ser Lys Arg
            370             375             380

Ser Arg Leu Leu His Ser Asp Tyr Met Asn Met Thr Pro Arg Arg Pro
385             390             395             400

Gly Pro Thr Arg Lys His Tyr Gln Pro Tyr Ala Pro Pro Arg Asp Phe
            405             410             415

Ala Ala Tyr Arg Ser
            420

<210> SEQ ID NO 21
<211> LENGTH: 448
<212> TYPE: PRT
<213> ORGANISM: Artificial sequence
<220> FEATURE:
<223> OTHER INFORMATION: S928_C CSR construct aa sequence

<400> SEQUENCE: 21

Met Ser Ala Leu Pro Val Thr Ala Leu Leu Leu Pro Leu Ala Leu Leu
1               5               10              15

Leu His Ala Ala Arg Pro Gln Thr Ser Lys Leu Leu Thr Met Gln Ser
                20              25              30

Ser Val Thr Val Gln Glu Gly Leu Cys Val His Val Pro Cys Ser Phe
            35              40              45

Ser Tyr Pro Ser His Gly Trp Ile Tyr Pro Gly Pro Val Val His Gly
            50              55              60

Tyr Trp Phe Arg Glu Gly Ala Asn Thr Asp Gln Asp Ala Pro Val Ala
65              70              75              80

Thr Asn Asn Pro Ala Arg Ala Val Trp Glu Glu Thr Arg Asp Arg Phe
                85              90              95

His Leu Leu Gly Asp Pro His Thr Lys Asn Cys Thr Leu Ser Ile Arg
            100             105             110

Asp Ala Arg Arg Ser Asp Ala Gly Arg Tyr Phe Phe Arg Met Glu Lys
            115             120             125

Gly Ser Ile Lys Trp Asn Tyr Lys His His Arg Leu Ser Val Asn Val
            130             135             140

Thr Ala Leu Thr His Arg Pro Asn Ile Leu Ile Pro Gly Thr Leu Glu
```

```
                145                 150                 155                 160

Ser Gly Cys Pro Gln Asn Leu Thr Cys Ser Val Pro Trp Ala Cys Glu
                        165                 170                 175

Gln Gly Thr Pro Pro Met Ile Ser Trp Ile Gly Thr Ser Val Ser Pro
                        180                 185                 190

Leu Asp Pro Ser Thr Thr Arg Ser Ser Val Leu Thr Leu Ile Pro Gln
                        195                 200                 205

Pro Gln Asp His Gly Thr Ser Leu Thr Cys Gln Val Thr Phe Pro Gly
                210                 215                 220

Ala Ser Val Thr Thr Asn Lys Thr Val His Leu Asn Val Ser Tyr Pro
        225                 230                 235                 240

Pro Gln Asn Leu Thr Met Thr Val Phe Gln Gly Asp Gly Thr Val Ser
                        245                 250                 255

Thr Val Leu Gly Asn Gly Ser Ser Leu Ser Leu Pro Glu Gly Gln Ser
                        260                 265                 270

Leu Arg Leu Val Cys Ala Val Asp Ala Val Asp Ser Asn Pro Pro Ala
                        275                 280                 285

Arg Leu Ser Leu Ser Trp Arg Gly Leu Thr Leu Cys Pro Ser Gln Pro
                290                 295                 300

Ser Asn Pro Gly Val Leu Glu Leu Pro Trp Val His Leu Arg Asp Ala
        305                 310                 315                 320

Ala Glu Phe Thr Cys Arg Ala Gln Asn Pro Leu Gly Ser Gln Gln Val
                        325                 330                 335

Tyr Leu Asn Val Ser Ile Glu Val Met Tyr Pro Pro Pro Tyr Leu Asp
                        340                 345                 350

Asn Glu Lys Ser Asn Gly Thr Ile Ile His Val Lys Gly Lys His Leu
                        355                 360                 365

Cys Pro Ser Pro Leu Phe Pro Gly Pro Ser Lys Pro Phe Trp Val Leu
                370                 375                 380

Val Val Val Gly Gly Val Leu Ala Cys Tyr Ser Leu Leu Val Thr Val
        385                 390                 395                 400

Ala Phe Ile Ile Phe Trp Val Arg Ser Lys Arg Ser Arg Leu Leu His
                        405                 410                 415

Ser Asp Tyr Met Asn Met Thr Pro Arg Arg Pro Gly Pro Thr Arg Lys
                        420                 425                 430

His Tyr Gln Pro Tyr Ala Pro Pro Arg Asp Phe Ala Ala Tyr Arg Ser
                        435                 440                 445

<210> SEQ ID NO 22
        <211> LENGTH: 449
        <212> TYPE: PRT
        <213> ORGANISM: Artificial sequence
        <220> FEATURE:
        <223> OTHER INFORMATION: S928_F CSR construct aa sequence

<400> SEQUENCE: 22

Met Ser Ala Leu Pro Val Thr Ala Leu Leu Leu Pro Leu Ala Leu Leu
        1                   5                   10                  15

Leu His Ala Ala Arg Pro Gln Thr Ser Lys Leu Leu Thr Met Gln Ser
                        20                  25                  30

Ser Val Thr Val Gln Glu Gly Leu Cys Val His Val Pro Cys Ser Phe
                        35                  40                  45

Ser Tyr Pro Ser His Gly Trp Ile Tyr Pro Gly Pro Val Val His Gly
                50                  55                  60

Tyr Trp Phe Arg Glu Gly Ala Asn Thr Asp Gln Asp Ala Pro Val Ala
```

```
65                    70                    75                    80

Thr Asn Asn Pro Ala Arg Ala Val Trp Glu Glu Thr Arg Asp Arg Phe
                85                    90                    95

His Leu Leu Gly Asp Pro His Thr Lys Asn Cys Thr Leu Ser Ile Arg
                100                   105                   110

Asp Ala Arg Arg Ser Asp Ala Gly Arg Tyr Phe Phe Arg Met Glu Lys
                115                   120                   125

Gly Ser Ile Lys Trp Asn Tyr Lys His His Arg Leu Ser Val Asn Val
        130                   135                   140

Thr Ala Leu Thr His Arg Pro Asn Ile Leu Ile Pro Gly Thr Leu Glu
145                   150                   155                   160

Ser Gly Cys Pro Gln Asn Leu Thr Cys Ser Val Pro Trp Ala Cys Glu
                165                   170                   175

Gln Gly Thr Pro Pro Met Ile Ser Trp Ile Gly Thr Ser Val Ser Pro
                180                   185                   190

Leu Asp Pro Ser Thr Thr Arg Ser Ser Val Leu Thr Leu Ile Pro Gln
                195                   200                   205

Pro Gln Asp His Gly Thr Ser Leu Thr Cys Gln Val Thr Phe Pro Gly
        210                   215                   220

Ala Ser Val Thr Thr Asn Lys Thr Val His Leu Asn Val Ser Tyr Pro
225                   230                   235                   240

Pro Gln Asn Leu Thr Met Thr Val Phe Gln Gly Asp Gly Thr Val Ser
                245                   250                   255

Thr Val Leu Gly Asn Gly Ser Ser Leu Ser Leu Pro Glu Gly Gln Ser
                260                   265                   270

Leu Arg Leu Val Cys Ala Val Asp Ala Val Asp Ser Asn Pro Pro Ala
        275                   280                   285

Arg Leu Ser Leu Ser Trp Arg Gly Leu Thr Leu Cys Pro Ser Gln Pro
        290                   295                   300

Ser Asn Pro Gly Val Leu Glu Leu Pro Trp Val His Leu Arg Asp Ala
305                   310                   315                   320

Ala Glu Phe Thr Cys Arg Ala Gln Asn Pro Leu Gly Ser Gln Gln Val
                325                   330                   335

Tyr Leu Asn Val Ser Ile Glu Val Met Tyr Pro Pro Pro Tyr Leu Asp
                340                   345                   350

Asn Glu Lys Ser Asn Gly Thr Ile Ile His Val Lys Gly Lys His Leu
        355                   360                   365

Cys Pro Ser Pro Leu Phe Pro Gly Pro Ser Lys Pro Phe Trp Val Leu
        370                   375                   380

Val Val Val Gly Gly Val Leu Ala Cys Tyr Ser Leu Leu Val Thr Val
385                   390                   395                   400

Ala Phe Ile Ile Phe Trp Val Lys Arg Gly Arg Lys Lys Leu Leu Tyr
                405                   410                   415

Ile Phe Lys Gln Pro Phe Met Arg Pro Val Gln Thr Thr Gln Glu Glu
                420                   425                   430

Asp Gly Cys Ser Cys Arg Phe Pro Glu Glu Glu Glu Gly Gly Cys Glu
        435                   440                   445

Leu
```

<210> SEQ ID NO 23
<211> LENGTH: 454
<212> TYPE: PRT
<213> ORGANISM: Artificial sequence
<220> FEATURE:

<223> OTHER INFORMATION: S928_G CSR construct aa sequence

<400> SEQUENCE: 23

```
Met Ser Ala Leu Pro Val Thr Ala Leu Leu Leu Pro Leu Ala Leu Leu
1               5                   10                  15

Leu His Ala Ala Arg Pro Gln Thr Ser Lys Leu Leu Thr Met Gln Ser
                20                  25                  30

Ser Val Thr Val Gln Glu Gly Leu Cys Val His Val Pro Cys Ser Phe
            35                  40                  45

Ser Tyr Pro Ser His Gly Trp Ile Tyr Pro Gly Pro Val Val His Gly
        50                  55                  60

Tyr Trp Phe Arg Glu Gly Ala Asn Thr Asp Gln Asp Ala Pro Val Ala
65                  70                  75                  80

Thr Asn Asn Pro Ala Arg Ala Val Trp Glu Glu Thr Arg Asp Arg Phe
                85                  90                  95

His Leu Leu Gly Asp Pro His Thr Lys Asn Cys Thr Leu Ser Ile Arg
                100                 105                 110

Asp Ala Arg Arg Ser Asp Ala Gly Arg Tyr Phe Phe Arg Met Glu Lys
            115                 120                 125

Gly Ser Ile Lys Trp Asn Tyr Lys His His Arg Leu Ser Val Asn Val
        130                 135                 140

Thr Ala Leu Thr His Arg Pro Asn Ile Leu Ile Pro Gly Thr Leu Glu
145                 150                 155                 160

Ser Gly Cys Pro Gln Asn Leu Thr Cys Ser Val Pro Trp Ala Cys Glu
                165                 170                 175

Gln Gly Thr Pro Pro Met Ile Ser Trp Ile Gly Thr Ser Val Ser Pro
            180                 185                 190

Leu Asp Pro Ser Thr Thr Arg Ser Ser Val Leu Thr Leu Ile Pro Gln
            195                 200                 205

Pro Gln Asp His Gly Thr Ser Leu Thr Cys Gln Val Thr Phe Pro Gly
        210                 215                 220

Ala Ser Val Thr Thr Asn Lys Thr Val His Leu Asn Val Ser Tyr Pro
225                 230                 235                 240

Pro Gln Asn Leu Thr Met Thr Val Phe Gln Gly Asp Gly Thr Val Ser
                245                 250                 255

Thr Val Leu Gly Asn Gly Ser Ser Leu Ser Leu Pro Glu Gly Gln Ser
            260                 265                 270

Leu Arg Leu Val Cys Ala Val Asp Ala Val Asp Ser Asn Pro Pro Ala
        275                 280                 285

Arg Leu Ser Leu Ser Trp Arg Gly Leu Thr Leu Cys Pro Ser Gln Pro
    290                 295                 300

Ser Asn Pro Gly Val Leu Glu Leu Pro Trp Val His Leu Arg Asp Ala
305                 310                 315                 320

Ala Glu Phe Thr Cys Arg Ala Gln Asn Pro Leu Gly Ser Gln Gln Val
                325                 330                 335

Tyr Leu Asn Val Ser Lys Pro Thr Thr Thr Pro Ala Pro Arg Pro Pro
            340                 345                 350

Thr Pro Ala Pro Thr Ile Ala Ser Gln Pro Leu Ser Leu Arg Pro Glu
        355                 360                 365

Ala Cys Arg Pro Ala Ala Gly Gly Ala Val His Thr Arg Gly Leu Asp
    370                 375                 380

Phe Ala Cys Asp Ile Tyr Ile Trp Ala Pro Leu Ala Gly Thr Cys Gly
385                 390                 395                 400
```

```
Val Leu Leu Leu Ser Leu Val Ile Thr Leu Tyr Cys Lys Arg Gly Arg
            405                 410                 415

Lys Lys Leu Leu Tyr Ile Phe Lys Gln Pro Phe Met Arg Pro Val Gln
            420                 425                 430

Thr Thr Gln Glu Glu Asp Gly Cys Ser Cys Arg Phe Pro Glu Glu Glu
            435                 440                 445

Glu Gly Gly Cys Glu Leu
        450

<210> SEQ ID NO 24
<211> LENGTH: 112
<212> TYPE: PRT
<213> ORGANISM: Artificial sequence
<220> FEATURE:
<223> OTHER INFORMATION: CD3 zeta cytosplasmic

<400> SEQUENCE: 24

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 25
<211> LENGTH: 41
<212> TYPE: PRT
<213> ORGANISM: Artificial sequence
<220> FEATURE:
<223> OTHER INFORMATION: CD28 cytosplasmic

<400> SEQUENCE: 25

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 26
<211> LENGTH: 42
<212> TYPE: PRT
<213> ORGANISM: Artificial sequence
<220> FEATURE:
<223> OTHER INFORMATION: 41BB cytosplasmic

<400> SEQUENCE: 26

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
```

```
                35                  40

<210> SEQ ID NO 27
<211> LENGTH: 27
<212> TYPE: PRT
<213> ORGANISM: Artificial sequence
<220> FEATURE:
<223> OTHER INFORMATION: CD28 TransMembrane

<400> SEQUENCE: 27

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 28
<211> LENGTH: 39
<212> TYPE: PRT
<213> ORGANISM: Artificial sequence
<220> FEATURE:
<223> OTHER INFORMATION: CD28 Hinge

<400> SEQUENCE: 28

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
         35

<210> SEQ ID NO 29
<211> LENGTH: 23
<212> TYPE: PRT
<213> ORGANISM: Artificial sequence
<220> FEATURE:
<223> OTHER INFORMATION: SIGLEC7 TransMembrane

<400> SEQUENCE: 29

Gly Ala Val Gly Gly Ala Gly Ala Thr Ala Leu Val Phe Leu Ser Phe
1               5                   10                  15

Cys Val Ile Phe Ile Val Val
            20

<210> SEQ ID NO 30
<211> LENGTH: 11
<212> TYPE: PRT
<213> ORGANISM: Artificial sequence
<220> FEATURE:
<223> OTHER INFORMATION: SIGLEC7 Hinge in S7-hinge construct

<400> SEQUENCE: 30

Leu Gln Gln Glu Tyr Thr Gly Lys Met Arg Pro
1               5                   10

<210> SEQ ID NO 31
<211> LENGTH: 17
<212> TYPE: PRT
<213> ORGANISM: Artificial sequence
<220> FEATURE:
<223> OTHER INFORMATION: SIGLEC7 Hinge in s7TM28 and s7TMSG constructs

<400> SEQUENCE: 31

Leu Gln Gln Glu Tyr Thr Gly Lys Met Arg Pro Val Ser Gly Val Leu
1               5                   10                  15
```

-continued

Leu

<210> SEQ ID NO 32
<211> LENGTH: 22
<212> TYPE: PRT
<213> ORGANISM: Artificial sequence
<220> FEATURE:
<223> OTHER INFORMATION: SIGLEC9 TransMembrane

<400> SEQUENCE: 32

Val Val Gly Gly Ala Gly Ala Thr Ala Leu Val Phe Leu Ser Phe Cys
1               5                   10                  15

Val Ile Phe Val Val Val
            20

<210> SEQ ID NO 33
<211> LENGTH: 12
<212> TYPE: PRT
<213> ORGANISM: Artificial sequence
<220> FEATURE:
<223> OTHER INFORMATION: SIGLEC9 Hinge

<400> SEQUENCE: 33

Leu Gln Ser Lys Ala Thr Ser Gly Val Thr Gln Gly
1               5                   10

<210> SEQ ID NO 34
<211> LENGTH: 47
<212> TYPE: PRT
<213> ORGANISM: Artificial sequence
<220> FEATURE:
<223> OTHER INFORMATION: CD8a Hinge

<400> SEQUENCE: 34

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp
        35                  40                  45

<210> SEQ ID NO 35
<211> LENGTH: 21
<212> TYPE: PRT
<213> ORGANISM: Artificial sequence
<220> FEATURE:
<223> OTHER INFORMATION: CD8a TM

<400> SEQUENCE: 35

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 36
<211> LENGTH: 1608
<212> TYPE: DNA
<213> ORGANISM: Artificial sequence
<220> FEATURE:
<223> OTHER INFORMATION: S7TM28 construct nt sequence

<400> SEQUENCE: 36
atgtcgctgc tgctgctgct gctgcccctg ctctggggga gggagagggt ggaaggacag        60
aagagtaacc ggaaggatta ctcgctgacg atgcagagtt ccgtgaccgt gcaagagggc       120

```
atgtgtgtcc atgtgcgctg ctccttctcc tacccagtgg acagccagac tgactctgac        180
ccagttcatg gctactggtt ccgggcaggg aatgatataa gctggaaggc tccagtggcc        240
acaaacaacc cagcttgggc agtgcaggag gaaactcggg accgattcca cctccttggg        300
gacccacaga ccaaaaattg caccctgagc atcagagatg ccagaatgag tgatgcgggg        360
agatacttct ttcgtatgga gaaaggaaat ataaaatgga attataaata tgaccagctc        420
tctgtgaacg tgacagcctt gacccacagg cccaacatcc ttatccccgg taccctggag        480
tctggctgct tccagaatct gacctgctct gtgccctggg cctgtgagca ggggacgccc        540
cctatgatct cctggatggg gacctctgtg tcccccctgc accctccac cacccgctcc        600 tcagtgctca ccctcatccc acagccccag caccacggca ccagcctcac ctgtcaggtg        660
accttgcctg gggccggcgt gaccacgaac aggaccatcc aactcaatgt gtcctaccct        720
cctcagaact tgactgtgac tgtcttccaa ggagaaggca cagcatccac agctctgggg        780
aacagctcat ctctttcagt cctagagggc cagtctctgc gcttggtctg tgctgttgac        840
agcaatcccc ctgccaggct gagctggacc tggaggagtc tgaccctgta cccctcacag        900
ccctcaaacc ctctggtact ggagctgcaa gtgcacctgg gggatgaagg ggaattcacc        960
tgtcgagctc agaactctct gggttcccag cacgtttccc tgaacctctc cctgcaacag       1020
gagtacacag gcaaaatgag gcctgtatca ggagtgttgc tggcgagctt ttgggtgctg       1080
gtggtggttg gtggagtcct ggcttgctat agcttgctag taacagtggc ctttattatt       1140
ttctgggtga ggagtaagag gagcaggctc ctgcacagtg actacatgaa catgactccc       1200
cgccgccccg ggcccacccg caagcattac cagccctatg ccccaccacg cgacttcgca       1260
gcctatcgct ccagagtgaa gttcagcagg agcgcagacg cccccgcgta ccagcagggc       1320
cagaaccagc tctataacga gctcaatcta ggacgaagag aggagtacga tgttttggac       1380
aagagacgtg gccgggaccc tgagatgggg ggaaagccga gaaggaagaa ccctcaggaa       1440
ggcctgtaca atgaactgca gaaagataag atggcggagg cctacagtga gattgggatg       1500
aaaggcgagc gccggagggg caaggggcac gatggccttt accagggtct cagtacagcc       1560
accaaggaca cctacgacgc ccttcacatg caggccctgc cccctcgc                    1608
```

<210> SEQ ID NO 37
<211> LENGTH: 1590
<212> TYPE: DNA
<213> ORGANISM: Artificial sequence
<220> FEATURE:
<223> OTHER INFORMATION: S7TMSG construct nt sequence

<400> SEQUENCE: 37

```
atgtcgctgc tgctgctgct gctgcccctg ctctggggga gggagagggt ggaaggacag         60
aagagtaacc ggaaggatta ctcgctgacg atgcagagtt ccgtgaccgt gcaagagggc        120
atgtgtgtcc atgtgcgctg ctccttctcc tacccagtgg acagccagac tgactctgac        180
ccagttcatg gctactggtt ccgggcaggg aatgatataa gctggaaggc tccagtggcc        240
acaaacaacc cagcttgggc agtgcaggag gaaactcggg accgattcca cctccttggg        300
gacccacaga ccaaaaattg caccctgagc atcagagatg ccagaatgag tgatgcgggg        360
agatacttct ttcgtatgga gaaaggaaat ataaaatgga attataaata tgaccagctc        420
tctgtgaacg tgacagcctt gacccacagg cccaacatcc ttatccccgg taccctggag        480
tctggctgct tccagaatct gacctgctct gtgccctggg cctgtgagca ggggacgccc        540
```

-continued

```
cctatgatct cctggatggg gacctctgtg tcccccctgc acccctccac cacccgctcc      600
tcagtgctca ccctcatccc acagccccag caccacggca ccagcctcac ctgtcaggtg      660
accttgcctg gggccggcgt gaccacgaac aggaccatcc aactcaatgt gtcctaccct      720
cctcagaact tgactgtgac tgtcttccaa ggagaaggca cagcatccac agctctgggg      780
aacagctcat ctctttcagt cctagagggc cagtctctgc gcttggtctg tgctgttgac      840
agcaatcccc ctgccaggct gagctggacc tggaggagtc tgaccctgta cccctcacag      900
ccctcaaacc ctctggtact ggagctgcaa gtgcacctgg gggatgaagg ggaattcacc      960
tgtcgagctc agaactctct gggttcccag cacgtttccc tgaacctctc cctgcaacag     1020
gagtacacag gcaaaatgag gcctgtatca ggagtgttgc tgggggcggt cggggggagct     1080 ggagccacag ccctggtctt cctctccttc tgtgtcatct tcattgtagt gaggagtaag     1140
aggagcaggc tcctgcacag tgactacatg aacatgactc cccgccgccc cgggcccacc     1200
cgcaagcatt accagcccta tgccccacca cgcgacttcg cagcctatcg ctccagagtg     1260
aagttcagca ggagcgcaga cgcccccgcg taccagcagg gccagaacca gctctataac     1320
gagctcaatc taggacgaag agaggagtac gatgttttgg acaagagacg tggccgggac     1380
cctgagatgg ggggaaagcc gagaaggaag aaccctcagg aaggcctgta caatgaactg     1440
cagaaagata gatggcggga ggcctacagt gagattggga tgaaaggcga gcgccggagg     1500
ggcaaggggc acgatggcct ttaccagggt ctcagtacag ccaccaagga cacctacgac     1560
gcccttcaca tgcaggccct gcccccctcgc                                     1590
```

<210> SEQ ID NO 38
<211> LENGTH: 1584
<212> TYPE: DNA
<213> ORGANISM: Artificial sequence
<220> FEATURE:
<223> OTHER INFORMATION: S7HINGE construct nt sequence

<400> SEQUENCE: 38

```
atgtcgctgc tgctgctgct gctgcccctg ctctggggga gggagagggt ggaaggacag       60
aagagtaacc ggaaggatta ctcgctgacg atgcagagtt ccgtgaccgt gcaagagggc      120
atgtgtgtcc atgtgcgctg ctccttctcc tacccagtgg acagccagac tgactctgac      180
ccagttcatg gctactggtt ccgggcaggg aatgatataa gctggaaggc tccagtggcc      240
acaaacaacc cagcttgggc agtgcaggag gaaactcggg accgattcca cctccttggg      300
gaccacagaa ccaaaaattg caccctgagc atcagagatg ccagaatgag tgatgcgggg      360
agatacttct ttcgtatgga gaaaggaaat ataaaatgga attataaata tgaccagctc      420
tctgtgaacg tgcagacctt gacccacagg cccaacatcc ttatccccgg taccctggag      480
tctggctgct tccagaatct gacctgctct gtgccctggg cctgtgagca ggggacgccc      540
cctatgatct cctggatggg gacctctgtg tcccccctgc acccctccac cacccgctcc      600
tcagtgctca ccctcatccc acagccccag caccacggca ccagcctcac ctgtcaggtg      660
accttgcctg gggccggcgt gaccacgaac aggaccatcc aactcaatgt gtcctaccct      720
cctcagaact tgactgtgac tgtcttccaa ggagaaggca cagcatccac agctctgggg      780
aacagctcat ctctttcagt cctagagggc cagtctctgc gcttggtctg tgctgttgac      840
agcaatcccc ctgccaggct gagctggacc tggaggagtc tgaccctgta cccctcacag      900
ccctcaaacc ctctggtact ggagctgcaa gtgcacctgg gggatgaagg ggaattcacc      960
tgtcgagctc agaactctct gggttcccag cacgtttccc tgaacctctc cctgcaacag     1020
```

-continued

```
gagtacacag gcaaaatgag gcctttttgg gtgctggtgg tggttggtgg agtcctggct    1080
tgctatagct tgctagtaac agtggccttt attattttct gggtgaggag taagaggagc    1140
aggctcctgc acagtgacta catgaacatg actccccgcc gccccgggcc cacccgcaag    1200
cattaccagc cctatgcccc accacgcgac ttcgcagcct atcgctccag agtgaagttc    1260
agcaggagcg cagacgcccc cgcgtaccag cagggccaga accagctcta taacgagctc    1320
aatctaggac gaagagagga gtacgatgtt ttggacaaga gacgtggccg ggaccctgag    1380
atggggggaa agccgagaag gaagaaccct caggaaggcc tgtacaatga actgcagaaa    1440
gataagatgg cggaggccta cagtgagatt gggatgaaag gcgagcgccg gaggggcaag    1500
gggcacgatg gcctttacca gggtctcagt acagccacca aggacaccta cgacgccctt    1560
cacatgcagg ccctgccccc tcgc                                          1584
```

<210> SEQ ID NO 39
<211> LENGTH: 1587
<212> TYPE: DNA
<213> ORGANISM: Artificial sequence
<220> FEATURE:
<223> OTHER INFORMATION: S9TM28 construct nt sequence

<400> SEQUENCE: 39

```
atgtcgctgc tgctgctgct gcccctgctc tgggggaggg agagggcgga aggacagaca      60
agtaaactgc tgacgatgca gagttccgtg acggtgcagg aaggcctgtg tgtccatgtg     120
ccctgctcct tctcctaccc ctcgcatggc tggatttacc ctggcccagt agttcatggc     180
tactggttcc gggaaggggc caatacagac caggatgctc cagtggccac aaacaaccca     240
gctcgggcag tgtgggagga gactcgggac cgattccacc tccttgggga cccacatacc     300
aagaattgca ccctgagcat cagagatgcc agaagaagtg atgcggggag atacttcttt     360
cgtatggaga aaggaagtat aaaatggaat tataaacatc accggctctc tgtgaatgtg     420
acagccttga cccacaggcc caacatcctc atcccaggca ccctggagtc cggctgcccc     480
cagaatctga cctgctctgt gccctgggc tgtgagcagg ggacaccccc tatgatctcc      540 tggatagga cctccgtgtc cccctggac cctccacca cccgctcctc ggtgctcacc         600
ctcatcccac agccccagga ccatggcacc agcctcacct gtcaggtgac cttccctggg      660
gccagcgtga ccacgaacaa gaccgtccat ctcaacgtgt cctacccgcc tcagaacttg      720
accatgactg tcttccaagg agacggcaca gtatccacag tcttgggaaa tggctcatct      780
ctgtcactcc agagggcca gtctctgcgc ctggtctgtg cagttgatgc agttgacagc       840 aatcccctg ccaggctgag cctgagctgg agaggcctga ccctgtgccc ctcacagccc       900
tcaaacccgg gggtgctgga gctgccttgg gtgcacctga gggatgcagc tgaattcacc      960
tgcagagctc agaaccctct cggctctcag caggtctacc tgaacgtctc cctgcagagc     1020
aaagccacat caggagtgac tcaggggttt tgggtgctgg tggtggttgg tggagtcctg     1080
gcttgctata gcttgctagt aacagtggcc tttattattt tctgggtgag gagtaagagg     1140
agcaggctcc tgcacagtga ctacatgaac atgactcccc gccgcccgg gcccacccgc     1200 aagcattacc agccctatgc cccaccacgc gacttcgcag cctatcgctc cagagtgaag     1260
ttcagcagga gcgcagacgc ccccgcgtac cagcagggcc agaaccagct ctataacgag     1320
ctcaatctag acgaagagag ggagtacgat gtttttggaca agagacgtgg ccgggaccct    1380
gagatggggg gaaagccgag aaggaagaac cctcaggaag gcctgtacaa tgaactgcag     1440
```

```
aaagataaga tggcggaggc ctacagtgag attgggatga aaggcgagcg ccggaggggc    1500
aaggggcacg atggccttta ccagggtctc agtacagcca ccaaggacac ctacgacgcc    1560
cttcacatgc aggccctgcc ccctcgc                                        1587
```

<210> SEQ ID NO 40
<211> LENGTH: 1572
<212> TYPE: DNA
<213> ORGANISM: Artificial sequence
<220> FEATURE:
<223> OTHER INFORMATION: S9TMSG construct nt sequence

<400> SEQUENCE: 40

```
atgtcgctgc tgctgctgct gcccctgctc tggggagggg agagggcgga aggacagaca      60
agtaaactgc tgacgatgca gagttccgtg acggtgcagg aaggcctgtg tgtccatgtg     120
ccctgctcct tctcctaccc ctcgcatggc tggatttacc ctggcccagt agttcatggc     180
tactggttcc gggaaggggc caatacagac caggatgctc cagtggccac aaacaaccca     240
gctcgggcag tgtgggagga gactcgggac cgattccacc tccttgggga cccacatacc     300
aagaattgca ccctgagcat cagagatgcc agaagaagtg atgcggggag atacttcttt     360
cgtatggaga aggaagtat aaaatggaat tataaacatc accggctctc tgtgaatgtg     420
acagccttga cccacaggcc caacatcctc atcccaggca ccctggagtc cggctgcccc     480
cagaatctga cctgctctgt gccctgggcc tgtgagcagg ggacacccc tatgatctcc     540 tggataggga cctccgtgtc cccctggac ccctccacca cccgctcctc ggtgctcacc     600
ctcatcccac agccccagga ccatggcacc agcctcacct gtcaggtgac cttccctggg     660
gccagcgtga ccacgaacaa gaccgtccat ctcaacgtgt cctacccgcc tcagaacttg     720
accatgactg tcttccaagg agacggcaca gtatccacag tcttgggaaa tggctcatct     780
ctgtcactcc cagagggcca gtctctgcgc ctggtctgtg cagttgatgc agttgacagc     840
aatccccctg ccaggctgag cctgagctgg agaggcctga ccctgtgccc ctcacagccc     900
tcaaacccgg gggtgctgga gctgccttgg gtgcacctga gggatgcagc tgaattcacc     960
tgcagagctc agaaccctct cggctctcag caggtctacc tgaacgtctc cctgcagagc    1020
aaagccacat caggagtgac tcaggggtg gtcgggggag ctggagccac agccctggtc    1080
ttcctgtcct tctgcgtcat cttcgttgta gtgaggagta agaggagcag gctcctgcac    1140
agtgactaca tgaacatgac tccccgccgc cccgggccca cccgcaagca ttaccagccc    1200
tatgccccac cacgcgactt cgcagcctat cgctccagag tgaagttcag caggagcgca    1260
gacgcccccg cgtaccagca gggccagaac cagctctata cgagctcaa tctaggacga    1320 agagaggagt acgatgtttt ggacaagaga cgtggccggg accctgagat gggggggaaag    1380 ccgagaagga agaaccctca ggaaggcctg tacaatgaac tgcagaaaga taagatggcg    1440
gaggcctaca gtgagattgg gatgaaaggc gagcgccgga ggggcaaggg gcacgatggc    1500
ctttaccagg gtctcagtac agccaccaag gacacctacg acgcccttca catgcaggcc    1560
ctgcccccct gc                                                       1572
```

<210> SEQ ID NO 41
<211> LENGTH: 1599
<212> TYPE: DNA
<213> ORGANISM: Artificial sequence
<220> FEATURE:
<223> OTHER INFORMATION: S9-PSKP construct nt sequence

<400> SEQUENCE: 41

-continued

```
atgtcgctgc tgctgctgct gcccctgctc tggggagggg agaggcgga  aggacagaca      60 agtaaactgc tgacgatgca gagttccgtg acggtgcagg aaggcctgtg tgtccatgtg     120
ccctgctcct tctcctaccc ctcgcatggc tggatttacc ctggcccagt agttcatggc     180
tactggttcc gggaaggggc caatacagac caggatgctc cagtggccac aaacaaccca     240
gctcgggcag tgtgggagga gactcgggac cgattccacc tccttgggga cccacatacc     300
aagaattgca ccctgagcat cagagatgcc agaagaagtg atgcggggag atacttcttt     360
cgtatggaga aaggaagtat aaaatggaat tataaacatc accggctctc tgtgaatgtg     420
acagccttga cccacaggcc caacatcctc atcccaggca ccctggagtc cggctgcccc     480
cagaatctga cctgctctgt gccctgggcc tgtgagcagg ggacaccccc tatgatctcc     540
tggataggga cctccgtgtc cccctggac  ccctccacca cccgctcctc ggtgctcacc     600
ctcatcccac agccccagga ccatggcacc agcctcacct gtcaggtgac cttccctggg     660
gccagcgtga ccacgaacaa gaccgtccat ctcaacgtgt cctacccgcc tcagaacttg     720
accatgactg tcttccaagg agacggcaca gtatccacag tcttgggaaa tggctcatct     780
ctgtcactcc cagagggcca gtctctgcgc ctggtctgtg cagttgatgc agttgacagc     840
aatccccctg ccaggctgag cctgagctgg agaggcctga ccctgtgccc ctcacagccc     900
tcaaacccgg gggtgctgga gctgccttgg gtgcacctga gggatgcagc tgaattcacc     960
tgcagagctc agaaccctct cggctctcag caggtctacc tgaacgtctc cctgcagagc    1020
aaagccacat caggagtgac tcaggggcct tctaagccct tttgggtgct ggtggtggtt    1080
ggtggagtcc tggcttgcta tagcttgcta gtaacagtgg cctttattat tttctgggtg    1140
aggagtaaga ggagcaggct cctgcacagt gactacatga acatgactcc ccgccgcccc    1200
gggcccaccc gcaagcatta ccagccctat gccccaccac gcgacttcgc agcctatcgc    1260
tccagagtga agttcagcag gagcgcagac gcccccgcgt accagcaggg ccagaaccag    1320
ctctataacg agctcaatct aggacgaaga gaggagtacg atgttttgga caagagacgt    1380
ggccgggacc ctgagatggg gggaaagccg agaaggaaga accctcagga aggcctgtac    1440
aatgaactgc agaaagataa gatggcggag gcctacagtg agattgggat gaaaggcgag    1500
cgccggaggg gcaaggggca cgatggcctt taccagggtc tcagtacagc caccaaggac    1560
acctacgacg cccttcacat gcaggccctg cccctcgc                           1599
```

<210> SEQ ID NO 42
<211> LENGTH: 1023
<212> TYPE: DNA
<213> ORGANISM: Artificial sequence
<220> FEATURE:
<223> OTHER INFORMATION: S7D1 construct nt sequence

<400> SEQUENCE: 42

```
atgtcgctgc tgctgctgct gctgcccctg ctctggggga gggagagggt ggaaggacag      60
aagagtaacc ggaaggatta ctcgctgacg atgcagagtt ccgtgaccgt gcaagagggc     120
atgtgtgtcc atgtgcgctg ctccttctcc tacccagtgg acagccagac tgactctgac     180
ccagttcatg gctactggtt ccgggcaggg aatgatataa gctggaaggc tccagtggcc     240
acaaacaacc cagcttgggc agtgcaggag gaaactcggg accgattcca cctccttggg     300
gacccacaga ccaaaaattg caccctgagc atcagagatg ccagaatgag tgatgcgggg     360
agatacttct ttcgtatgga gaaaggaaat ataaaatgga attataaaata tgaccagctc     420
```

-continued

```
tctgtgaacg tgacagcctt gacaggcaaa atgaggcctg tatcaggagt gttgctggcg      480
agcttttggg tgctggtggt ggttggtgga gtcctggctt gctatagctt gctagtaaca      540
gtggccttta ttattttctg ggtgaggagt aagaggagca ggctcctgca cagtgactac      600
atgaacatga ctccccgccg ccccgggccc acccgcaagc attaccagcc ctatgcccca      660
ccacgcgact tcgcagccta tcgctccaga gtgaagttca gcaggagcgc agacgccccc      720
gcgtaccagc agggccagaa ccagctctat aacgagctca atctaggacg aagagaggag      780
tacgatgttt tggacaagag acgtggccgg gaccctgaga tggggggaaa gccgagaagg      840
aagaaccctc aggaaggcct gtacaatgaa ctgcagaaag ataagatggc ggaggcctac      900
agtgagattg ggatgaaagg cgagcgccgg aggggcaagg ggcacgatgg cctttaccag      960
ggtctcagta cagccaccaa ggacacctac gacgcccttc acatgcaggc cctgcccccct     1020 cgc                                                                   1023
```

<210> SEQ ID NO 43
<211> LENGTH: 1335
<212> TYPE: DNA
<213> ORGANISM: Artificial sequence
<220> FEATURE:
<223> OTHER INFORMATION: S7D1+2 construct nt sequence

<400> SEQUENCE: 43

```
atgtcgctgc tgctgctgct gctgcccctg ctctggggga gggagagggt ggaaggacag       60
aagagtaacc ggaaggatta ctcgctgacg atgcagagtt ccgtgaccgt gcaagagggc      120
atgtgtgtcc atgtgcgctg ctccttctcc tacccagtgg acagccagac tgactctgac      180
ccagttcatg gctactggtt ccgggcaggg aatgatataa gctggaaggc tccagtggcc      240
acaaacaacc cagcttgggc agtgcaggag gaaactcggg accgattcca cctccttggg      300
gacccacaga ccaaaaattg caccctgagc atcagagatg ccagaatgag tgatgcgggg      360
agatacttct ttcgtatgga gaaaggaaat ataaaatgga attataaata tgaccagctc      420
tctgtgaacg tgacagcctt gacccacagg cccaacatcc ttatccccgg taccctggag      480
tctggctgct tccagaatct gacctgctct gtgccctggg cctgtgagca ggggacgccc      540
cctatgatct cctggatggg gacctctgtg tcccccctgc accctccac cacccgctcc       600 tcagtgctca ccctcatccc acagccccag caccacggca ccagcctcac ctgtcaggtg      660
accttgcctg gggccggcgt gaccacgaac aggaccatcc aactcaatgt gtcctaccct      720
cctcagaact tgactgtgac tgtcttccaa ggcacaggca aaatgaggcc tgtatcagga      780
gtgttgctgg cgagcttttg gggtgctggtg gtggttggtg gagtcctggc ttgctatagc      840
ttgctagtaa cagtggcctt tattattttc tgggtgagga gtaagaggag caggctcctg      900
cacagtgact acatgaacat gactccccgc cgccccgggc ccacccgcaa gcattaccag      960
ccctatgccc caccacgcga cttcgcagcc tatcgctcca gagtgaagtt cagcaggagc     1020
gcagacgccc ccgcgtacca gcagggccag aaccagctct ataacgagct caatctagga     1080
cgaagagagg agtacgatgt tttggacaag agacgtggcc gggaccctga tggggggaa      1140 aagccgagaa ggaagaaccc tcaggaaggc ctgtacaatg aactgcagaa agataagatg     1200
gcggaggcct acagtgagat tgggatgaaa ggcgagcgcc ggaggggcaa ggggcacgat     1260
ggcctttacc agggtctcag tacagccacc aaggacacct acgacgccct tcacatgcag     1320
gccctgcccc ctcgc                                                      1335
```

-continued

```
<210> SEQ ID NO 44
<211> LENGTH: 1338
<212> TYPE: DNA
<213> ORGANISM: Artificial sequence
<220> FEATURE:
<223> OTHER INFORMATION: S7D1+3 construct nt sequence

<400> SEQUENCE: 44
atgtcgctgc tgctgctgct gctgcccctg ctctggggga gggagagggt ggaaggacag       60
aagagtaacc ggaaggatta ctcgctgacg atgcagagtt ccgtgaccgt gcaagagggc      120
atgtgtgtcc atgtgcgctg ctccttctcc tacccagtgg acagccagac tgactctgac      180
ccagttcatg gctactggtt ccgggcaggg aatgatataa gctggaaggc tccagtggcc      240
acaaacaacc cagcttgggc agtgcaggag gaaactcggg accgattcca cctccttggg      300
gacccacaga ccaaaaattg caccctgagc atcagagatg ccagaatgag tgatgcgggg      360
agatacttct ttcgtatgga gaaaggaaat ataaaatgga attataaata tgaccagctc      420
tctgtgaacg tgacagcctt gacctaccct cctcagaact tgactgtgac tgtcttccaa      480
ggagaaggca cagcatccac agctctgggg aacagctcat ctctttcagt cctagagggc      540
cagtctctgc gcttggtctg tgctgttgac agcaatcccc ctgccaggct gagctggacc      600
tggaggagtc tgaccctgta cccctcacag ccctcaaacc ctctggtact ggagctgcaa      660
gtgcacctgg gggatgaagg ggaattcacc tgtcgagctc agaactctct gggttcccag      720
cacgtttccc tgaacctctc cctgcaacag gagtacacag gcaaaatgag gcctgtatca      780
ggagtgttgc tggcgagctt ttgggtgctg gtggtggttg gtggagtcct ggcttgctat      840
agcttgctag taacagtggc ctttattatt ttctgggtga ggagtaagag gagcaggctc      900
ctgcacagtg actacatgaa catgactccc cgccgccccg ggcccacccg caagcattac      960
cagccctatg ccccaccacg cgacttcgca gcctatcgct ccagagtgaa gttcagcagg     1020
agcgcagacg cccccgcgta ccagcagggc cagaaccagc tctataacga gctcaatcta     1080
ggacgaagag aggagtacga tgttttggac aagagacgtg gccgggaccc tgagatgggg     1140
ggaaagccga aaggaagaa ccctcaggaa ggcctgtaca tgaactgca gaaagataag     1200 atggcggagg cctacagtga gattgggatg aaaggcgagc gccggagggg caaggggcac     1260
gatggccttt accagggtct cagtacagcc accaaggaca cctacgacgc ccttcacatg     1320
caggccctgc cccctcgc                                                   1338

<210> SEQ ID NO 45
<211> LENGTH: 1272
<212> TYPE: DNA
<213> ORGANISM: Artificial sequence
<220> FEATURE:
<223> OTHER INFORMATION: S728 CSR construct nt sequence

<400> SEQUENCE: 45
atgtcgctgc tgctgctgct gctgcccctg ctctggggga gggagagggt ggaaggacag       60
aagagtaacc ggaaggatta ctcgctgacg atgcagagtt ccgtgaccgt gcaagagggc      120
atgtgtgtcc atgtgcgctg ctccttctcc tacccagtgg acagccagac tgactctgac      180
ccagttcatg gctactggtt ccgggcaggg aatgatataa gctggaaggc tccagtggcc      240
acaaacaacc cagcttgggc agtgcaggag gaaactcggg accgattcca cctccttggg      300
gacccacaga ccaaaaattg caccctgagc atcagagatg ccagaatgag tgatgcgggg      360
agatacttct ttcgtatgga gaaaggaaat ataaaatgga attataaata tgaccagctc      420
```

-continued

```
tctgtgaacg tgacagcctt gacccacagg cccaacatcc ttatccccgg taccctggag    480
tctggctgct tccagaatct gacctgctct gtgccctggg cctgtgagca ggggacgccc    540
cctatgatct cctggatggg gacctctgtg tcccccctgc acccctccac cacccgctcc    600
tcagtgctca ccctcatccc acagccccag caccacggca ccagcctcac ctgtcaggtg    660
accttgcctg gggccggcgt gaccacgaac aggaccatcc aactcaatgt gtcctaccct    720
cctcagaact tgactgtgac tgtcttccaa ggagaaggca cagcatccac agctctgggg    780
aacagctcat ctctttcagt cctagagggc cagtctctgc gcttggtctg tgctgttgac    840
agcaatcccc ctgccaggct gagctggacc tggaggagtc tgaccctgta cccctcacag    900
ccctcaaacc ctctggtact ggagctgcaa gtgcacctgg gggatgaagg ggaattcacc    960
tgtcgagctc agaactctct gggttcccag cacgtttccc tgaacctctc cctgcaacag   1020
gagtacacag gcaaaatgag gcctgtatca ggagtgttgc tggcgagctt ttgggtgctg   1080
gtggtggttg gtggagtcct ggcttgctat agcttgctag taacagtggc ctttattatt   1140
ttctgggtga ggagtaagag gagcaggctc ctgcacagtg actacatgaa catgactccc   1200
cgccgccccg ggcccacccg caagcattac cagccctatg ccccaccacg cgacttcgca   1260
gcctatcgct cc                                                      1272
```

```
<210> SEQ ID NO 46
<211> LENGTH: 1251
<212> TYPE: DNA
<213> ORGANISM: Artificial sequence
<220> FEATURE:
<223> OTHER INFORMATION: S928 CSR construct nt sequence

<400> SEQUENCE: 46
atgtcgctgc tgctgctgct gcccctgctc tgggggaggg agagggcgga aggacagaca     60
agtaaactgc tgacgatgca gagttccgtg acggtgcagg aaggcctgtg tgtccatgtg    120
ccctgctcct tctcctaccc ctcgcatggc tggatttacc ctggcccagt agttcatggc    180
tactggttcc gggaaggggc caatacagac caggatgctc cagtggccac aaacaaccca    240
gctcgggcag tgtgggagga gactcgggac cgattccacc tccttgggga cccacatacc    300
aagaattgca ccctgagcat cagagatgcc agaagaagtg atgcggggag atacttcttt    360
cgtatggaga aggaagtat aaaatggaat tataaacatc accggctctc tgtgaatgtg    420
acagccttga cccacaggcc caacatcctc atcccaggca ccctggagtc cggctgcccc    480
cagaatctga cctgctctgt gccctgggcc tgtgagcagg gacaccccc tatgatctcc    540 tggatagga cctccgtgtc cccctggac ccctccacca cccgctcctc ggtgctcacc    600
ctcatcccac agccccagga ccatggcacc agcctcacct gtcaggtgac cttccctggg    660
gccagcgtga ccacgaacaa gaccgtccat ctcaacgtgt cctacccgcc tcagaacttg    720
accatgactg tcttccaagg agacggcaca gtatccacag tcttgggaaa tggctcatct    780
ctgtcactcc agagggcca gtctctgcgc ctggtctgtg cagttgatgc agttgacagc    840
aatccccctg ccaggctgag cctgagctgg agaggcctga ccctgtgccc ctcacagccc    900
tcaaacccgg gggtgctgga gctgccttgg gtgcacctga gggatgcagc tgaattcacc    960
tgcagagctc agaaccctct cggctctcag caggtctacc tgaacgtctc cctgcagagc   1020
aaagccacat caggagtgac tcaggggttt tgggtgctgg tggtggttgg tggagtcctg   1080
gcttgctata gcttgctagt aacagtggcc tttattattt tctgggtgag gagtaagagg   1140
agcaggctcc tgcacagtga ctacatgaac atgactcccc gccgccccgg gcccacccgc   1200
```

```
aagcattacc agccctatgc cccaccacgc gacttcgcag cctatcgctc c          1251

<210> SEQ ID NO 47
<211> LENGTH: 1263
<212> TYPE: DNA
<213> ORGANISM: Artificial sequence
<220> FEATURE:
<223> OTHER INFORMATION: S928_B CSR construct nt sequence

<400> SEQUENCE: 47
atgtccgcct taccagtgac cgccttgctc ctgccgctgg ccttgctgct ccacgccgcc   60
aggccacaga caagtaaact gctgacgatg cagagttccg tgacggtgca ggaaggcctg   120
tgtgtccatg tgccctgctc cttctcctac ccctcgcatg gctggattta ccctggccca   180
gtagttcatg gctactggtt ccgggaaggg gccaatacag accaggatgc tccagtggcc   240
acaaacaacc cagctcgggc agtgtgggag gagactcggg accgattcca cctccttggg   300
gacccacata ccaagaattg caccctgagc atcagagatg ccagaagaag tgatgcgggg   360
agatacttct ttcgtatgga gaaggaagt ataaaatgga attataaaca tcaccggctc    420
tctgtgaatg tgacagcctt gacccacagg cccaacatcc tcatcccagg caccctggag   480
tccggctgcc cccagaatct gacctgctct gtgccctggg cctgtgagca ggggacaccc   540
cctatgatct cctggatagg gacctccgtg tccccctgg accctccac cacccgctcc     600 tcggtgctca ccctcatccc acagccccag gaccatggca ccagcctcac ctgtcaggtg   660
accttccctg gggccagcgt gaccacgaac aagaccgtcc atctcaacgt gtcctacccg   720
cctcagaact tgaccatgac tgtcttccaa ggagacggca cagtatccac agtcttggga   780
aatggctcat ctctgtcact cccagagggc cagtctctgc gcctggtctg tgcagttgat   840
gcagttgaca gcaatccccc tgccaggctg agcctgagct ggagaggcct gaccctgtgc   900
ccctcacagc cctcaaaccc gggggtgctg gagctgcctt gggtgcacct gagggatgca   960
gctgaattca cctgcagagc tcagaaccct ctcggctctc agcaggtcta cctgaacgtc   1020
tccctgcaga gcaaagccac atcaggagtg actcaggggt tttgggtgct ggtggtggtt   1080
ggtggagtcc tggcttgcta tagcttgcta gtaacagtgg cctttattat tttctgggtg   1140
aggagtaaga ggagcaggct cctgcacagt gactacatga acatgactcc ccgccgcccc   1200
gggcccaccc gcaagcatta ccagccctat gccccaccac gcgacttcgc agcctatcgc   1260
tcc                                                                  1263

<210> SEQ ID NO 48
<211> LENGTH: 1344
<212> TYPE: DNA
<213> ORGANISM: Artificial sequence
<220> FEATURE:
<223> OTHER INFORMATION: S928_C CSR construct nt sequence

<400> SEQUENCE: 48
atgtccgcct taccagtgac cgccttgctc ctgccgctgg ccttgctgct ccacgccgcc   60
aggccacaga caagtaaact gctgacgatg cagagttccg tgacggtgca ggaaggcctg   120
tgtgtccatg tgccctgctc cttctcctac ccctcgcatg gctggattta ccctggccca   180
gtagttcatg gctactggtt ccgggaaggg gccaatacag accaggatgc tccagtggcc   240
acaaacaacc cagctcgggc agtgtgggag gagactcggg accgattcca cctccttggg   300
gacccacata ccaagaattg caccctgagc atcagagatg ccagaagaag tgatgcgggg   360
```

-continued agatacttct ttcgtatgga gaaaggaagt ataaaatgga attataaaca tcaccggctc        420
tctgtgaatg tgacagcctt gacccacagg cccaacatcc tcatcccagg caccctggag        480
tccggctgcc cccagaatct gacctgctct gtgccctggg cctgtgagca ggggacaccc        540
cctatgatct cctggatagg gacctccgtg tcccccctgg accccctccac cacccgctcc        600 tcggtgctca ccctcatccc acagccccag gaccatggca ccagcctcac ctgtcaggtg        660
accttccctg gggccagcgt gaccacgaac aagaccgtcc atctcaacgt gtcctacccg        720
cctcagaact tgaccatgac tgtcttccaa ggagacggca cagtatccac agtcttggga        780
aatggctcat ctctgtcact cccagagggc cagtctctgc gcctggtctg tgcagttgat        840
gcagttgaca gcaatccccc tgccaggctg agcctgagct ggagaggcct gaccctgtgc        900
ccctcacagc cctcaaaccc gggggtgctg gagctgcctt gggtgcacct gagggatgca        960
gctgaattca cctgcagagc tcagaaccct ctcggctctc agcaggtcta cctgaacgtc       1020
tccatcgaag tgatgtatcc accccccttac ctggataacg agaagagcaa tggcaccatc       1080
atccacgtga agggcaagca cctgtgccct tctccactgt tcccccggccc tagcaagccc       1140 ttttgggtgc tggtggtggt gggaggcgtg ctggcctgtt attctctgct ggtgacagtg       1200
gccttcatca tctttttgggt gaggagcaag cggagccggc tgctgcacag cgactacatg       1260
aacatgaccc caagacggcc cggccccaca agaaagcact atcagccata cgcaccacca       1320
agggacttcg cagcctatag atcc                                             1344

```
<210> SEQ ID NO 49
<211> LENGTH: 1347
<212> TYPE: DNA
<213> ORGANISM: Artificial sequence
<220> FEATURE:
<223> OTHER INFORMATION: S928_F CSR construct nt sequence

<400> SEQUENCE: 49
```
atgtccgcct taccagtgac cgccttgctc ctgccgctgg ccttgctgct ccacgccgcc         60
aggccacaga caagtaaact gctgacgatg cagagttccg tgacggtgca ggaaggcctg        120
tgtgtccatg tgccctgctc cttctcctac ccctcgcatg gctggattta ccctggccca        180
gtagttcatg gctactggtt ccgggaaggg gccaatacag accaggatgc tccagtggcc        240
acaaacaacc cagctcgggc agtgtgggag gagactcggg accgattcca cctccttggg        300
gacccacata ccaagaattg caccctgagc atcagagatg ccagaagaag tgatgcgggg        360
agatacttct ttcgtatgga gaaaggaagt ataaaatgga attataaaca tcaccggctc        420
tctgtgaatg tgacagcctt gacccacagg cccaacatcc tcatcccagg caccctggag        480
tccggctgcc cccagaatct gacctgctct gtgccctggg cctgtgagca ggggacaccc        540
cctatgatct cctggatagg gacctccgtg tcccccctgg accccctccac cacccgctcc        600 tcggtgctca ccctcatccc acagccccag gaccatggca ccagcctcac ctgtcaggtg        660
accttccctg gggccagcgt gaccacgaac aagaccgtcc atctcaacgt gtcctacccg        720
cctcagaact tgaccatgac tgtcttccaa ggagacggca cagtatccac agtcttggga        780
aatggctcat ctctgtcact cccagagggc cagtctctgc gcctggtctg tgcagttgat        840
gcagttgaca gcaatccccc tgccaggctg agcctgagct ggagaggcct gaccctgtgc        900
ccctcacagc cctcaaaccc gggggtgctg gagctgcctt gggtgcacct gagggatgca        960
gctgaattca cctgcagagc tcagaaccct ctcggctctc agcaggtcta cctgaacgtc       1020
tccatcgaag tgatgtatcc accccccttac ctggataacg agaagagcaa tggcaccatc       1080

-continued

```
atccacgtga agggcaagca cctgtgccct tctccactgt tccccggccc tagcaagccc      1140
ttttgggtgc tggtggtggt gggaggcgtg ctggcctgtt attctctgct ggtgacagtg      1200
gcctttatta ttttctgggt gaagagaggc aggaagaagc tgctgtacat cttcaagcag      1260
cccttcatgc ggcccgtgca gacaacccag gaggaggacg gctgctcctg taggttccct      1320
gaagaggagg agggaggatg tgagctg                                          1347
```

<210> SEQ ID NO 50
<211> LENGTH: 1362
<212> TYPE: DNA
<213> ORGANISM: Artificial sequence
<220> FEATURE:
<223> OTHER INFORMATION: S928_G CSR construct nt sequence

<400> SEQUENCE: 50

```
atgtccgcct taccagtgac cgccttgctc ctgccgctgg ccttgctgct ccacgccgcc        60
aggccacaga caagtaaact gctgacgatg cagagttccg tgacggtgca ggaaggcctg       120
tgtgtccatg tgccctgctc cttctcctac ccctcgcatg gctggattta ccctggccca       180
gtagttcatg gctactggtt ccgggaaggg gccaatacag accaggatgc tccagtggcc       240
acaaacaacc cagctcgggc agtgtgggag gagactcggg accgattcca cctccttggg       300
gacccacata ccaagaattg caccctgagc atcagagatg ccagaagaag tgatgcgggg       360
agatacttct ttcgtatgga gaaggaagt ataaaatgga attataaaca tcaccggctc        420
tctgtgaatg tgacagcctt gacccacagg cccaacatcc tcatcccagg caccctggag       480
tccggctgcc cccagaatct gacctgctct gtgccctggg cctgtgagca ggggacaccc       540
cctatgatct cctggatagg gacctccgtg tccccctgg accctccac caccgctcc          600 tcggtgctca ccctcatccc acagccccag gaccatggca ccagcctcac ctgtcaggtg       660
accttccctg gggccagcgt gaccacgaac aagaccgtcc atctcaacgt gtcctacccg       720
cctcagaact tgaccatgac tgtcttccaa ggagacggca cagtatccac agtcttggga       780
aatggctcat ctctgtcact cccagagggc cagtctctgc gcctggtctg tgcagttgat       840
gcagttgaca gcaatccccc tgccaggctg agcctgagct ggagaggcct gaccctgtgc       900
ccctcacagc cctcaaaccc gggggtgctg gagctgcctt gggtgcacct gagggatgca       960
gctgaattca cctgcagagc tcagaaccct ctcggctctc agcaggtcta cctgaacgtc      1020
tccaagccca ccacaacccc tgcaccacgc ccacccacac cagcacctac catcgcaagc      1080
cagccactgt ccctgcggcc cgaggcctgt aggccagcag caggaggagc agtgcacacc      1140
aggggcctgg actttgcctg cgatatctac atctgggcac cactggcagg aacatgtggc      1200
gtgctgctgc tgagcctggt catcaccctg tattgcaaga gaggcaggaa gaagctgctg      1260
tacatcttca agcagccctt catgcggccc gtgcagacaa cccaggagga ggacggctgc      1320
tcctgtaggt tccctgaaga ggaggaggga ggatgtgagc tg                        1362
```

<210> SEQ ID NO 51
<211> LENGTH: 4
<212> TYPE: PRT
<213> ORGANISM: Artificial sequence
<220> FEATURE:
<223> OTHER INFORMATION: binding motif
<220> FEATURE:
<221> NAME/KEY: misc_feature
<222> LOCATION: (2)..(3)
<223> OTHER INFORMATION: Xaa can be any naturally occurring amino acid

```
<400> SEQUENCE: 51

Tyr Xaa Xaa Met
1

<210> SEQ ID NO 52
<211> LENGTH: 4
<212> TYPE: PRT
<213> ORGANISM: Artificial sequence
<220> FEATURE:
<223> OTHER INFORMATION: binding motif

<400> SEQUENCE: 52

Tyr Met Asn Met
1

<210> SEQ ID NO 53
<211> LENGTH: 4
<212> TYPE: PRT
<213> ORGANISM: Artificial sequence
<220> FEATURE:
<223> OTHER INFORMATION: binding motif

<400> SEQUENCE: 53

Pro Arg Arg Pro
1

<210> SEQ ID NO 54
<211> LENGTH: 4
<212> TYPE: PRT
<213> ORGANISM: Artificial sequence
<220> FEATURE:
<223> OTHER INFORMATION: binding motif

<400> SEQUENCE: 54

Pro Tyr Ala Pro
1

<210> SEQ ID NO 55
<211> LENGTH: 4
<212> TYPE: PRT
<213> ORGANISM: Artificial sequence
<220> FEATURE:
<223> OTHER INFORMATION: binding motif

<400> SEQUENCE: 55

Gln Glu Glu Asp
1

<210> SEQ ID NO 56
<211> LENGTH: 4
<212> TYPE: PRT
<213> ORGANISM: Artificial sequence
<220> FEATURE:
<223> OTHER INFORMATION: binding motif

<400> SEQUENCE: 56

Glu Glu Glu Glu
1

<210> SEQ ID NO 57
<211> LENGTH: 6
<212> TYPE: PRT
<213> ORGANISM: Artificial sequence
<220> FEATURE:
<223> OTHER INFORMATION: binding motif

<400> SEQUENCE: 57
```

```
Thr Pro Ile Gln Glu Glu
1               5

<210> SEQ ID NO 58
<211> LENGTH: 5
<212> TYPE: PRT
<213> ORGANISM: Artificial sequence
<220> FEATURE:
<223> OTHER INFORMATION: binding motif

<400> SEQUENCE: 58

Glu Glu Gly Lys Glu
1               5

<210> SEQ ID NO 59
<211> LENGTH: 9
<212> TYPE: PRT
<213> ORGANISM: Artificial sequence
<220> FEATURE:
<223> OTHER INFORMATION: binding motif

<400> SEQUENCE: 59

Val Thr Thr Val Glu Val Glu Glu Thr
1               5

<210> SEQ ID NO 60
<211> LENGTH: 5
<212> TYPE: PRT
<213> ORGANISM: Artificial sequence
<220> FEATURE:
<223> OTHER INFORMATION: binding motif

<400> SEQUENCE: 60

Pro Ile Gln Glu Asp
1               5

<210> SEQ ID NO 61
<211> LENGTH: 20
<212> TYPE: PRT
<213> ORGANISM: Artificial sequence
<220> FEATURE:
<223> OTHER INFORMATION: linker amino acid sequence
<220> FEATURE:
<221> NAME/KEY: REPEAT
<222> LOCATION: (6)..(10)
<223> OTHER INFORMATION: may be absent
<220> FEATURE:
<221> NAME/KEY: REPEAT
<222> LOCATION: (11)..(15)
<223> OTHER INFORMATION: may be absent
<220> FEATURE:
<221> NAME/KEY: REPEAT
<222> LOCATION: (16)..(20)
<223> OTHER INFORMATION: may be absent

<400> SEQUENCE: 61

Gly Gly Gly Gly Ser Gly Gly Gly Ser Gly Gly Gly Gly Ser Gly
1               5                   10                  15

Gly Gly Gly Ser
            20

<210> SEQ ID NO 62
<211> LENGTH: 9
<212> TYPE: PRT
<213> ORGANISM: Artificial sequence
<220> FEATURE:
<223> OTHER INFORMATION: linker amino acid sequence
```

-continued

```
<400> SEQUENCE: 62

Gly Gly Gly Gly Ser Gly Gly Gly Gly
1               5

<210> SEQ ID NO 63
<211> LENGTH: 15
<212> TYPE: PRT
<213> ORGANISM: Artificial sequence
<220> FEATURE:
<223> OTHER INFORMATION: linker amino acid sequence
<220> FEATURE:
<221> NAME/KEY: REPEAT
<222> LOCATION: (5)..(10)
<223> OTHER INFORMATION: may be absent
<220> FEATURE:
<221> NAME/KEY: REPEAT
<222> LOCATION: (11)..(15)
<223> OTHER INFORMATION: may be absent

<400> SEQUENCE: 63

Glu Ala Ala Ala Lys Glu Ala Ala Ala Lys Glu Ala Ala Ala Lys
1               5                   10                  15

<210> SEQ ID NO 64
<211> LENGTH: 4
<212> TYPE: PRT
<213> ORGANISM: Artificial sequence
<220> FEATURE:
<223> OTHER INFORMATION: linker amino acid sequence

<400> SEQUENCE: 64

Pro Ala Pro Ala
1
```